US008617561B2

(12) United States Patent
Mevorach et al.

(10) Patent No.: US 8,617,561 B2
(45) Date of Patent: Dec. 31, 2013

(54) IMMUNE DISEASE MEDICAMENT COMPRISING A MODULATOR OF THE BINDING BETWEEN A HEPARIN BINDING DOMAIN OF THROMBOSPONDIN-1 AND A BETA1 INTEGRIN

(75) Inventors: Dror Mevorach, Jerusalem (IL); Alon Krispin, Moshav Even Sapir (IL); Yaniv Bledi, Jerusalem (IL); Michal Linial, Jerusalem (IL)

(73) Assignees: Hadasit Medical Research Services and Development Ltd. (IL); Yissum Research Development Company of the Hebrew University of Jerusalem (IL)

( * ) Notice: Subject to any disclaimer, the term of this patent is extended or adjusted under 35 U.S.C. 154(b) by 351 days.

(21) Appl. No.: 11/922,607

(22) PCT Filed: Jun. 20, 2006

(86) PCT No.: PCT/IL2006/000712
§ 371 (c)(1),
(2), (4) Date: Aug. 17, 2009

(87) PCT Pub. No.: WO2006/137060
PCT Pub. Date: Dec. 28, 2006

(65) Prior Publication Data
US 2010/0255003 A1  Oct. 7, 2010

Related U.S. Application Data

(60) Provisional application No. 60/691,848, filed on Jun. 20, 2005.

(51) Int. Cl.
*A61K 39/00*  (2006.01)
(52) U.S. Cl.
USPC .................... 424/184.1; 424/185.1; 514/21.2
(58) Field of Classification Search
None
See application file for complete search history.

(56) References Cited

U.S. PATENT DOCUMENTS 6,310,270 B1 * 10/2001 Huang et al. ................... 800/18

OTHER PUBLICATIONS

Bornstein P. Thrombospondins as matricellular modulators of cell function. J Clin Invest. Apr. 2001;107(8):929-34.*
Mansfield PJ, Suchard SJ. Thrombospondin promotes both chemotaxis and haptotaxis in neutrophil-like HL-60 cells. J Immunol. Mar. 1, 1993;150(5):1959-70.*
Mansfield PJ, Suchard SJ. Thrombospondin promotes chemotaxis and haptotaxis of human peripheral blood monocytes. J Immunol. Nov. 1, 1994;153(9):4219-29.*
Crawford et al. Thrombospondin-1 is a major activator of TGF-beta1 in vivo. Cell, 93:1159-1170, 1998.*
Zamiri et al. Thrombospondin plays a vital role in the immune privilege of the eye. Invest Ophthalmol Vis Sci. Mar. 2005;46(3):908-19.*
Agah et al. The lack of thrombospondin-1 (TSP1) dictates the course of wound healing in double-TSP1/TSP2-null mice. Am J Pathol. Sep. 2002;161(3):831-9.*
Skolnick et al. From genes to protein structure and function: novel applications of computational approaches in the genomic era. Trends Biotechnol. 18(1):34-9, 2000.*
Attwood TK. Genomics. The Babel of bioinformatics. Science. 290(5491):471-473, 2000.*
Gutierrez, Linda S. The Role of Thrombospondin 1 on Intestinal Inflammation and Carcinogenesis, Biomark Insights. 2008; 3: 171-178.*
Abeyam et al. TThe N-terminal domain of thrombomodulin sequesters high-mobility group-B1 protein, a novel antiinflammatory mechanism. J Clin Invest. May 2005;115(5):1267-74.*
Yamauchi et al. Thrombospondin-1 Differentially Regulates Release of IL-6 and IL-10 by Human Monocytic Cell Line U937. Biochemical and Biophysical Research Communications 290, 1551-1557 (2002).*
Brand et al. "Influence of Extracellular Matrix Proteins on the Development of Cultured Human Dendritic Cells", European Journal of Immunology, 28(5): 1673-1680, 1998. Abstract.
Cohen et al. "Genetic Models for the Clearance of Apoptotic Cells", Rheumatic Disease Clinics of North America, 30(3): 473-486, 2004.
Critchley et al. "Potential Therapeutic Appplications of Recombinant, Invasive *E. coli*", Gene Therapy, 11(15): 1224-1233, 2004. p. 1224, r-h Col., § 2.
Dieker et al. "Deranged Removal of Apoptotic Cells: Its Role in the Genesis of Lupus", Nephrology Dialysis Transplantation, 19(2): 282-285, 2004. p. 283, 1-h Col., § 2-p. 284.
Doyen et al. "Thrombospondin 1 Is an Autocrine Negative Regulator of Human Dendritic Cell Activation", Journal of Experimental Medicine, 198(8): 1277-1283, 2003. p. 1277, 1-h Col.-p. 1278, 1-h Col., p. 1281.
Jancic et al. "Interactions of Dendritic Cells With Fibronectin and Endothelial Cells", Immunology, 95: 283-290, 1998. Abstract.
Johansson et al. "CD47 Ligation Induces a Rapid Caspase-Independent Apoptosis-Like Cell Death in Human Monocytes and Dendritic Cells", Scandinavian Journal of Immunology, 59(1): 40-49, 2004. Abstract.
Krispin et al. "Apoptotic Cell Thrombospondin-1 and Heparin Binding Domain Lead to Dendritic Cell Phagocytic and Tolerizing States", Blood, 1st Ed.: 1-38, 2006.
Savill et al. "Thrombospondin Cooperates With CD36 and the Vitronectin Receptor in Macrophage Recognition of Neutrophils Undergoing Apoptosis", Journal of Clinical Investigation, 90(4): 1513-1522, 1992. p. 1516, 1-h Col., § 2-p. 1517, r-h Col., § 2.
Verbovetski et al. "Opsonization of Apoptotic Cells by Autologous IC3b Facilitates Clearance by Immature Dendritic Cells, Down-Regulates DR and CD86, and Up-Regulates CC Chemokine Receptor 7", Journal of Experimental Medicine, 196(12): 1553-1561, 2002. Abstract.

(Continued)

*Primary Examiner* — Maher Haddad
(74) *Attorney, Agent, or Firm* — St. Onge Steward Johnston & Reens LLC

(57) ABSTRACT

An article of manufacture comprising packaging material and a pharmaceutical composition is disclosed, the article of manufacture being identified in print in or on the packaging material for treatment of an immunity-related disease in a subject in need thereof. The pharmaceutical composition comprises a pharmaceutically acceptable carrier and, as an active ingredient, a compound being capable of modulating an interaction between a heparin-binding domain of a thrombospondin and a receptor of the heparin-binding domain.

4 Claims, 16 Drawing Sheets

(56) References Cited

OTHER PUBLICATIONS

International Preliminary Report on Patentability Dated Jan. 10, 2008 From the International Bureau of WIPO Re.: Application No. PCT/IL2006/000712.
Communication Pursuant to Article 94(3) EPC Dated Dec. 15, 2010 From the European Patent Office Re.: Application No. 06745154.2.
Communication Pursuant to Article 94(3) EPC Dated Aug. 27, 2009 From the European Patent Office Re.: Application No. 06745154.2.
International Search Report and the Written Opinion Dated Nov. 8, 2006 From the International Searching Authority Re.: Application No. PCT/IL2006/000712.
Response Dated Apr. 10, 2011 to Communication Pursuant to Article 94(3) EPC of Dec. 15, 2010 From the European Patent Office Re.: Application No. 06745154.2.
Bauer et al. "Colitis Induced in Mice With Dextran Sulfate Sodium (DSS) is Mediated by the NLRP3 Inflammasome", GUT, p. 1-8, 2009.
Tschopp et al. "The Inflammasomes", Cell (140): 821-832, 2010.
Wirtz et al. "Chemically Induced Mouse Models of Intestinal inflammation", Nature Protocols, vol. 2(3): 541-546, 2007.
European Office Acton Application No. EP 06 745 154 Dated: Oct. 4, 2013 7 pages
Morandi et al., (2009) The N-terminal domain of thrombospondin-1: a key for the dual effect of TSP-1 in angiogenesis and cancer progression? ScientificWorldJournal 9: 133-6.

* cited by examiner

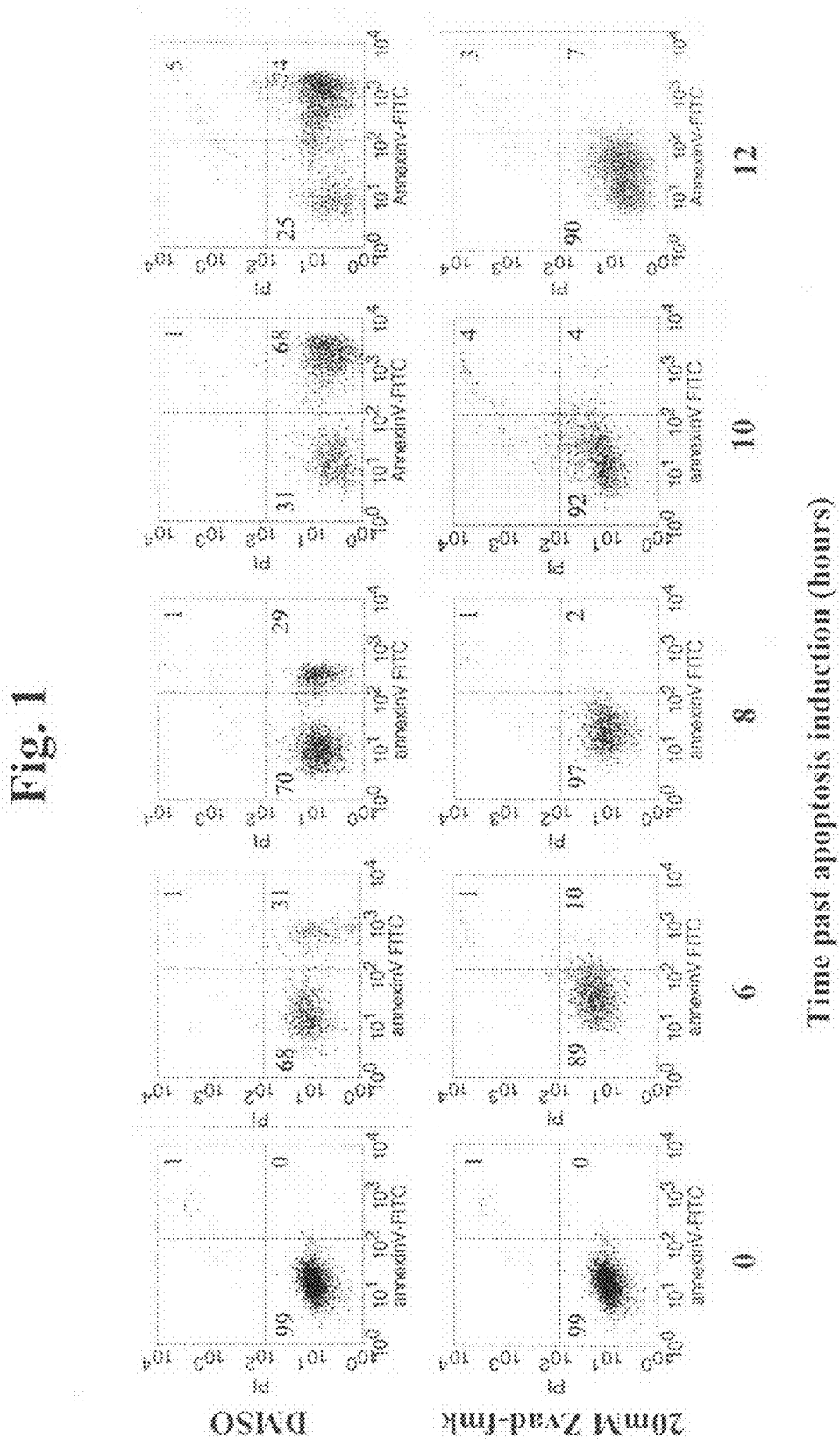

SEQ ID NO: 5

```
  1 MGLAWGLGVL FLMHVCGTNE IPESGGDNSV FDIFELTGAA RKGSGERLVK
 51 GPDPSSPAFR IEDANLIPPV PDDKFQDLVD AVRAEKGFLL LASLRQMKKT
101 RGTLLALERK DHSGQVFSVV SNGKAGTLDL SLTVQGKQHV VSVEEALLAT
151 GQWKSITLFV QEDRAQLYID CEKMENAELD VPIQSVFTRD LASIARLRIA
201 KSGVNDNFQG VLQNVRFVFG TTPEDILENK GC
```

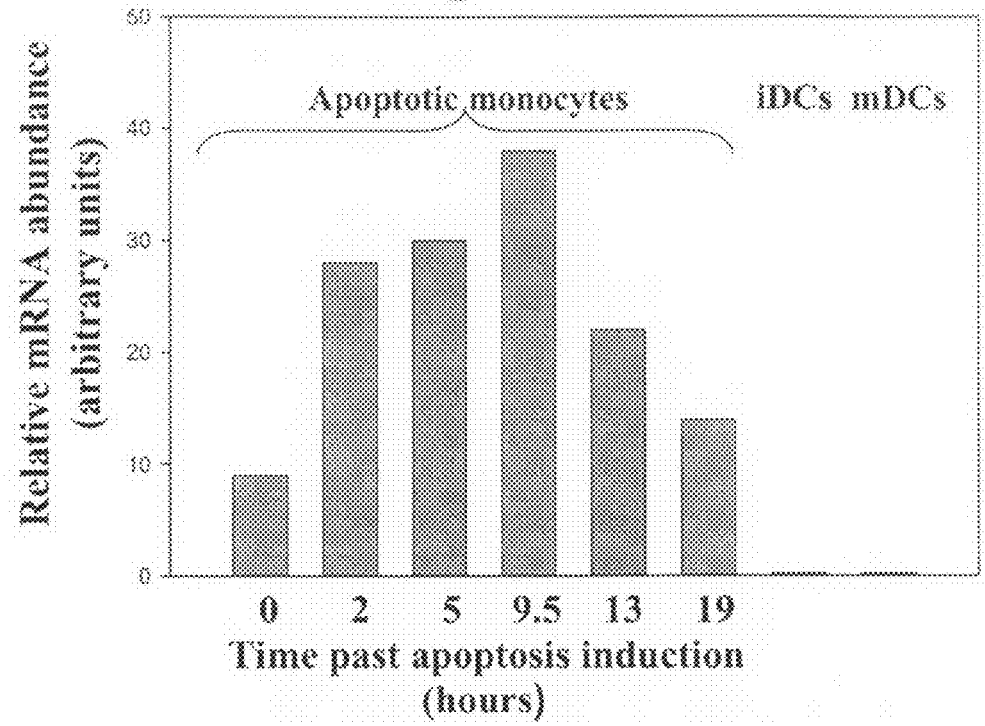
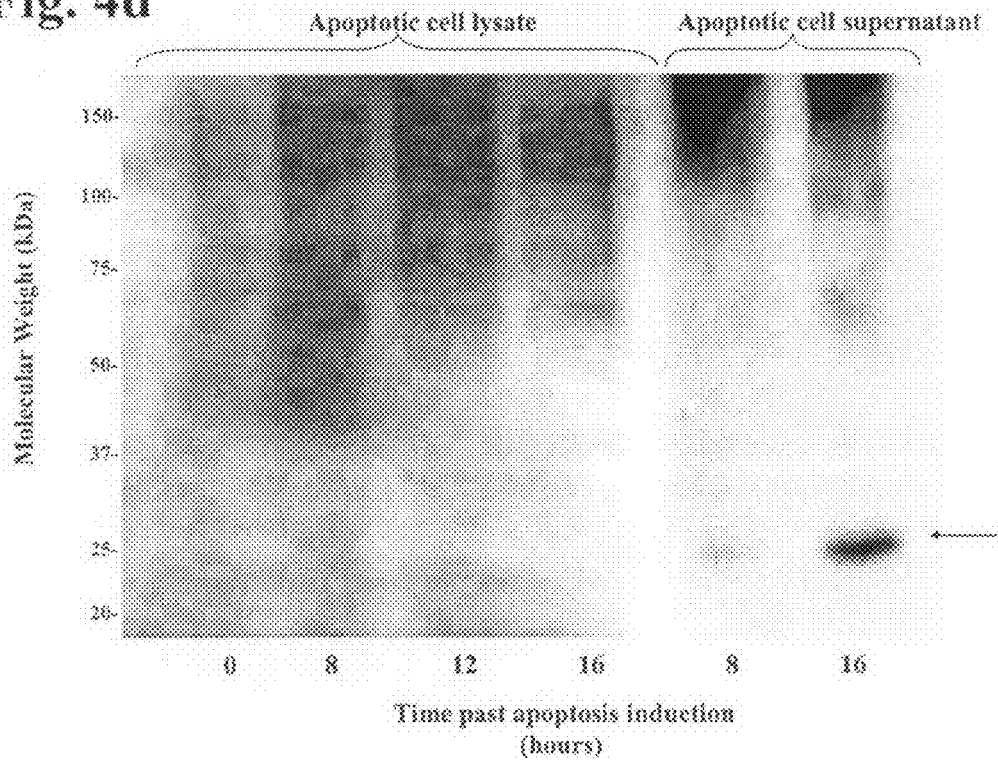

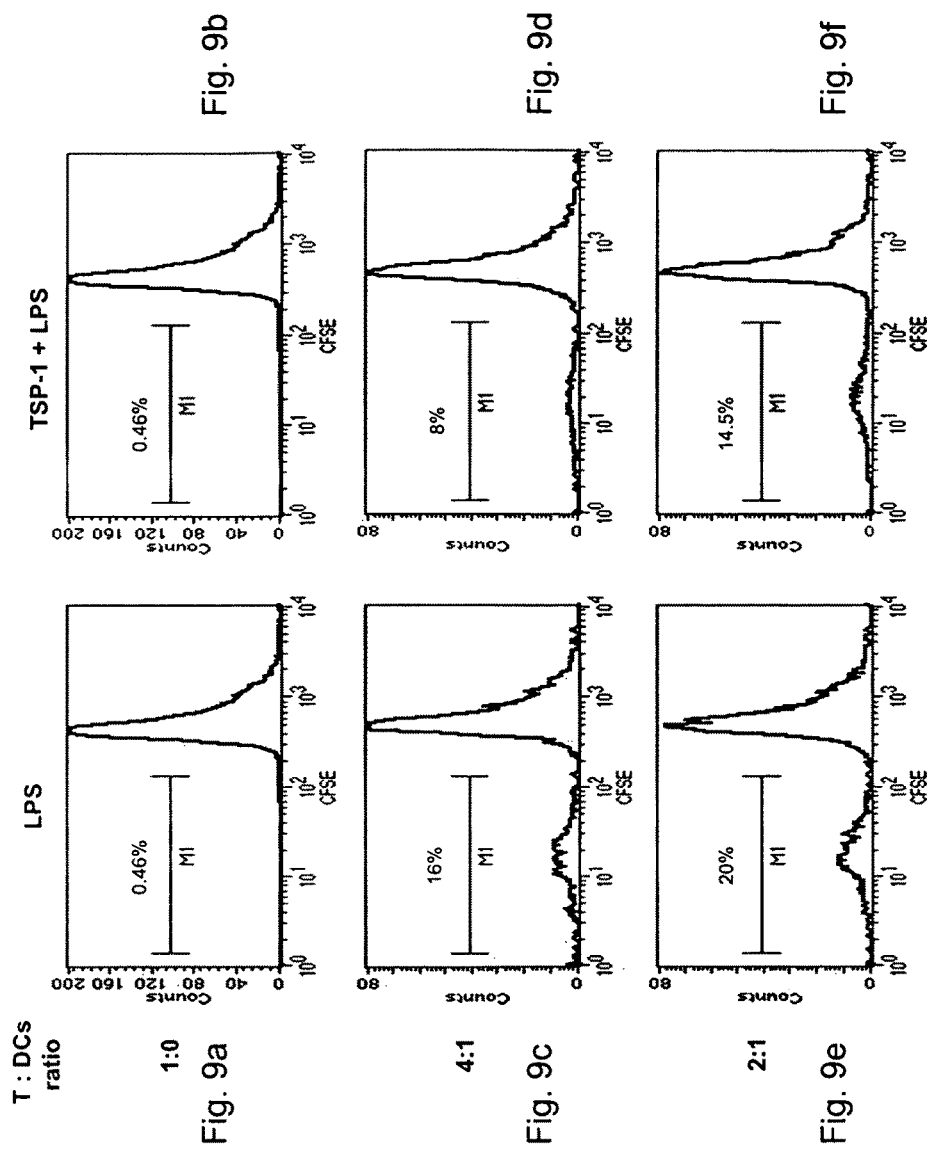

IMMUNE DISEASE MEDICAMENT COMPRISING A MODULATOR OF THE BINDING BETWEEN A HEPARIN BINDING DOMAIN OF THROMBOSPONDIN-1 AND A BETA1 INTEGRIN

RELATED APPLICATIONS

This Application is a National Phase of PCT Patent Application No. PCT/IL2006/000712 having International Filing Date of Jun. 20, 2006, which claims the benefit of U.S. Provisional Patent Application No. 60/691,848 filed on Jun. 20, 2005. The contents of the above Applications are all incorporated herein by reference.

FIELD AND BACKGROUND OF THE INVENTION

The present invention relates to methods of treating immunity-related diseases via modulation of differentiation of immunostimulatory/mature antigen-presenting cells, and further relates to articles of manufacture for practicing such treatment methods. More particularly, the present invention relates to methods of treating diseases characterized by pathological or insufficient immune responses, via modulation of thrombospondin-mediated endocytosis of apoptotic cells by antigen-presenting cells, and further particularly relates to the use of agonists or inhibitors of interactions between thrombospondin and thrombospondin receptors for practicing such disease treatment methods, respectively.

Immunity-related diseases comprise a large number of diseases characterized by significant mortality and morbidity, and for which no satisfactory/optimal treatments are presently available. Such diseases include those characterized by pathological immune responses, such as autoimmune, transplantation-related, inflammatory and alloimmune pregnancy diseases; and those characterized by insufficient immune responses, such as infectious and/or tumoral diseases.

Antigen-presenting cells, such as dendritic cells, play pivotal roles in modulation of immune responses. Under non-inflammatory conditions, immature dendritic cells in peripheral tissues continuously capture innocuous and cell-associated self-antigens and migrate to draining lymph nodes, where they can induce tolerance to such antigens (Steinman, R. M. et al., 2003. Tolerogenic dendritic cells. Annu. Rev. Immunol. 21:685-711). In contrast, under pathological conditions, such as in the presence of pathogens and necrotic cells, dendritic cells undergo a process of maturation involving up-regulation of costimulatory molecules, secretion of proinflammatory cytokines, and acquisition of the capacity stimulate the differentiation of naive T-cells into effector cells. The process of endocytosis of apoptotic cells by antigen-presenting cells, such as dendritic cells and macrophages, has been suggested to play an important role in maintenance of immune homeostasis, via resolution of inflammation, and via induction of peripheral immune tolerance (Savill, 2001; Vandivier et al., 2002; Verbovetski et al., 2002). It has been suggested that apoptotic cells facilitate their endocytosis by generating pro-endocytotic signals to professional phagocytes, and antigen-presenting cells, and that such endocytosis occurs in the absence of inflammatory or autoimmune responses (Voll et al., 1997; Fadok et al., 1998; Huynh et al., 2002; Verbovetski et al., 2002; Savill et al., 2002). Direct pro-endocytotic signals generated by apoptotic cells include alterations in cell surface phospholipid composition (Fadok et al., 1992), changes in cell surface glycoprotein expression, or distinct alterations in cell surface charge (Henson et al., 2001). As well, certain serum proteins can opsonize an apoptotic cell surface and signal phagocytes to endocytose the opsonized apoptotic cells (Mevorach et al., 1998; Mevorach, 1999; Verbovetski et al., 2002), and apoptotic cells can secrete molecules, such as lysophosphatidylcholine, so as to attract phagocytes (Lauber et al., 2003). In contrast to apoptotic cells, viable cells provide signals actively preventing their endocytosis, for example via restriction of phosphatidylserine to the inner leaflet of their membrane, and by surface display of CD31, which is down-regulated upon apoptosis (Brown et al., 2002). The range of mechanisms involved in mediating and regulating identification and clearance of apoptotic cells indicate that such processes are essential for proper maintenance of immune homeostasis.

Thrombospondins are a family of extracellular glycoproteins consisting of five members in vertebrates: thrombospondin (TSP)-1 (TSP-1), thrombospondin-2, thrombospondin-3, thrombospondin-4, and thrombospondin-5/cartilage oligomeric matrix protein. Thrombospondin-1, which is secreted by macrophages and dendritic cells (Savill et al., 1992, Doyen et al., 2003), fibroblasts (Moodley et al., 2003) and other cell types (Adams, 2001), has been implicated in mediating endocytosis of apoptotic cells by antigen-presenting cells (Savill et al., 1992; Moodley et al., 2003; Stern et al., 1996). This molecule is a homotrimeric glycoprotein composed of subunits each having a molecular weight of approximately 145 kilodalton, which was first described as a platelet alpha-granule protein that is released upon activation (Baenziger et al., 1971), and which has been found to mediate numerous cell-matrix and cell-cell activities through a variety of receptors (reviewed by Adams, 2001). Thrombospondin-1 has an N-terminal, heparin-binding domain (HBD) which is cleaved and released upon platelet aggregation (reviewed in Elzie et al., 2004), and which is capable of specifically binding CD29/beta1 integrin, as evidenced by its capacity to specifically bind at least three different beta1 integrins, including alpha3beta1, alpha6beta1, and alpha4beta1 integrins, (Krutzsch, H. C. et al., 1999. J. Biol. Chem. 274:24080-24086; Chandrasekaran, L. et al., 2000. Mol. Biol. Cell 11, 2885-2900; Calzada, M. J. et al., 2003. J. Biol. Chem. 278: 40679-40687). The heparin-binding domain has been suggested to mediate thrombospondin-1-induced angiogenesis (Chandrasekaran, L. et al., 2000. Mol. Biol. Cell 11, 2885-2900), cell adhesion, and cellular chemotaxis (Krutzsch, H. C. et al., 1999. J. Biol. Chem. 274:24080-24086; Calzada, M. J. et al., 2003. J. Biol. Chem. 278:40679-40687), but has not been implicated in regulation of immunostimulatory differentiation/maturation of antigen-presenting cells.

In view of the role of thrombospondin-1 in mediating endocytosis of apoptotic cells by antigen-presenting cells, and in view of the role of such endocytosis in inhibition of differentiation of immunostimulatory/mature antigen-presenting cells a potentially advantageous strategy for treating immunity-related diseases may be to suitably modulate thrombospondin-1-induction of such differentiation.

Various approaches have been proposed in the art for modulating thrombospondin-1-mediated inhibition of differentiation of immunostimulatory/mature antigen-presenting cells.

One approach which has been suggested for stimulating such differentiation involves using thrombospondin-1 at agonistic concentrations of 0.4 to 10 micrograms per milliliter, in an attempt to increase endocytosis of apoptotic neutrophils by macrophages (Savill et al., 1992).

Several prior art approaches have been suggested, as follows, for decreasing/eliminating thrombospondin-1-mediated inhibition of differentiation of immunostimulatory/mature antigen-presenting cells.

One approach involves using soluble thrombospondin-1 at inhibitory/blocking concentrations. This approach has been attempted using thrombospondin-1 at blocking concentrations of 100 micrograms per milliliter, in an attempt to inhibit endocytosis of apoptotic neutrophils by macrophages (Savill et al., 1992).

Another approach involves using anti-thrombospondin-1 antibodies for blocking interactions of thrombospondin-1 with receptors thereof. This approach has been attempted using a monoclonal antibody (A6.1) specific for the EGF repeat motif of thrombospondin-1, in an attempt to inhibit endocytosis of apoptotic neutrophils by macrophages (Savill et al., 1992); a monoclonal antibody (A2.5) specific for the N-terminal domain of thrombospondin-1, in an attempt to inhibit endocytosis of apoptotic neutrophils by macrophages (Savill et al., 1992); or anti-thrombospondin-1 antibody, in an attempt to inhibit endocytosis of apoptotic eosinophils by antigen-presenting cells (Stern et al., 1996).

Yet another approach involves disrupting interactions between thrombospondin-1 and the thrombospondin-1 receptor CD36, a ligand of the internal/non-N-terminal type 1 repeats of thrombospondin-1. This approach has been attempted using blocking antibodies specific for CD36, in an attempt to inhibit endocytosis of apoptotic neutrophils (Savill et al., 1992), eosinophils (Stern et al., 1996) or fibroblasts (Moodley et al., 2003) by macrophages; administering antibodies specific for CD36, in an attempt to inhibit LPS-induced dendritic cell maturation, as determined via inhibition of T-cell activation and pro-inflammatory cytokine production (Urban B C. et al., 2001. Proc. Natl. Acad. Sci. U.S.A. 98:8750-8755); or by administering a monoclonal antibody (A4.1) specific for the CD36-binding central stalk-like region of thrombospondin-1 (type 1 repeats), in an attempt to inhibit endocytosis of apoptotic fibroblasts by macrophages (Moodley et al., 2003).

Still another approach involves disrupting the interaction between thrombospondin-1 and CD47, a thrombospondin-1 receptor binding the C-terminal portion of thrombospondin-1. This approach has been tried using blocking antibodies specific for CD47, in an attempt to inhibit bacteria-induced dendritic cell maturation, as determined via inhibition of pro-inflammatory cytokine production (Demeure C E. et al., 2000. J Immunol. 164:2193; Doyen et al., 2003); or using a monoclonal antibody (C6.7) specific for the extreme C-terminus of thrombospondin-1, in an attempt to inhibit endocytosis of apoptotic neutrophils by macrophages (Savill et al., 1992), or immunosuppressive cytokine production by dendritic cells (Doyen et al., 2003).

A further approach involves disrupting specific interactions between C-terminal RGD repeats of thrombospondin-1 and alphaVbeta3 integrin. This approach has been attempted using blocking antibodies specific for CD51/alphaV integrin, in an attempt to inhibit LPS-induced dendritic cell maturation, as determined via inhibition of T-cell activation and pro-inflammatory cytokine production (Urban B C. et al., 2001. Proc. Natl. Acad. Sci. U.S.A. 98:8750-8755); by administering a monoclonal antibody specific for integrin alphaVbeta3, a potential thrombospondin-1 receptor, in an attempt to inhibit endocytosis of apoptotic eosinophils (Stern et al., 1996) or apoptotic fibroblasts (Moodley et al., 2003) by macrophages; or by inducing down-regulation of surface-display of alphaVbeta3 integrin in macrophages, in an attempt to inhibit endocytosis of apoptotic neutrophils (Savill et al., 1992).

An additional approach involves exposing antigen-presenting cells to compounds, such as RGDS peptide or heparin, capable of binding the heparin-binding domain (Beppu R. et al., 2001. Immunol Invest. 30:143-56).

However, the prior art approaches for modulating thrombospondin-1-mediated inhibition of differentiation of immunostimulatory/mature dendritic cells suffer from various critical drawbacks, including: not having been tested in-vivo; not having been investigated using dendritic cells, the antigen-presenting cell type having the most potent immunomodulatory capacity; resulting in induction of both immunostimulatory and immunosuppressive differentiation; being ineffective or suboptimally effective; and/or, having failed to demonstrate any capacity to modulate differentiation of immunostimulatory/mature antigen-presenting cells, such as with respect to surface expression of costimulatory molecules.

Critically, no prior art approach has demonstrated any therapeutic capacity.

Thus, all prior art approaches have failed to provide an adequate solution for treating immunity-related diseases by suitably modulating thrombospondin-1-mediated inhibition of differentiation of immunostimulatory/mature antigen-presenting cells.

There is thus a widely recognized need for, and it would be highly advantageous to have, novel and effective methods ands medicaments for treating immunity-related diseases devoid of the above limitation.

SUMMARY OF THE INVENTION

The present invention discloses the novel use of agonists and inhibitors of interactions between thrombospondin and thrombospondin receptors for treating immunity-related diseases characterized by pathological or insufficient immune responses, respectively. This use can be effected in a variety of ways as further described and exemplified hereinbelow.

According to one aspect of the present invention, there is provided an article of manufacture comprising packaging material and a pharmaceutical composition, the article of manufacture being identified in print in or on the packaging material for treatment of an immunity-related disease in a subject in need thereof, wherein the pharmaceutical composition comprises a pharmaceutically acceptable carrier and, as an active ingredient, a compound being capable of modulating an interaction between a heparin-binding domain of a thrombospondin and a receptor of the heparin-binding domain.

According to another aspect of the present invention, there is provided an article of manufacture comprising packaging material and a pharmaceutical composition, the article of manufacture being identified in print in or on the packaging material for treatment of a disease characterized by a pathological immune response in a subject in need thereof, wherein the pharmaceutical composition comprises a pharmaceutically acceptable carrier and, as an active ingredient, a heparin-binding domain of a thrombospondin, the heparin-binding domain being in a substantially isolated state.

According to yet another aspect of the present invention, there is provided an article of manufacture comprising packaging material and a pharmaceutical composition, the article of manufacture being identified in print in or on the packaging material for treatment of a disease characterized by an insufficient immune response in a subject in need thereof, wherein the pharmaceutical composition comprises a pharmaceutically acceptable carrier and, as one or more active ingredients: (i) a ligand of a heparin-binding domain of a thrombospondin; and/or (ii) a ligand of a receptor of the heparin-binding domain.

According to further features in preferred embodiments of the invention described below, the compound comprises an agonist of the interaction, wherein the agonist is: (i) the heparin-binding domain, wherein the heparin-binding domain is in a substantially isolated state; or (ii) is a mimetic of the heparin-binding domain.

According to still further features in the described preferred embodiments, the compound comprises an inhibitor of the interaction, wherein the inhibitor is a ligand of the heparin-binding domain and/or is a ligand of the receptor.

According to a further aspect of the present invention there is provided a method of treating an immunity-related disease in a subject in need thereof, the method comprising modulating in the subject an interaction between a heparin-binding domain of a thrombospondin and a receptor of the heparin-binding domain, thereby regulating an immune response for treating the immunity-related disease in the subject.

According to yet a further aspect of the present invention there is provided a method of treating a disease characterized by a pathological immune response in a subject in need thereof, the method comprising administering to the subject a substantially isolated heparin-binding domain of a thrombospondin, thereby regulating an immune response for treating the disease in the subject.

According to still a further aspect of the present invention there is provided a to method of treating a disease characterized by an insufficient immune response in a subject in need thereof, the method comprising administering to the subject a ligand of a heparin-binding domain of a thrombospondin, and/or a ligand of a receptor of said heparin-binding domain, thereby regulating an immune response for treating the disease in the subject.

According to further features in preferred embodiments of the invention described below, the disease is characterized by a pathological immune response, and the modulating of the interaction comprises inducing or increasing the interaction.

According to still further features in the described preferred embodiments, the disease is characterized by an insufficient immune response, and the modulating of the interaction comprises preventing, decreasing or eliminating the interaction.

According to still further features in the described preferred embodiments, the disease is selected from the group consisting of an autoimmune disease, a transplantation-related disease, an inflammatory disease, an alloimmune pregnancy disease, a cardiovascular autoimmune disease, a connective tissue autoimmune disease, a gastrointestinal autoimmune disease, a glandular autoimmune disease, a gonadal autoimmune disease, a hematological autoimmune disease, a hepatic autoimmune disease, a mammary autoimmune disease, a muscular autoimmune disease, a neurological autoimmune disease, an ocular autoimmune disease, an oropharyngeal autoimmune disease, a pancreatic autoimmune disease, a pulmonary autoimmune disease, a renal autoimmune disease, a reproductive organ autoimmune disease, a rheumatoid autoimmune disease, a skin autoimmune disease, a systemic autoimmune disease, a thyroid autoimmune disease, graft-versus-host disease, allograft rejection, an acute inflammatory disease, anaphylactic shock, atherosclerosis, cachexia, a chronic inflammatory disease, an episodic inflammatory disease, gangrene, idiopathic inflammation a mechanical injury-associated inflammation, a menstruation-related inflammation, a musculo-skeletal inflammation, a myocardial infarction, a neurodegenerative disease, a prosthetic implant-related inflammation, restenosis following percutaneous transluminal coronary angioplasty (PTCA), septic shock, stroke, toxic shock syndrome, a transient inflammatory disease, thrombosis, an ulcer, and a vascular stent-related inflammation.

According to still further features in the described preferred embodiments, the disease is selected from the group consisting of an infectious disease, a tumoral disease, an adenoma, a blastoma, a benign tumor, a bone tumor, a brain tumor, a carcinoma, a cardiovascular tumor, a connective tissue tumor, a gastrointestinal tumor, a glandular tumor, a glioma, a gonadal tumor, a head and neck tumor, a hematological tumor, a hepatic tumor, a lymphoid tumor, a malignant tumor, a mammary tumor, a muscle tumor, a neurological tumor, an ocular tumor, a pancreatic tumor, a polyp, a pulmonary tumor, a renal tumor, a reproductive organ tumor, a sarcoma, a skin tumor, a thyroid tumor, a wart, a bacterial infection, a fungal infection, a mycoplasma infection, a protozoan infection, and a viral infection.

According to an additional aspect of the present invention there is provided a method of regulating an immune response in a subject in need thereof, the method comprising modulating in the subject an interaction between a heparin-binding domain of a thrombospondin and a receptor of the heparin-binding domain, thereby regulating the immune response in the subject.

According to further features in preferred embodiments of the invention described below, the thrombospondin is thrombospondin-1.

According to still further features in the described preferred embodiments, the heparin-binding domain comprises an amino acid sequence which is at least 70 percent similar to the amino acid sequence set forth by SEQ ID NO: 5, as determined using the Standard protein-protein BLAST [blastp] software of the NCBI.

According to still further features in the described preferred embodiments, the receptor comprises a beta1 integrin.

According to still further features in the described preferred embodiments, regulating the immune response comprises preventing, decreasing or eliminating the immune response, and the modulating of the interaction comprises inducing or increasing the interaction.

According to still further features in the described preferred embodiments, inducing or increasing the interaction comprises administering to the subject a compound which comprises an agonist of the interaction, wherein the agonist is the heparin-binding domain and/or is a mimetic of the heparin-binding domain.

According to still further features in the described preferred embodiments, regulating the immune response comprises inducing and/or increasing the immune response, and the modulating of the interaction comprises preventing, decreasing or eliminating the interaction.

According to still further features in the described preferred embodiments, preventing, decreasing or eliminating the interaction comprises administering to the subject a compound which comprises an inhibitor of the interaction, wherein the inhibitor is a ligand of the heparin-binding domain and/or is a ligand of the receptor.

According to still further features in the described preferred embodiments, the ligand of the heparin-binding domain is selected from the group consisting of an antibody or antibody fragment, at least a portion of the receptor, and a mimetic of the at least a portion of the receptor.

According to still further features in the described preferred embodiments, the ligand of the receptor is an antibody or antibody fragment.

The present invention successfully addresses the shortcomings of the presently known configurations by providing novel medicaments and methods for effectively treating immunity-related diseases such as autoimmune, transplantation-related, inflammatory, alloimmune pregnancy, infectious and/or tumoral diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a set of FACS dot-plots depicting efficient induction of monocyte apoptosis by serum-withdrawal treatment. More than 70 percent of monocytes were shown to be annexin V-positive and propidium iodide (PI)-negative after 12 hours of serum-withdrawal treatment, identifying them as cells in early apoptosis. Secondary necrotic cells represented at most 5 percent of the treated cells as indicated by annexin V-positive, propidium iodide-positive cells. The specificity of the apoptotic process was further shown by marked inhibition of apoptosis in the presence of 20 millimolar zVAD-fmk. Each dot-plot represents viable cells (lower left quadrant), early apoptotic cells (right lower quadrant), and secondary necrotic cells (upper right quadrant). Data is representative of six different experiments. The percentage of viable, early apoptotic and secondary necrotic cells is indicated within each quadrant.

FIGS. 4b-c are RT-PCR assay results showing that thrombospondin-1 mRNA is transcribed upon monocyte apoptosis. Total mRNA was extracted from 10 million monocytes at different times following induction of apoptosis by serum-withdrawal treatment, and was reverse-transcribed and enhanced by polymerase chain reaction. Thrombospondin-1 mRNA and beta-actin mRNA were enhanced by PCR using specific primers, and their relative abundance was measured by ethidium bromide photospectrometry. Viable monocytes (0 hours) had very low levels of thrombospondin-1, which increased as apoptosis progressed. mRNA was not detected in immature dendritic cells and mature dendritic cells (FIG. 4b). Abundance ratios of thrombospondin-1 and beta-actin mRNAs, as measured by densitometry, show peak levels at 9.5 hours, in accordance with maximal state of early monocyte apoptosis (FIG. 4c).

FIG. 4d is an autoradiograph of a Western immunoblotting assay depicting that the N-terminal heparin-binding domain of thrombospondin-1 appears exclusively in the extracellular milieu of apoptotic monocytes. Protein from 30 million lysed apoptotic monocytes (left) or from culture medium of 30 million apoptotic monocytes (right) was separated by SDS-PAGE, analyzed using mouse anti-human triclonal thrombospondin-1 antibody (Neomarkers) and developed via enhanced chemiluminescence assay (ECL). A 26 kilodalton fragment (arrow) is found only in the culture supernatant. Protein species having a size of 130 kDa and higher present within the apoptotic cells represent glycosylated forms of thrombospondin-1 monomers.

FIG. 6a is a FACS dot-plot depicting that thrombospondin-1 binds weakly to apoptotic monocytes. Double staining with PE-conjugated anti-thrombospondin-1 antibody and FITC-conjugated annexin-V is shown. Only 28 percent (18/64) of annexin-V-positive monocytes were thrombospondin-1 positive. Numbers indicate percentages of cells included in the respective quadrants. FIG. 6b is a FACS dot-plot depicting that thrombospondin-1 binds monocyte in late rather than early apoptotic phase. Double staining with FITC-conjugated anti-TSP-1 antibody and propidium iodide is shown. Almost all monocytes that bind anti-thrombospondin-1, are propidium iodide-positive late apoptotic cells. This is true also for the small fraction of propidium iodide-positive cells that are included in viable cells. FIG. 6c is a FACS histogram depicting that thrombospondin-1 binds viable immature dendritic cells. Thrombospondin-1-bound immature dendritic cells (black trace), and all cells show binding (gray-filled curve) compared to isotype control. Five percent of immature dendritic cells were annexin-V positive and less than 1 percent were propidium iodide-positive, excluding binding due to apoptosis.

FIG. 6d depicts thrombospondin-1 structural and functional domains that are relevant to apoptotic cell clearance. The relevant receptors are indicated. FIG. 6e depicts mechanisms of thrombospondin-1 as a bridging molecule. Thrombospondin-1 may be generated by phagocytes (i) or by apoptotic cells that also can secrete the N-terminal domain (ii). Whether the source is the endocytosing cell or the apoptotic cell, thrombospondin-1 or the N-terminal domain serve as a bridge between apoptotic cells and phagocytes. FIG. 6c depicts an alternative mechanism (no bridge); thrombospondin-1 or the N-terminal domain bind to immature dendritic cells and induce ameliorated endocytosis and immune suppression, even in the absence of attached apoptotic cells (see FIG. 7).

FIG. 8b) and CD86 (FIG. 8c) was indicative of the level of dendritic cell maturation. Dendritic cells were treated with inhibitory antibodies as described above, and were then treated with thrombospondin-1 concomitantly with (gray bars) or without (black bars) interaction with apoptotic monocytes. Four hours later, 5 nanograms per milliliter LPS was added and surface display of HLA-DR and CD86 was examined 24 hours later. All of the targeted molecules showed loss of inhibitory effect when antibodies directed against them were used, relative to isotype controls. The main effect was achieved by blocking heparin-binding domain (p less than 0.0001), but receptors, such as CD36, CD29/beta1 integrin, CD51/alphaV integrin, and CD47, had an important effect on immunostimulatory differentiation/maturation (p less than 0.0001 for each site). The relative inhibitory effect on maturation is expressed as the relative change in FITC-conjugated anti-HLA-DR or FITC-conjugated anti-CD86 antibody median fluorescence of dendritic cells, compared to dendritic cells treated with isotype control and treated with LPS. Data shown is from one representative experiment out of three.

FIGS. 9a-f are FACS histograms depicting DCs induced T cell activation. CFSE labeled T cells were co-cultured with different ratios of DCs which were treated with either LPS alone (FIGS. 9a, c, e) or which were exposed to TSP1 for 5 hour prior to LPS treatment (FIGS. 9b, d, f). M1 depicts the fraction of CD3 positive CFSE labeled cells. Exposure to TSP1 prior LPS treatment inhibited DCs induced T cells activation by 27% at the 2:1 ratio between T cell and DC (T:DCs) (FIGS. 9e-f) and by 50% at the 4:1 ratio between T cell and DC ratio (FIGS. 9c-d). Thus, these results demonstrate that TSP-1, by itself, inhibits T-cell activation.

DESCRIPTION OF THE PREFERRED EMBODIMENTS

Figure 2A:
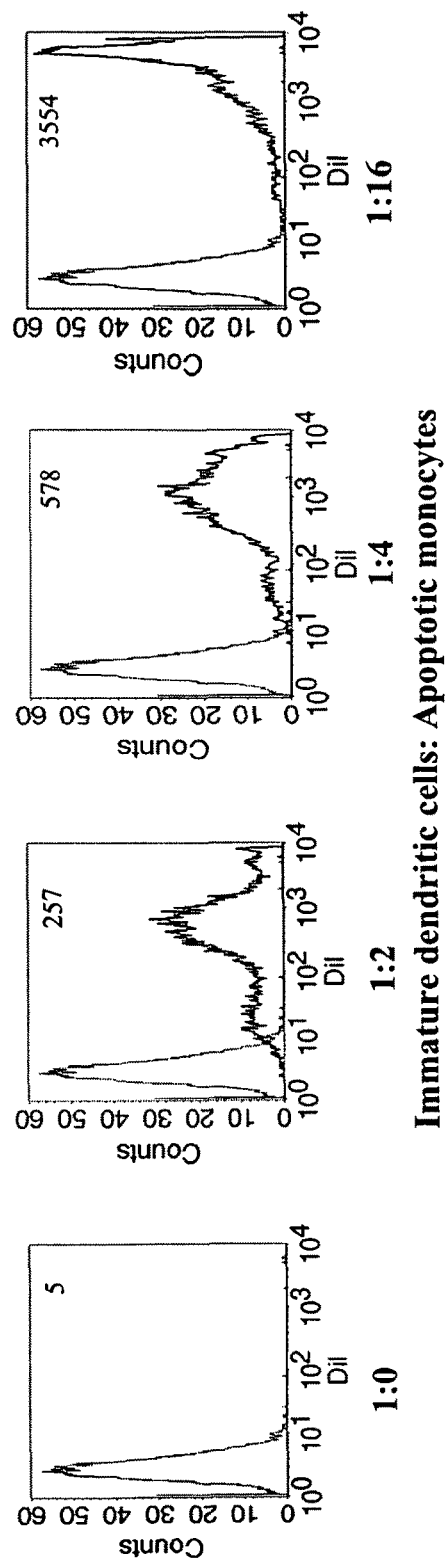
FIG. 2a is a set of FACS histograms depicting endocytosis of DiI-stained apoptotic monocytes by immature dendritic cells. DiI-stained monocytes were interacted with immature dendritic cells at the indicated ratios. Immature dendritic cells acquired DiI following interaction with DiI-stained apoptotic monocytes (bold trace). Median fluorescence is indicated in each histogram.

The present invention is of methods of regulating an immune response in a subject in need thereof, of methods of treating an immunity-related disease in a subject in need thereof; and of medicaments for use in such treatment. Specifically, the present invention can be used to regulate in a subject, with optimal effectiveness relative to the prior art, thrombospondin (TSP)-mediated inhibition of differentiation of immunostimulatory/mature antigen-presenting cells. As such, the present invention can be used for effectively treating immunity-related diseases, including diseases characterized by a pathological immune response, such as autoimmune, transplantation-related, inflammatory and alloimmune pregnancy diseases; and including diseases characterized by insufficient immune responses, such as infectious and/or tumoral diseases.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Immunity-related diseases, which include diseases characterized by insufficient or pathological immune responses, comprise numerous debilitating/lethal diseases for which no satisfactory/optimal treatment is available. In view of the role of thrombospondin-1 in mediating endocytosis of apoptotic cells by antigen-presenting cells, and in view of the role of such endocytosis in mediating inhibition of differentiation of immunostimulatory/mature antigen-presenting cells, a potentially optimal strategy for treatment of immunity-related diseases may be via modulation of thrombospondin-1-mediated inhibition of differentiation of immunostimulatory/mature antigen-presenting cells.

Various approaches for modulating thrombospondin-1-mediated inhibition of differentiation of immunostimulatory/mature antigen-presenting cells have been described by the prior art.

One approach for inducing/increasing thrombospondin-1-mediated inhibition of differentiation of immunostimulatory/mature antigen-presenting cells involves exposing the cells to thrombospondin-1 at agonistic concentrations of 0.4 to 10 micrograms per milliliter (Savill et al., 1992).

Several prior art approaches have been suggested, as follows, for decreasing or eliminating such inhibition of differentiation of immunostimulatory/mature antigen-presenting cells. One approach involves using thrombospondin-1 at local concentrations of 100 micrograms per milliliter (Savill et al., 1992). Another approach involves using anti-thrombospondin-1 antibodies capable of blocking interaction of thrombospondin-1 with receptors thereof, such as: monoclonal antibody (A6.1) specific for the EGF repeat motif of thrombospondin-1, (Savill et al., 1992); monoclonal antibody (A2.5) specific for the N-terminal domain of thrombospondin-1 (Savill et al., 1992); or anti-thrombospondin-1 antibody (Stern et al., 1996). Yet another approach involves disrupting interactions between thrombospondin-1 and the thrombospondin-1 receptor CD36, a ligand of the central type 1 repeats of thrombospondin-1 (Savill et al., 1992; Stern et al., 1996; Moodley et al., 2003; Urban B C. et al., 2001. Proc. Natl. Acad. Sci. U.S.A. 98:8750-8755; Moodley et al., 2003). Still another approach involves disrupting the interaction between thrombospondin-1, via its C-terminal domain, and the thrombospondin-1 receptor CD47 (Demeure C E. et al., 2000. J Immunol. 164:2193; Doyen et al., 2003; Savill et al., 1992). A further approach involves disrupting interactions between thrombospondin-1 and alphaVbeta3 integrin, a thrombospondin-1 receptor binding C-terminal RGD repeats of thrombospondin-1 (Urban B C. et al., 2001. Proc. Natl. Acad. Sci. U.S.A. 98:8750-8755; Stern et al., 1996; Moodley et al., 2003; Savill et al., 1992). An additional approach involves exposing the antigen-presenting cells to heparin-binding domain-binding compounds, such as RGDS peptide or heparin (Beppu R. et al., 2001. Immunol Invest. 30:143-56).

However, prior art approaches for modulating thrombospondin-1-mediated inhibition of differentiation of immunostimulatory/mature antigen-presenting cells suffer from numerous critical drawbacks, including: not having been tested in-vivo; not having been investigated using dendritic cells, the antigen-presenting cell type having the most potent immunomodulatory capacity; mediation of both immunostimulatory and immunosuppressive differentiation; being ineffective/suboptimally effective; and/or having failed to demonstrate any capacity to modulate inhibition of differentiation of immunostimulatory/mature antigen-presenting cells, such as with respect to modulation of surface expression of costimulatory molecules.

Critically, no prior art approach has demonstrated any therapeutic capacity.

Thus, all prior art approaches have failed to provide satisfactory means of modulating thrombospondin-1-mediated inhibition of differentiation of immunostimulatory/mature antigen-presenting cells so as to enable treatment of an immunity-related disease.

While reducing the present invention to practice, as is described and illustrated in Examples 1 and 2 of the Examples section below, it was uncovered that endocytosis of apoptotic human monocytes by human dendritic cells inhibits immunostimulatory differentiation/maturation of the latter, that such apoptotic cells secrete cleaved heparin-binding domain (HBD) of thrombospondin-1, and that blocking antibodies specific for the heparin-binding domain optimally inhibit endocytosis of such apoptotic cells by such dendritic cells. As such, it was uncovered for the first time that an isolated heparin-binding domain of a thrombospondin can be used to inhibit differentiation of immunostimulatory/mature antigen-presenting cells. While further reducing the present invention to practice, it was uncovered for the first time that blocking antibody specific for either the heparin-binding domain, or the thrombospondin-1 receptor CD29/integrin beta1, which specifically binds thrombospondin-1 via its heparin-binding domain, can be used to optimally promote differentiation of human immunostimulatory/mature dendritic cells. As such, it was further uncovered for the first time that inhibiting the interaction between a heparin-binding domain of a thrombospondin and CD29/integrin beta1 can be used to optimally promote differentiation of immunostimulatory/mature antigen-presenting cells.

Therefore, by virtue of enabling optimal modulation of thrombospondin-1-mediated inhibition of differentiation of immunostimulatory/mature antigen-presenting cells, the present invention can be used for effectively controlling immune responses, and thereby for effectively treating immunity-related diseases.

Thus, according to one aspect of the present invention there is provided a method of regulating an immune response in a subject in need thereof. The method is effected by regulating in the subject an interaction between a heparin-binding domain of a thrombospondin and a receptor of the heparin-binding domain.

As used herein, the term "immune response", when relating to the method of regulating an immune response of the present invention, refers to any desired or undesired immune response, and includes an antigen-specific immune response, a non-antigen-specific immune response, a systemic immune response, an inflammatory immune response, and an immune response mediated by any combination of cell types and/or soluble molecules.

As is generally described and illustrated in Example 1 of the Examples section which follows, suitably regulating an interaction between a heparin-binding domain of a thrombospondin and a receptor of a heparin-binding domain of a thrombospondin can be used to modulate differentiation of immunostimulatory/mature antigen-presenting cells. It will be appreciated that, as such, the present invention can be used to modulate an immune response in a subject having an immunity-related disease in such a way so as to effectively treat the disease in the subject.

Thus, according to this aspect of the present invention, there is provided a method of treating an immunity-related disease in a subject in need thereof.

As used herein, the term "treating," when relating to a disease of the present invention, refers to curing the disease, reversing progression of the disease and/or of a symptom thereof, halting progression of the disease and/or a symptom thereof, slowing progression of the disease and/or a symptom thereof, alleviating the disease and/or a symptom thereof, palliating the disease, preventing or delaying onset of the disease and/or a symptom thereof, and/or ameliorating the disease and/or a symptom thereof.

As used herein, the phrase "subject in need thereof", refers to a subject which has a disease of the present invention, and/or which is susceptible to having a disease of the present invention in the future.

As used herein, the term "disease" refers to any medical disease, disorder, condition, or syndrome; or to any undesired and/or abnormal physiological morphological, cosmetic and/or physical state and/or condition.

As is particularly described and illustrated in Example 1 of the Examples section which follows (refer, for example, to FIGS. 8*b-c*), downregulating an interaction between a heparin-binding domain of a thrombospondin and a receptor of the heparin-binding domain in antigen-presenting cells, such as human dendritic cells, can be used for promoting immunostimulatory differentiation/maturation of such cells, as clearly and convincingly evidenced by inhibition of cell surface display of major dendritic cell maturation/immunostimulatory markers, such as the haplotype molecule HLA-DR; and CD86/B7-2, an agonistic ligand of CD28, the major T-cell co-stimulatory receptor essential for T-cell activation. As such, it will be appreciated that the present invention can be used for stimulating a therapeutic immune response in a subject so as achieve treatment in the subject of a disease characterized by a pathological lack or insufficiency of such an immune response.

As used herein, the term "downregulating", when relating to the interaction between the heparin-binding domain and the receptor of the heparin-binding domain, refers to preventing, decreasing or eliminating the interaction.

As used herein, the term "promoting", when relating to differentiation of immunostimulatory/mature antigen-presenting cells, refers to inducing or increasing such differentiation.

As used herein, the term "stimulating", when relating to an immune response of the present invention, refers to inducing or increasing the immune response.

Thus, the present invention provides a method of treating a disease characterized by an insufficient immune response.

As is further described hereinbelow, diseases characterized by insufficient immune responses which can be treated according to teachings of the present invention include, but are not limited to, infectious and/or tumoral diseases.

According to teachings of the present invention, treating a disease characterized by an insufficient immune response is achieved by downregulating in the subject an interaction between a heparin-binding domain of the present invention and a receptor of the present invention. Suitable ways to achieve such downregulation are described hereinbelow.

As is further particularly described and illustrated in Example 1 of the Examples section which follows, upregulating an interaction between a heparin-binding domain of a thrombospondin and a receptor of the heparin-binding domain can be used for inhibiting differentiation of immunostimulatory/mature antigen-presenting cells, such as dendritic cells. As such, it will be appreciated that the present invention can be used for suppressing a pathological immune response in a subject in need thereof, so as to treat in the subject a disease characterized by such a pathological immune response.

As used herein, the term "upregulating", when relating to an interaction between a heparin-binding domain of the present invention and a receptor of the present invention, refers to inducing or increasing such an interaction.

As used herein, the term "inhibiting", when relating to differentiation of immunostimulatory/mature antigen-presenting cells, such as dendritic cells, refers to preventing, decreasing or eliminating such differentiation.

As used herein, the term "suppressing", when relating to an immune response of the present invention, refers to preventing, decreasing or eliminating the immune response.

As is further described hereinbelow, diseases characterized by pathological immune responses which can be treated according to teachings of the present invention include, but are not limited to, autoimmune, transplantation-related, inflammatory, and alloimmune pregnancy diseases.

Thus, the present invention provides a method of treating a disease characterized by a pathological immune response.

According to teachings of the present invention, treating the disease characterized by the pathological immune response in the subject is achieved by upregulating in the subject the interaction between the heparin-binding domain and the heparin-binding domain receptor. Suitable ways to achieve such upregulation are described hereinbelow.

The method of the present invention may be practiced by modulating in the subject an interaction between various types of heparin-binding domains and various types of heparin-binding domain receptors.

As used herein, the phrase "receptor of a heparin-binding domain" refers to a molecular entity which is capable of specifically binding the heparin-binding domain when the heparin-binding domain is in an isolated, free or cleaved state, and/or when the heparin-binding domain is comprised in a substantially intact thrombospondin molecule.

The heparin-binding domain may be that of any one of various types of thrombospondins or thrombospondin-like molecules. Thrombospondins are a known family of extracellular glycoproteins consisting of five members in vertebrates.

According to the teachings of the present invention, the heparin-binding domain is a heparin-binding domain of thrombospondin-1.

Preferably, the heparin-binding domain comprises an amino acid sequence having a percent similarity to the amino acid sequence set forth by SEQ ID NO: 5, as determined using the Standard protein-protein BLAST [blastp] software of the NCBI, of at least 70 percent, more preferably at least 75 percent, more preferably at least 80 percent, more preferably at least 85 percent, more preferably at least 90 percent, more preferably at least 95 percent, more preferably at least 96 percent, more preferably at least 97 percent, more preferably at least 98 percent, more preferably at least 99 percent, and more preferably at least 100 percent.

The heparin-binding domain may comprise an amino acid sequence having a percent identity to the amino acid sequence set forth by SEQ ID NO: 5, as determined using the Standard protein-protein BLAST [blastp] software of the NCBI, of at least 70 percent, more preferably at least 75 percent, more preferably at least 80 percent, more preferably at least 85 percent, more preferably at least 90 percent, more preferably at least 95 percent, more preferably at least 96 percent, more preferably at least 97 percent, more preferably at least 98 percent, and more preferably at least 99 percent.

Preferably, the heparin-binding domain comprises amino acids 1-232 as set forth in SEQ ID NO:5, more preferably, the heparin-binding domain comprises amino acids 19-224 as set forth in SEQ ID NO:5, more preferably, amino acids 24-224 as set forth in SEQ ID NO:5. It will be appreciated that the amino acid sequence set forth by SEQ ID NO: 5 corresponds to the amino acid sequence of heparin-binding domain of human thrombospondin-1 as set forth by SEQ ID NO:6.

Alternately, the heparin-binding domain may be that of thrombospondin-2, thrombospondin-3, thrombospondin-4, or thrombospondin-5. It will be appreciated that the heparin-binding domain may be any of these thrombospondins in view of the significant relevant ligand-binding and functional similarities between heparin-binding domains of different thrombospondins, as exemplified by the relevant similarities between thrombospondin-1 and thrombospondin-2 with respect to CD29/beta1 integrin receptor binding (Calzada M J. et al., 2003. Recognition of the N-terminal modules of thrombospondin-1 and thrombospondin-2 by alpha6beta1 integrin. J Biol Chem. 278:40679-87). As described hereinbelow, CD29/beta1 integrin is a preferred receptor of embodiments of the present invention.

It will be appreciated that the teaching of the present invention whereby regulating an interaction between a heparin-binding domain of a thrombospondin and a receptor of the present invention is used to regulate immunity is clearly novel and non-obvious relative to the prior art since, for example, at the time of the invention the thrombospondin-1 heparin-binding domain was only thought to be involved in mediating cell adhesion, cell motility, thrombospondin endocytosis, or angiogenesis (Elzie et al., 2004; Krutzsch, H. C. et al., 1999. J. Biol. Chem. 274:24080-24086; Calzada, M. J. et al., 2003. J. Biol. Chem. 278:40679-40687; Chandrasekaran, L. et al., 2000. Mol. Biol. Cell 11, 2885-2900).

According to the teachings of the present invention the receptor of the heparin-binding domain preferably comprises a beta1 integrin (also referred to in the art as CD29).

Examples of receptors of heparin-binding domains of thrombospondins, such as a heparin-binding domain of thrombospondin-1, which comprise a beta1 integrin include alpha3beta1 integrin, alpha6beta1 integrin, and alpha4beta1 integrin, (Krutzsch, H. C. et al., 1999. J. Biol. Chem. 274: 24080-24086; Chandrasekaran, L. et al., 2000. Mol. Biol. Cell 11, 2885-2900; Calzada, M. J. et al., 2003. J. Biol. Chem. 278:40679-40687).

Alternately, the receptor may be CD91 (also termed: alpha-2-macroglobulin receptor, α-2M-R, or LRP) or calreticulin, which have been shown to interact with the thrombospondin heparin-binding domain, which are related to apoptotic cell clearance in both mammals (Ogden et al., 2001). The receptor may be syndecan (Naganuma H. et al., 2004. Quantification of thrombospondin-1 secretion and expression of alphav-beta3 and alpha3beta1 integrins and syndecan-1 as cell-surface receptors for thrombospondin-1 in malignant glioma cells. J Neurooncol. 70:309-17; Ferrari do Outeiro-Bernstein M A. et al., 2002. A recombinant NH(2)-terminal heparin-binding domain of the adhesive glycoprotein, thrombospondin-1, promotes endothelial tube formation and cell survival: a possible role for syndecan-4 proteoglycan. Matrix Biol. 21:311-24; Adams J C. et al., 2001. A role for syndecan-1 in coupling fascin spike formation by thrombospondin-1. J Cell Biol. 152:1169-82; Corless C L. et al., 1992. Colocalization of thrombospondin and syndecan during murine development. Dev Dyn. 193:346-58).

Preferably, regulating the interaction according to the teachings of the present invention is effected whereby the receptor is expressed by, and/or is displayed at the surface of, antigen presenting cells, preferably dendritic cells, so as to modulate the immunostimulatory differentiation/maturation of such cells, to thereby achieve a desired immune regulation mediated via such cells.

Figure 8A:
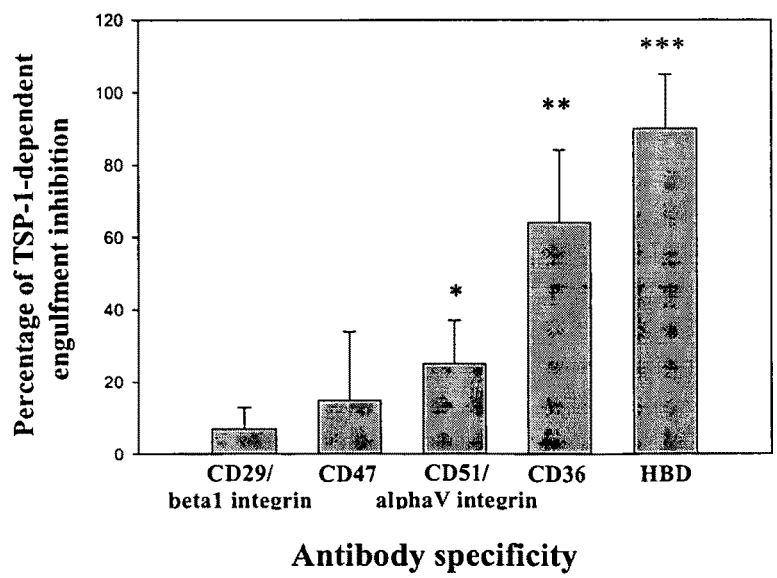
FIG. 8a is a histogram depicting that interaction of heparin-binding domain with CD36 and CD51/alphaV integrin mediates endocytosis in apoptotic monocytes. Immature dendritic cells were treated with several antibodies directed against the heparin-binding domain or against one of various thrombospondin-1 receptors, washed, and then interacted with DiI-stained apoptotic monocytes in the presence of 2 micrograms per milliliter thrombospondin-1. Striking (90 percent) inhibition of apoptotic monocyte endocytosis is seen upon inhibition of binding through heparin-binding domain (p less than 0.0001). Significant inhibition of endocytosis is seen upon inhibition of CD36 (64 percent, p less than 0.001), whereas slight inhibition of endocytosis is observed upon neutralization of CD51/alphaV integrin (24 percent, p less than 0.05). No inhibition of endocytosis is seen when CD47 and CD29/beta1 integrin domains were inhibited. Inhibition of endocytosis is presented as a percentage of thrombospondin-1-dependent inhibition of endocytosis, and was calculated as the ratio of the difference between the median fluorescence of immature dendritic cells interacted with DiI-stained apoptotic cells in the presence of thrombospondin-1 and isotype control, or thrombospondin-1 and a specific antibody.
Figure 8B:
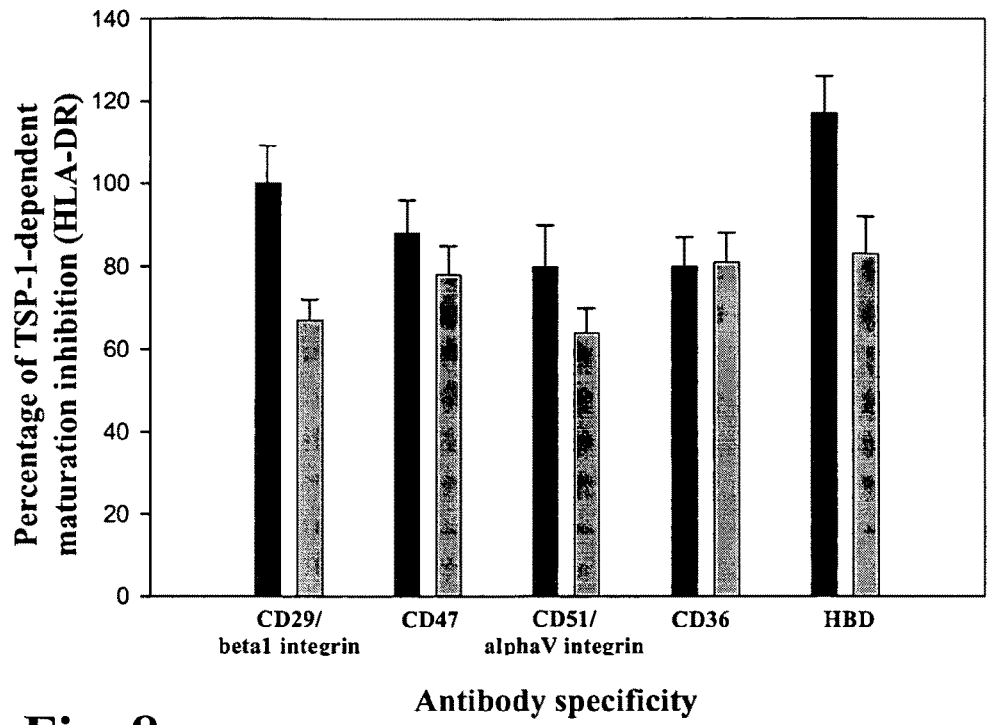
FIGS. 8b-c are histograms depicting that thrombospondin-1-mediated inhibition of dendritic cell maturation involves interaction of thrombospondin-1 with thrombospondin-1 receptors CD36, CD47, CD51/alphaV integrin and CD29/beta1 integrin. Immature dendritic cells were treated with several antibodies directed against the heparin-binding domain or against one of thrombospondin-1 receptors CD36, CD47, CD51/alphaV integrin or CD29/beta1 integrin. The treated cells were then washed, and interacted with DiI-stained apoptotic monocytes in the presence of 2 micrograms per milliliter thrombospondin-1. Surface display of HLA-DR (DR.
Figure 8C:
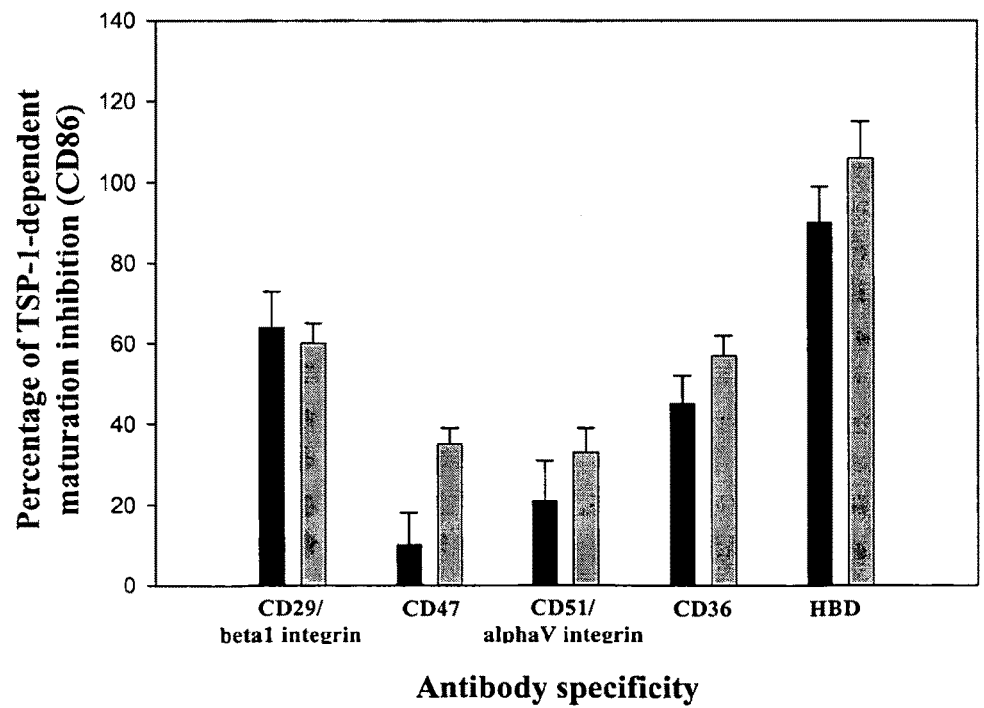

As is described and illustrated in Example 1 of the Examples section below (refer, for example, to FIGS. 8b-c(, modulating the interaction between the heparin-binding domain of thrombospondin-1 and CD29/integrin beta1, and thereby between the heparin-binding domain and receptors of the present invention which comprise CD29/integrin beta1, can be used to effectively regulate differentiation of immunostimulatory/mature antigen-presenting cells, such as dendritic cells.

As mentioned hereinabove, stimulation of a desired/therapeutic immune response in a subject of the present invention is effected, according to teachings of the present invention, by downregulating in the subject an interaction between a heparin-binding domain and a receptor of the present invention.

Downregulating in the subject the interaction between the heparin-binding domain and the receptor may be achieved in any of various ways.

Preferably, downregulating the interaction between the heparin-binding domain and the receptor is effected by a method which comprises administering to the subject a compound which comprises an inhibitor of the interaction. The inhibitor is preferably a ligand, more preferably a specific ligand, of the heparin-binding domain and/or of the receptor. Preferably, the inhibitor is capable of preventing/decreasing the binding of the heparin-binding domain to the receptor.

According to the teachings of the present invention, any of various types of ligands of the heparin-binding domain may be employed for downregulating the interaction between the heparin-binding domain and the receptor.

The heparin-binding domain ligand is preferably a specific ligand of the heparin-binding domain.

Preferably, the heparin-binding domain ligand is an antibody or an antibody fragment.

The antibody or antibody fragment capable of binding the heparin-binding domain is preferably polyclonal. Alternately, the antibody/antibody fragment may be monoclonal. The polyclonal antibody/antibody fragment capable of binding the heparin-binding domain is preferably derived from an ovine mammal, preferably a goat. Alternately, the antibody or antibody fragment may be derived from any of various mammals commonly employed for raising polyclonal antibodies, such as rodents, equines, ruminants, primates, and the like.

The antibody capable of binding the heparin-binding domain is preferably of the IgG isotype. Alternately, the antibody may be of another isotype, such as the IgM isotype.

The antibody capable of binding the heparin-binding domain is preferably generated by immunizing an organism with an N-terminal portion of the thrombospondin which comprises at least a portion of the heparin-binding domain, more preferably which comprises the entire heparin-binding domain.

A particularly suitable heparin-binding domain-binding polyclonal antibody is a goat polyclonal IgG antibody preparation raised against an N-terminal portion of the heparin-binding domain, such as polyclonal goat anti-human thrombospondin-1 N-terminus antibody (N-20; Santa Cruz Biotechnology Inc., Cat No. sc-12312, Santa Cruz Calif., U.S.). As is described and illustrated in Example 1 of the Examples section below (refer, for example, to FIGS. 8*b*-*c*), such an antibody can be used to optimally promote differentiation of human immunostimulatory/mature dendritic cells.

Obtaining antibodies/antibody fragments capable of specifically binding essentially any desired antigen, such as a heparin-binding domain of the present invention, is routinely practiced in the art, and guidance for obtaining such antibodies/antibody fragments is provided hereinbelow.

Alternately, the ligand of the heparin-binding domain may be a compound which comprises at least a portion of the receptor of the heparin-binding domain, where such portion is capable of binding the heparin-binding domain. Alternately, the ligand may be a mimetic of such a portion of the receptor.

Preferably, the compound which comprises the heparin-binding domain-binding portion of the receptor of the heparin-binding domain or mimetic thereof is soluble in an aqueous medium.

Any one of various types of water-soluble compounds which comprise the heparin-binding domain-binding portion of the receptor of the heparin-binding domain, or mimetic thereof, may be employed.

A heparin-binding domain-binding portion of a receptor of the present invention, such as CD29/beta1 integrin, can be solubilized by recombinant fusion with an antibody Fc domain. Such fusion proteins are routinely obtained and employed in the art, wherein they may be generically referred to as "immunoadhesins" (refer, for example, to Chamow S M, Ashkenazi A., 1996. Immunoadhesins: principles and applications. Trends Biotechnol. 14:52-60). Therapeutic use of immunoadhesins for treatment of immunity-related diseases is routine in the art (refer, for example, to Dick A D, Isaacs J D., 1999. Immunomodulation of autoimmune responses with monoclonal antibodies and immunoadhesins: treatment of ocular inflammatory disease in the next millennium. Br J Opthalmol. 83:1230-4).

Soluble forms of receptors of the present invention, such as CD29/beta1 integrin, are well known in the art (refer, for example, to Fortunati E. et al., 2000. Gene Ther. 7:1505-15). Soluble forms of extracellular/ligand-binding portions receptors of the present invention, such as CD29/beta1 integrin, are also well known in the art (refer, for example, to Denda S. et al., 1998. Mol Biol Cell. 9:1425-35).

According to one embodiment, the present invention provides a method of treating an immunity-related disease of the present invention in a subject of the present invention, where the method comprises administering to the subject a compound which comprises an inhibitor of the interaction, with the proviso that the inhibitor of the interaction does not comprise at least a portion of a heparin or heparin-like molecule which is capable of binding the heparin-binding domain.

It will be appreciated that the teaching of the present invention whereby administration of a ligand of a heparin-binding domain of a thrombospondin is used to stimulate an immune response for treatment of a disease characterized by an insufficient immune response is clearly novel and non-obvious over the prior art in view of the prior art use of heparin, which is by definition a heparin-binding domain ligand, as an immunosuppressant (Gorski A. et al., 1994. Low-dose heparin: a novel approach in immunosuppression. Transpl Int. 7:S567-9; Lagodzinski Z. et al., 1990. Immunosuppressive action of low-dose heparin. Effect on skin allograft survival. Transplantation. 50:714-5; Gorski A., 1990. [Immunosuppressive effect of heparin]. Pol Arch Med. Wewn. 83:208-11).

According to the teachings of the present invention, any of various types of ligands of the receptor of the heparin-binding domain may be employed for downregulating the interaction between the heparin-binding domain and the receptor. The ligand of the receptor is preferably a specific ligand of the receptor.

It will be appreciated that, ideally, the receptor ligand is a substantially non-agonistic ligand of the receptor, so as to avoid counterproductively mimicking the interaction between the heparin-binding domain and the receptor when administering the receptor ligand to downregulate the interaction.

Preferably, the receptor ligand is an antibody or antibody fragment.

A suitable antibody or antibody fragment capable of binding a receptor of the present invention such as CD29/beta1 integrin is mouse anti-human CD29/beta1 integrin monoclonal antibody (clone P4C10; Chemicon International; Catalog No. MAB 1987Z). As is described and illustrated in Example 1 of the Examples section below (refer, for example, to FIGS. 8b-c), such an anti-CD29/beta1 integrin antibody can be used to optimally promote differentiation of immunostimulatory/mature dendritic cells relative to prior art blocking antibodies specific for thrombospondin-1 receptors used for attempting to modulate such differentiation.

A suitable antibody or antibody fragment capable of binding a receptor of the present invention, such as CD91, is a mouse anti-human CD91 monoclonal antibody. Such antibodies may be obtained from American Diagnostica (Product No. 3402 or 3501).

Alternately, the receptor ligand may be a portion of a thrombospondin. The use of portions of thrombospondins which can be used as inhibitors of interactions between receptors of the present invention and thrombospondin domains, such as heparin-binding domains, are known in the art (refer, for example, to Calzada M J, Roberts D D., 2005. Novel integrin antagonists derived from thrombospondins. Curr Pharm Des. 11:849-66).

As is described and illustrated in the Examples section which follows (refer, in particular, to FIGS. 8b-c) the presently taught use of anti-beta1 integrin or anti-heparin-binding domain blocking antibodies is clearly highly effective and optimal relative to prior art blocking antibodies (i.e. antibodies specific for the thrombospondin-1 receptors CD36, CD47, or CD51/alphaV integrin) for inhibiting thrombospondin-1-mediated differentiation of antigen-presenting cells. As such, it will be appreciated that the presently taught use of anti-beta1 integrin or anti-heparin-binding domain blocking antibodies is optimal relative to use of prior art blocking antibodies for achieving therapeutic immunostimulation in a subject for treatment of a disease characterized by an insufficient immune response of the present invention.

Suitable types of antibodies and antibody fragments for practicing the present invention, and ways in which these may be obtained, are further described hereinbelow.

As used herein, the term "antibody" refers to a substantially intact antibody molecule.

As used herein, the phrase "antibody fragment" refers to a functional fragment of an antibody that is capable of binding to an antigen, such as a heparin-binding domain or receptor of the present invention.

Suitable functional antibody fragments for practicing the present invention include those which comprise whole or essentially whole variable regions of both light and heavy antibody chains, such as an Fv, a single chain Fv, an Fab, an Fab', and an $F(ab')_2$.

Such antibody fragments are defined as follows:

(i) Fv, an antibody fragment, generally genetically engineered, containing a monovalent antigen-binding portion of an antibody molecule consisting of the variable region of the light chain and the variable region of the heavy chain expressed as two chains held together via disulfide bonds;

(ii) single chain Fv ("scFv"), a genetically engineered single chain polypeptide, containing a monovalent antigen-binding portion of an antibody molecule, which includes the variable region of a light chain of an antibody and the variable region of the heavy chain of an antibody linked together via a genetically engineered polypeptide linker;

(iii) Fab, a fragment of an antibody molecule containing a monovalent antigen-binding portion of an antibody molecule which can be obtained by treating a whole antibody with the enzyme papain to yield the intact light chain and the Fd fragment of the heavy chain which consists of the variable and CH1 domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); and (v) $F(ab')_2$, a fragment of an antibody molecule containing a divalent antigen-binding portion of an antibody molecule which can be obtained by treating whole antibody with the enzyme pepsin (i.e., a dimer of Fab' fragments held together by two disulfide bonds).

Monoclonal and polyclonal antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S. A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumin (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in E. coli or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be cross-linked by chemicals such as glutaraldehyde.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

It will be appreciated that for human therapy or diagnostics, humanized antibodies are preferably used. Humanized forms of non human (e.g., murine) antibodies are genetically engineered chimeric antibodies or antibody fragments having—preferably minimal—portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies or antibody fragments are obtained, they may be characterized with respect to target antigen binding capacity using any of various suitable standard techniques, including enzyme-linked immunosorbent assay (ELISA), surface plasmon resonance (SPR), fluorescence activated cell sorting (FACS), Western immunoblotting assay, dot-blotting, and the like.

It will be well within the purview of one of ordinary skill in the art to obtain or produce any polypeptide taught herein for practicing embodiments of the present invention, such as a heparin-binding domain or thrombospondin-binding portion thereof of the present invention; or a receptor or heparin-binding domain-binding portion thereof of the present invention. A polypeptide of the present invention may be obtained from a commercial supplier, may be isolated from a natural source, or may be produced standard recombinant methods. Ample guidance for production of recombinant polypeptides is provided in the literature of the art (refer, for example, to Sambrook et al., infra, and the associated list of references provided in the introductory paragraph of the Examples section which follows).

It will also be well within the purview of the ordinarily skilled artisan to obtain or produce a non-polypeptide compound taught herein for practicing embodiments of the present invention, such as a non-polypeptide ligand of a receptor of the present invention, or a non-polypeptide heparin-binding domain of the present invention. A non-polypeptide compound of the present invention may be obtained from a commercial supplier, may be isolated from a natural source, or may be produced according to standard chemical techniques. For guidance regarding chemical synthesis of such compounds, refer, for example to the extensive guidelines provided by The American Chemical Society (http://www.chemistry.org/portal/Chemistry). One of ordinary skill in the art, such as, for example, a chemist, will possess the required expertise for practicing appropriate chemical synthesis techniques.

Thus, the present invention provides a method of treating in a subject of the present invention a disease characterized by an insufficient immune response of the present invention. The method is effected by administering to the subject a ligand of a heparin-binding domain, and/or a ligand of a heparin-binding domain of the present invention.

As mentioned hereinabove, suppression of a pathological immune response in a subject of the present invention is effected, according to teachings of the present invention, by upregulating in the subject an interaction between a heparin-binding domain and a receptor of the present invention.

Upregulating in the subject the interaction between the heparin-binding domain and the receptor may be achieved in any of various ways.

Preferably, upregulating the interaction between the heparin-binding domain and the receptor is effected by a method which comprises administering to the subject a compound which comprises an agonist of the interaction.

According to teachings of the present invention, the agonist is preferably the heparin-binding domain in a substantially isolated state.

A suitable heparin-binding domain for practicing the present invention can be obtained via any one of various commonly employed art methods. For example, ample guidance for producing recombinant heparin-binding domain is provided in the literature of the art (refer, for example, to: Yabkowitz R. et al., 1989. Expression and initial characterization of a recombinant human thrombospondin heparin-binding domain. J Biol Chem. 264:10888-96). It will be appreciated that the heparin-binding domain and/or the thrombospondin-1 may be produced from a nucleic acid construct which comprises at least a portion of TSP-1 nucleic acid sequence as set forth in SEQ ID NO:7.

Alternately, the agonist may be a mimetic of the heparin-binding domain.

Obtaining or producing peptide or non-peptide mimetics (e.g. "peptidomimetics") of polypeptides, such as heparin-binding domains of the present invention, or portions thereof capable of binding a receptor of the present invention; or of receptors of the present invention, or portions thereof capable of binding a heparin-binding domain of the present invention, will be well within the purview of one of ordinary skill in the art, and ample guidance for obtaining or producing such mimetics is available in the literature of the art (refer, for example, to: Timmerman P. et al., 2005. Rapid and quantitative cyclization of multiple peptide loops onto synthetic scaffolds for structural mimicry of protein surfaces. Chembiochem. 6:821-824; Moriuchi T, Hirao T., 2004. Highly ordered structures of peptides by using molecular scaffolds. Chem Soc Rev. June 20; 33(5):294-301. Epub 2004 May 19; Perez J J. et al., 2002. Molecular modeling in the design of peptidomimetics and peptide surrogates. Curr Med Chem. 9:2209-29; Preissner R. et al., 2001. Matching organic libraries with protein-substructures. J Comput Aided Mol Des. 15):811-7; Hruby V J, Balse P M., 2000. Conformational and topographical considerations in designing agonist peptidomimetics from peptide leads. Curr Med Chem. 7:945-70; Hruby V J. et al., 1996. Design considerations and computer modeling related to the development of molecular scaffolds and peptide mimetics for combinatorial chemistry. Mol Divers. 2:46-56; Hruby V J. et al., 1996. Design considerations and computer modeling related to the development of molecular scaffolds and peptide mimetics for combinatorial chemistry. Mol Divers. 2:46-56; Fassina G., 1994. Complementary peptides as antibody mimetics for protein purification and assay. Immunomethods. 5:121-9).

Thus, the present invention provides a method of treating in a subject a disease characterized by a pathological immune response which is effected by administering to the subject a heparin-binding domain of the present invention.

As described hereinabove, according to teachings of the present invention suppressing a pathological immune response in a subject of the present invention so as to treat in the subject a disease characterized by such a response may be achieved by administering to the subject an agonist, such as a heparin-binding domain of the present invention, of a receptor of the present invention.

Administering the agonist to the subject may be effected in any of various ways so as to achieve suppression of the pathological immune response, and thereby treatment of the disease.

For example, administering the agonist to the subject may be effected by administering the agonist to the subject according to any one of various therapeutic amounts, according to any one of various administration regimens, and/or according to any one of various administration routes.

Administering to the subject an agonist of the present invention such as a heparin-binding domain of a thrombospondin may be effected by administering to the subject a systemic dose thereof in kilograms body weight corresponding to the amount thereof in a dose of thrombospondin-1 selected from a range of about 0.1 to about 10 milligrams per kilogram body weight, more preferably about 0.1 to about 9 milligrams per kilogram body weight, more preferably about 0.1 to about 8 milligrams per kilogram body weight, more preferably about 0.1 to about 7 milligrams per kilogram body weight, more preferably about 0.1 to about 6 milligrams per kilogram body weight, more preferably about 0.1 to about 5 milligrams per kilogram body weight, more preferably about 0.1 to about 4 milligrams per kilogram body weight, more preferably about 0.1 to about 3 milligrams per kilogram body weight, more preferably about 0.2 to about 9 milligrams per kilogram body weight, 0.3 to about 3 milligrams per kilogram body weight, and most preferably, about 1 milligram per kilogram body weight.

As used herein the term "about" refers to plus or minus 10 percent.

As is described and illustrated in Example 1 of the Examples section which follows (refer, for example, to FIG. 7b), immunostimulatory differentiation/maturation of antigen-presenting cells such as human dendritic cells, can be achieved by exposing such cells to a concentration of thrombospondin-1 of 1 microgram per milliliter. It will be appreciated that since living tissues have a density of about 1 gram per milliliter, a concentration of agonist of 1 microgram per milliliter can be achieved in the subject by administration thereto of a systemic dose of agonist of 1 milligram per kilogram body weight.

Alternately, further in accordance with the aforementioned rationale, administering to the subject an agonist of the present invention such as a heparin-binding domain of a thrombospondin may be effected by administering to the subject a local tissue dose thereof in micrograms per cubic centimeter corresponding to the amount thereof in a dose of thrombospondin-1 selected from a range of about 0.1 to about 10 micrograms per cubic centimeter local tissue, more preferably about 0.1 to about 9 micrograms per cubic centimeter local tissue, more preferably about 0.1 to about 8 micrograms per cubic centimeter local tissue, more preferably about 0.1 to about 7 micrograms per cubic centimeter local tissue, more preferably about 0.1 to about 6 micrograms per cubic centimeter local tissue, more preferably about 0.1 to about 5 micrograms per cubic centimeter local tissue, more preferably about 0.1 to about 4 micrograms per cubic centimeter local tissue, more preferably about 0.1 to about 3 micrograms per cubic centimeter local tissue, more preferably about 0.3 to about 3 micrograms per cubic centimeter local tissue, and most preferably, about 1 microgram per cubic centimeter local tissue.

As described hereinabove, according to teachings of the present invention stimulating a therapeutic/beneficial immune response in a subject of the present invention so as to treat in the subject a disease characterized by an insufficient immune response may be achieved by administering to the subject an inhibitor of the present invention, such as a ligand of a heparin-binding domain of the present invention, or a ligand of a receptor of the present invention.

Administering the inhibitor to the subject may be effected in any of various ways so as to achieve stimulation of the therapeutic/beneficial immune response, and thereby treatment of the disease.

For example, administering the inhibitor to the subject may be effected by administering the inhibitor to the subject according to any one of various therapeutic amounts, according to any one of various administration regimens, and/or according to any one of various administration routes.

Administering to the subject an inhibitor of the present invention, such as an antibody capable of binding a heparin-binding domain of the present invention, or an antibody capable of binding a receptor of the present invention, may be effected by administering to the subject a systemic dose thereof selected from a range of about 1 nanogram to about 100 milligrams per kilogram body weight, more preferably about 10 nanograms to about 100 milligrams per kilogram body weight, more preferably about 100 nanograms to about 100 milligrams per kilogram body weight, more preferably about 1 to about 100 milligrams per kilogram body weight, more preferably about 1 to about 90 milligrams per kilogram body weight, more preferably about 1 to about 80 milligrams per kilogram body weight, more preferably about 1 to about 70 milligrams per kilogram body weight, more preferably about 1 to about 60 milligrams per kilogram body weight, more preferably about 1 to about 50 milligrams per kilogram body weight, more preferably about 1 to about 40 milligrams per kilogram body weight, more preferably about 1 to about 30 milligrams per kilogram body weight, more preferably about 1 to about 20 milligrams per kilogram body weight, more preferably about 5 to about 15 milligrams per kilogram body weight, and most preferably about 10 milligrams per kilogram body weight.

As is described and illustrated in Example 1 of the Examples section which follows (refer, for example, to FIGS. 8b-c), inhibition of immunostimulatory differentiation/maturation of antigen-presenting cells such as human dendritic cells, can be achieved by exposing such cells to a concentration of anti-heparin-binding domain antibody or anti-CD29/beta1 integrin antibody of 10 micrograms per milliter. It will be appreciated that since living tissues have a density of about 1 gram per milliliter, a concentration of agonist of 10 micrograms per milliliter can be achieved in the subject by administration thereto of a systemic dose of the agonist of 10 milligrams per kilogram body weight.

Alternately, further in accordance with the aforementioned rationale, administering to the subject an inhibitor of the present invention, such as an antibody capable of binding a heparin-binding domain of the present invention, or an antibody capable of binding a receptor of the present invention, may be effected by administering to the subject a local tissue dose thereof in micrograms per cubic centimeter selected from a range of about 1 nanogram to about 100 micrograms per cubic centimeter local tissue, more preferably about 10 nanograms to about 100 micrograms per cubic centimeter local tissue, more preferably about 100 nanograms to about 100 micrograms per cubic centimeter local tissue, more preferably about 1 to about 100 micrograms per cubic centimeter local tissue, more preferably about 1 to about 90 micrograms per cubic centimeter local tissue, more preferably about 1 to about 80 micrograms per cubic centimeter local tissue, more preferably about 1 to about 70 micrograms per cubic centimeter local tissue, more preferably about 1 to about 60 micrograms per cubic centimeter local tissue, more preferably about 1 to about 50 micrograms per cubic centimeter local tissue, more preferably about 1 to about 40 micrograms per cubic centimeter local tissue, more preferably about 1 to about 30 micrograms per cubic centimeter local tissue, more preferably about 1 to about 20 micrograms per cubic centimeter local tissue, more preferably about 5 to about 15 micrograms per cubic centimeter local tissue, and most preferably about 10 micrograms per cubic centimeter local tissue.

Ample guidance for therapeutic administration of antibodies, including regarding suitable dosages and administration regimens, is available in the literature of the art (refer, for example, to Harris M., 2004. Monoclonal antibodies as therapeutic agents for cancer. Lancet Oncol. 5:292-302; Curtis M A., 2003. New monoclonal antibodies for hematologic malignancies (and breast cancer). Med Health R I. 86:256-7; Houshmand P, Zlotnik A., 2003. Targeting tumor cells. Curr Opin Cell Biol. 15:640-4).

The route of administration will depend on the disease being treated, as well as any relevant subject-specific parameters, and will be selected so as to achieve suitable delivery of an immunoregulatory/therapeutic compound of the present invention. Suitable routes of administration are described hereinbelow.

An immunoregulatory/therapeutic compound of the present invention may be suitably administered to the subject over any one of various durations, and may be suitably administered continuously, or discontinuously in order to achieve disease treatment.

Depending on the application, purpose and context, an immunosuppressive compound of the present invention may be suitably administered once or twice to a subject of the present invention, or may be administered every one or two weeks for any of various suitable durations.

Treatment of a disease of the present invention can be achieved in a subject belonging to any one of various species by administering an immunoregulatory/therapeutic compound of the present invention thereto according to teachings of the present invention. Preferably, the subject is a homeotherm, more preferably a mammal and most preferably a human. It will be appreciated that the subject may be any organism having an immunophysiology involving thrombospondin-mediated inhibition of differentiation of immunostimulatory/mature antigen-presenting cells.

One of ordinary skill in the art, such as a physician or veterinarian, as appropriate, in particular an artisan specialized in the disease to be treated, will possess the necessary expertise for adapting the teachings of the present invention for suitably treating a particular disease of the present invention in a given subject. One of ordinary skill in the art will possess the necessary expertise for selecting a suitable administration route for suitably formulating an immunoregulatory/therapeutic compound of the present invention, for selecting a suitable administration route for administering an immunoregulatory/therapeutic compound of the present invention, for selecting a suitable regimen for administering an immunoregulatory/therapeutic compound of the present invention, and for suitably monitoring the disease during treatment so as to achieve a desired therapeutic outcome in the subject.

It will be appreciated that the present invention provides a novel and inventive use of an immunoregulatory/therapeutic compound of the present invention which may be used for the manufacture of a medicament for treatment of an immunity-related disease of the present invention.

Thus, the present invention provides an article of manufacture which comprises packaging material and a pharmaceutical composition, where the article of manufacture is identified in print in or on the packaging material for treatment of an immunity-related disease of the present invention in a subject of the present invention, and where the pharmaceutical composition comprises a pharmaceutically acceptable carrier and, as an active ingredient, an immunoregulatory/therapeutic compound of the present invention.

Thus, more particularly, the present invention provides an article of manufacture which comprises packaging material and a pharmaceutical composition, where the article of manufacture is identified in print in or on the packaging material for treatment of a disease characterized by a pathological immune response of the present invention in a subject of the present invention, and where the pharmaceutical composition comprises a pharmaceutically acceptable carrier and, as an active ingredient, a heparin-binding domain of the present invention in a substantially isolated state. Preferably, the substantially isolated state is a fully isolated state.

Each dose unit of the pharmaceutical composition may comprise an amount of the substantially isolated heparin-binding domain of a thrombospondin which corresponds to the amount thereof in a quantity of the thrombospondin selected from a range of about 0.1 microgram to about 1 gram. It will be appreciated that a dose-unit of 0.1 microgram of thrombospondin corresponds to a local tissue dose thereof of 0.1 microgram per cubic centimeter administered to a local tissue volume of 1 cubic centimeter. It will be further appreciated that a dose-unit of 1 gram of thrombospondin corresponds to a systemic dose of 10 milligrams per kilogram body weight administered to a subject weighing 100 kilograms.

Thus, the present invention further particularly provides an article of manufacture which comprises packaging material and a pharmaceutical composition, where the article of manufacture is identified in print in or on the packaging material for treatment of a disease characterized by an insufficient immune response of the present invention in a subject of the present invention, and where the pharmaceutical composition comprises a pharmaceutically acceptable carrier and, as one or more active ingredients: a ligand of a heparin-binding domain of the present invention; and/or a ligand of a receptor of the present invention.

Each dose unit of the pharmaceutical composition may comprise an amount of the ligand of the heparin-binding domain and/or of the receptor ligand selected from a range of about 1 nanogram to about 10 grams, more of about 1 microgram to about 10 grams. It will be appreciated that a dose-unit of 1 microgram of the ligand of the heparin-binding domain and/or of the receptor ligand corresponds to a local tissue dose thereof of 1 microgram per cubic centimeter administered to a local tissue volume of 1 cubic centimeter. It will be further appreciated that a dose-unit of 10 grams of the ligand of the heparin-binding domain and/or of the receptor ligand corresponds to a systemic dose of 100 milligrams per kilogram body weight administered to a subject weighing 100 kilograms.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject.

Herein the term "active ingredient" refers to the immunoregulatory/therapeutic compound accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

Pharmaceutical compositions of the present invention may be manufactured by processes well known in the art. e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in-vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in-vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As described hereinabove, the present invention may be used to treat any one of various diseases characterized by an insufficient immune response, such as an infectious and/or tumoral disease.

The pathogenesis of numerous types of neoplastic diseases, in particular that of various types of cancers is facilitated by and/or associated with immunosuppression, such as that mediated by secretion of TGF-beta by cancer cells, down-regulation of HLA molecules by cancer cells, and by phosphorylation patterns in T-cell receptor signal transduction mediators associated with impairment of protective T-cell function. Cancer pathogenesis associated with immunosuppression is clearly illustrated, for example, by the marked incidence of cancers such as Kaposi's sarcoma in acquired immunodeficiency syndrome (AIDS) patients. As such, it will be appreciated that the method of the present invention, can be advantageously used treat a cancer, in particular any of the numerous types of cancer which are associated with immunosuppression, by virtue of enabling stimulation of immune responses in a subject. In particular, it will be appreciated that an immunostimulatory compound of the present invention, by virtue of counteracting inhibition of immunostimulatory differentiation/maturation of antigen-presenting cells exposed to apoptotic cells will be particularly suitable for treating diseases such as cancers which escape immune surveillance via apoptotic clearance.

Examples of infectious diseases which may be treated according to teachings of the present invention include, but are not limited to, a wart, a bacterial infection, a fungal infection, a mycoplasma infection, a protozoan infection, and a viral infection.

Examples of tumoral diseases which may be treated according to teachings of the present invention include, but are not limited to, an adenoma, a blastoma, a benign tumor, a bone tumor, a brain tumor, a carcinoma, a cardiovascular tumor, a connective tissue tumor, a gastrointestinal tumor, a glandular tumor, a glioma, a gonadal tumor, a head and neck tumor, a hematological tumor, a hepatic tumor, a lymphoid tumor, a malignant tumor, a mammary tumor, a muscle tumor, a neurological tumor, an ocular tumor, a pancreatic tumor, a precancer, a polyp, a pulmonary tumor, a renal tumor, a reproductive organ tumor, a sarcoma, a skin tumor, a thyroid tumor, and a wart.

Specific examples of tumoral diseases which may be treated according to teachings of the present invention include, but are not limited to, hereditary adrenocortical carcinoma, bladder cancer; ductal breast cancer; invasive intraductal breast cancer; sporadic breast cancer; breast cancer, type 4; type 4 breast cancer; Burkitt's lymphoma; cervical carcinoma; colorectal adenoma; colorectal cancer; hereditary nonpolyposis type 1, 2, 3, 6, or 7; dermatofibrosarcoma protuberans; endometrial carcinoma; esophageal cancer; gastric cancer, fibrosarcoma, glioblastoma multiforme; multiple glomus tumor; hepatoblastoma; hepatocellular cancer; hepatocellular carcinoma; acute lymphoblastic leukemia; leukemia, acute myeloid; leukemia, acute myeloid, with eosinophilia; acute nonlymphocytic leukemia; chronic myeloid leukemia; Li-Fraumeni syndrome; liposarcoma, small cell lung cancer; non-Hodgkin's lymphoma; lynch cancer family syndrome II; male germ cell tumor; mast cell leukemia; medulloblastoma; melanoma; meningioma; multiple endocrine neoplasia; myxosarcoma; neuroblastoma; osteosarcoma; ovarian cancer; serous ovarian cancer; ovarian carcinoma; ovarian sex cord tumors; pancreatic cancer; pancreatic endocrine tumors; familial nonchromaffin paraganglioma; pilomatricoma; pituitary tumor; prostate adenocarcinoma; prostate cancer; familial and sporadic papillary renal cell carcinoma; retinoblastoma; rhabdoid tumors; rhabdomyosarcoma; soft tissue sarcoma; head and neck squamous cell carcinoma; T-cell acute lymphoblastic leukemia; uterine cervix carcinoma, Wilms' tumor type 2; Wilms' tumor, type 1; and the like.

As described hereinabove, the present invention may be used diseases characterized by a pathological immune response may be an autoimmune, transplantation-related, inflammatory and/or alloimmune pregnancy disease.

Examples of autoimmune diseases which may be treated according to teachings of the present invention include a cardiovascular autoimmune disease, a connective tissue autoimmune disease, a gastrointestinal autoimmune disease, a glandular autoimmune disease, a gonadal autoimmune disease, a hematological autoimmune disease, a hepatic autoimmune disease, a mammary autoimmune disease, a muscular autoimmune disease, a neurological autoimmune disease, an ocular autoimmune disease, an oropharyngeal autoimmune disease, a pancreatic autoimmune disease, a pulmonary autoimmune disease, a renal autoimmune disease, a reproductive organ autoimmune disease, a rheumatoid autoimmune disease, a skin autoimmune disease, a systemic autoimmune disease, a thyroid autoimmune disease.

Examples of cardiovascular autoimmune diseases comprise atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of connective tissue autoimmune diseases comprise ear diseases, autoimmune ear diseases (Yoo T J. et al., Cell Immunol 1994 August; 157 (1):249) and autoimmune diseases of the inner ear (Gloddek B. et al., Ann NY Acad Sci 1997 Dec. 29; 830:266).

Examples of gastrointestinal autoimmune diseases comprise chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of glandular autoimmune diseases comprise pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases comprise autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of hepatic autoimmune diseases comprise hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of muscular autoimmune diseases comprise myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6): 234).

Examples of neurological autoimmune diseases comprise multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12): 2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann NY Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of rheumatoid autoimmune diseases comprise rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of renal autoimmune diseases comprise nephritis and autoimmune interstitial nephritis (Kelly C J. J Am Soc Nephrol 1990 August; 1 (2):140).

Examples of skin autoimmune diseases comprise autoimmune bullous skin diseases, such as, but not limited to, pemphigus vulgaris, bullous pemphigoid and pemphigus foliaceus, discoid lupus erythematosus.

Examples of systemic autoimmune diseases comprise systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Examples of transplantation-related diseases which may be treated according to teachings of the present invention include graft rejection, chronic graft rejection, subacute graft rejection, hyperacute graft rejection, acute graft rejection and graft-versus-host disease (GVHD).

Examples of inflammatory diseases which may be treated according to the teachings of the present invention include acute inflammatory diseases, anaphylactic shock, atherosclerosis, cachexia, chronic inflammatory diseases, episodic inflammatory diseases, inflammation associated with mechanical injury, gangrene, idiopathic inflammation menstruation-related inflammation, musculo-skeletal inflammation, myocardial infarction, neurodegenerative diseases, prosthetic implant-related inflammation, restenosis following percutaneous transluminal coronary angioplasty (PTCA), septic shock, stroke, toxic shock syndrome, transient inflammatory disease, thrombosis, ulcers, and vascular stent-related inflammation.

Examples of acute inflammatory diseases include acute myocardial infarction, and acute thrombosis.

Examples of episodic inflammatory diseases include episodic transient fevers, such as familial Mediterranean fever (FMF).

Examples of alloimmune pregnancy diseases which may be treated according to teachings of the present invention include alloimmune pregnancy loss (Tincani A. et al., Lupus 1998; 7 Suppl 2:S107-9).

Thus, the present invention provides novel, non-obvious and highly effective methods and medicaments for treatment of a broad range of immunity-related diseases for which no satisfactory/optimal treatment methods are available.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al., (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Optimal Inhibition of TSP-1 HBD-Mediated Endocytosis Using Blocking Anti-HBD Antibody, and Optimal Suppression of TSP-1-Mediated Inhibition of Differentiation of Dendritic Cell Maturation by Blocking Antibody Against HBD or the HBD-Binding TSP-1 Receptor CD29/Beta1 Integrin Introduction:

In view of the role of thrombospondin-1 in mediating endocytosis of apoptotic cells by antigen-presenting cells, and in view of the role of such endocytosis in inhibiting differentiation of immunostimulatory/mature dendritic cells, a potentially advantageous strategy for treating immunity-related diseases, such as those characterized by pathological or insufficient immune responses, may be to suitably modulate thrombospondin-1-mediated inhibition of differentiation of immunostimulatory/mature antigen-presenting cells. While various approaches have been proposed in the prior art for practicing such modulation, these approaches suffer from critical disadvantages; namely ineffectiveness or suboptimal effectiveness, not having been attempted in-vivo, and not having demonstrated any therapeutic efficacy. As such, there is a need for novel and effective methods and medicaments for achieving modulation of thrombospondin-1-mediated inhibition of differentiation of immunostimulatory/mature antigen-presenting cells. While reducing the present invention to practice, as described below, a novel and optimal method of modulating such differentiation was unexpectedly uncovered, thereby overcoming the limitations of the prior art.

Materials and Methods:

Media and Reagents:

Culture medium consisted of RPMI 1640 supplemented with 1 percent L-glutamine, 1 percent penicillin/streptomycin (Biological Industries, Kibbutz Beit-Haemek, Israel), 1 percent autologous human plasma, recombinant human GC-CSF and recombinant human IL-4 (R&D Systems, Minneapolis Minn., US, and PeproTech, London, UK). Ficoll-Paque was purchased from Amersham Pharmacia Biotech (Upsala, Sweden). FITC-conjugated mouse anti-human HLA-DR antibody, phycoerythrin (PE)-conjugated mouse anti-human CD83 antibody, FITC-conjugated mouse anti-human CD1a antibody, and matching isotype controls were obtained from IQ Products (Groningen, The Netherlands). FITC-conjugated mouse anti-human CD86/B7-2 antibody was obtained from Cymbus Biotechnology (Hampshire, UK). Latex beads (Cat. No. LB-11), green fluorescent latex beads (Cat. No. L-4655), and lipopolysaccharide (LPS) were obtained from Sigma-Aldrich (St. Louis Mo., US). Thrombospondin (TSP)-1 was obtained from Sigma and Protein Sciences (Meriden Conn., US), and 1,1'-dioctadecyl-3,3,3', 3'-tetramethyl-indocarbocyanineperchlorate (DiI) was obtained from Molecular Probes (Eugene Oreg., US). Unless otherwise indicated, all chemicals for mass spectrometry were purchased from Sigma-Aldrich and were of analytical grade. MilliQ water (Millipore, Bedford Mass., US) was used to prepare all solutions. For mass spectral analysis and preparation of digests, HPLC-grade methanol and acetonitrile (JT Baker, Phillipsburg N.J., US) were used. Sequencing-grade trypsin was obtained from Promega (Madison, Wis., US).

Induction and Detection of Apoptosis:

Serum-withdrawal treatment was used for generation of apoptotic monocytes. Monocytes were generated by plating peripheral blood CD14+-selected monocytes (Miltenyi Biotech, Bergisch Gladbach, Germany) with serum-free RPMI at a concentration of 7.5 million cells per milliliter for up to 24 hours in 35 mm diameter dishes. Apoptosis was detected by double-staining with FITC-conjugated annexin-V and propidium iodide (PI; Nexins Research BV, Hoeven, The Netherlands), as well as by estimating the proportion of hypodiploid fraction in propidium iodide-stained cells (Shoshan et al., 2001). The pancaspase inhibitor zVAD-fmk (Bachem, Bubendorf, Switzerland) was used for inhibition of apoptosis.

Generation of Monocyte-Derived Dendritic Cells:

Human immature monocyte-derived dendritic cells were generated from the CD14+ fraction of peripheral blood mononuclear cells (PBMCs) of healthy blood donors' buffy coats, selected as previously described (Verbovetski et al., 2002). Briefly, PBMCs were isolated by centrifugation of blood over a Ficoll cushion, and anti-CD14 antibody-conjugated magnetic beads were used according to the manufacturer's instructions to isolate monocytes from PBMCs (Miltenyi Biotech). The isolated monocytes were distributed in 12-well plates at a concentration of 1.25 million cells in a volume of 1.5 milliliters culture medium supplemented with 1 percent autologous plasma, GC-CSF (1,000 units per milliliter), and IL-4 (1,000 units per milliliter). Every two days 150 microliters of medium was removed from the wells, and 250 microliters of medium supplemented with plasma, IL-4, and GC-CSF (500 units per milliliter) was added. By day six, greater than 90 percent of the cells were CD14-negative and CD1a+, with low expression of HLA-DR and CD86, and no expression of CD83.

Interaction of Apoptotic Monocytes with Immature Dendritic Cells:

For interaction assays, 800,000 apoptotic monocytes were labeled with 5 micrograms per milliliter DiI, as described elsewhere (Verbovetski et al., 2002), and were mixed with 200,000 immature dendritic cells on day six of culture (4:1 ratio), for 5 hours at 37 degrees centigrade, in 96-well plates, in 300 microliters of immature dendritic cell culture medium. Endocytosis of DiI by immature dendritic cells was quantitated via using a FACScan flow cytometer, as previously described (Verbovetski et al., 2002). Briefly, immature dendritic cells were separated from monocytes based on specific immunostaining for CD1a and CD14, respectively. FSC/SSC distribution and DiI uptake were measured.

Dendritic Cell Maturation Assays:

For dendritic cell maturation assays, unlabeled apoptotic monocytes were mixed with immature dendritic cells as described above for 5 hours, after which 1-10 nanograms per milliliter LPS (Sigma-Aldrich) to was added. The expression of maturation-related membrane molecules CD86, HLA-DR, and CD83 was examined 20 hours later.

Identification of Proteins Secreted by Apoptotic Cells:

I. Sample Preparation for SDS-PAGE:

Supernatants from cultures of apoptotic and viable monocytes were collected and their protein contents were analyzed via SDS-PAGE electrophoresis, as follows. Cultures of 60 million zVAD-fmk-treated monocytes and of 60 million serum-withdrawal-treated apoptotic monocytes were cleared of cells and undesired cellular debris by sequential centrifugations—first at 1,200 rpm for 5 minutes, then at 14,000×g for 5 minutes, and finally at 55,000×g for 1 hour using a Beckman Ti100 centrifuge with a TLS55 rotor (Beckman Coulter, Krefeld, Germany). The resulting supernatant was collected and analyzed. Prior to electrophoresis, supernatant proteins were concentrated and desalted using Sep-Pak C-18 cartridges (Waters Corporation, Milford Mass., US). Protein concentration was determined via Bradford assay (BioRad, Hercules Calif., US).

II. SDS-PAGE:

Gradient 8-18 percent polyacrylamide-SDS gels and SDS buffer were prepared according to the Laemmli method (Laemmli, 1970). The molecular mass of the protein bands was determined by means of a Precision Plus Protein standards kit (Bio-Rad). Proteins were visualized using a silver-staining kit (Amersham-Pharmacia), or Bio-Safe Coomassie (Bio-Rad), according to the manufacturer's instructions. Images of the developed gels were acquired using a Umax Power Look III scanner.

III. ESI-MS/MS:

Nano-electrospray ionization tandem mass spectrometry of proteins was carried out at the mass spectrometry facility in the Interdepartmental Unit of Hadassah Medical School at the Hebrew University of Jerusalem. For trypsin digestion, proteins from concentrated culture supernatant fractions were separated by SDS-PAGE. The region corresponding to the differential protein was excised and subjected to an in-gel digestion procedure, as previously described (Matsui et al., 1997). Briefly, the procedure includes washing and drying of gels, reduction and alkylation, rehydration with 10 nanograms per milliliter trypsin in 25 millimolar ammonium bicarbonate buffer solution, incubation for 12 to 16 hours at 37 degrees centigrade, and peptide extraction. In-gel tryptic digests were further desalted using C18 ZipTips (Millipore), and were eluted in 5 microliters of an elution buffer containing 60 percent (v/v) acetonitrile in 0.1 percent (v/v) formic acid (JT Baker).

Mass spectrometry was performed using a Micromass Q-T of system, equipped with a NanoFlow Probe Tip Type F (Micromass UK Ltd., Manchester, UK). The extracted peptide solution was collected in a borosilicate capillary tip (Protana, Odense, Denmark), and subjected to electrospray ionization (ESI) at a flow rate of 10 nanoliters per minute. The mass spectra were analyzed using MICROMASS PROTEIN-LYNX software. Proteins were identified using the MS-FIT proteomic tool software from the Matrix-Science web server.

Identification of Secreted Proteins from Cells Undergoing Apoptosis:

Concentrations of thrombospondin-1 in culture supernatants were determined via thrombospondin-1 enzyme immunoassay (EIA; Chemicon, Temecula, Calif.). Concentrations of IL-12 in culture supernatants were determined using IL-12 ELISA (Diaclone, Besancon, France), according to the manufacturer's instructions. Western immunoblotting analysis of culture supernatants was performed using the anti-thrombospondin-1 monoclonal antibody Ab-11 (Neomarkers). Protein extracts from supernatant of cultures of 30 million apoptotic monocytes (separated as described above), and of 30 million lysed monocytes, were separated via a 4-20 percent gradient SDS-PAGE gel, the separated proteins were transferred to a PVDF membrane (Millipore), the blotted membranes were blocked with 20 percent skimmed milk in PBST (0.05-0.1 percent Tween-20 in PBS). The blocked membrane was incubated with primary antibody for 2 hours at room temperature or overnight at 4 degrees centigrade, and then washed with PBST and incubated for 30 minutes with a 1:10,000 dilution of horseradish peroxidase (HRP)-conjugated goat anti-mouse antibody (Amersham Biosciences, Buckinghamshire, England). Target proteins were visualized using an EZ-ECL detection kit (Biological Industries).

RT-PCR Analysis of Thrombospondin-1 mRNA Transcription During Apoptosis:

Total RNA was isolated from apoptotic cells using the EZ-RNA isolation kit (Biological Industries), according to the manufacturer's protocol. Single-stranded cDNA was then synthesized from 2 micrograms of the isolated RNA using the superscript preamplification system for first-strand cDNA synthesis, according to the manufacturer's instructions. PCR analysis of thrombospondin-1-specific cDNA was performed using the thrombospondin-1-specific primers: 5'-GAGTCTGGCGGAGACAACAGC (SEQ ID NO: 1); and 5'-TTCCTGCACAAACAGGGTGAT (SEQ ID NO: 2). The primers were optimized using a specific cloned DNA as well as the temperature gradient cycler (BioMetra, Goettingen, Germany). Relative gene expression levels were adjusted based on beta-actin intensity, using the beta-actin specific primers 5'-ATGGTGGGAATGGGTCAGAAG (SEQ ID NO: 3) 5'-CACGCAGCTCATTGTAGAAGG (SEQ ID NO: 3). Thrombospondin-1- and beta-actin-specific primers were obtained from Sigma-Aldrich.

Thrombospondin-1/Thrombospondin-1 Receptor Inhibition Assays:

Immature dendritic cells were treated with thrombospondin-1-inhibitory antibodies and with various thrombospondin-1 receptors or thrombospondin-1 motifs, prior to addition thereto of thrombospondin-1 and/or apoptotic monocytes. Endocytosis of FITC-labeled latex beads (Sigma-Aldrich), either in the absence or presence of exogenous thrombospondin-1, was used as a control for endocytosis. Blocking antibodies against thrombospondin-1 receptors or thrombospondin-1 were used at 10 micrograms per milliliter. The blocking antibodies used were: mouse anti-human CD47 monoclonal antibody (clone B6H12.2; Neomarkers, Fremont, Calif., Cat. No. #MS-1302-P1ABX); mouse anti-CD51/integrin alphaV monoclonal antibody (clone AV1; Chemicon International, Cat. No. MAB2021Z); mouse anti-human CD29/beta1 integrin monoclonal antibody (clone P4C10; Chemicon International; Catalog No. MAB1987Z); mouse IgM anti-human CD36 monoclonal antibody (clone SMO; Serotec, Oxford, UK, Cat. No. MCA722XZ); anti-thrombospondin-1 type 1 repeat monoclonal antibody (clone A4.1; Biomeda, Foster City Calif., US); and azide-free polyclonal goat anti-human thrombospondin-1 N-terminus antibody [N-20; for binding to thrombospondin heparin-binding domain (HBD); Santa Cruz Biotechnology Inc., Cat No. sc-12312, Santa Cruz Calif., U.S.]. For isotype/negative control, azide free mouse IgG1 antibody was used (Serotec, Cat. No. MCA928XZ).

Statistics:

Statistical comparisons of mean data were performed using one-way analysis of variance (ANOVA) and the Students t-test with Bonferroni correction for multiple comparisons. The Student's t-test was also used to compare endocytosis, and to compare the expression of surface molecules on dendritic cells.

Experimental Results:

Serum-Withdrawal Treatment of Monocytes Yields a Homogeneous Apoptotic Population with Minimal Incidence of Necrosis:

The present inventors have previously shown that iC3b-opsonized apoptotic Jurkat cells induce immune suppression and generate tolerogenic dendritic cells (Verbovetski et al., 2002). In order to examine the physiological relevance of these findings, and due to the special role that monocyte apoptosis might have on antigen-presenting cell maturation (Albert et al., 1998), experiments were performed to determine whether apoptotic monocyte-induced immune suppression exists in an autologous primary cell system. Various apoptotic pathways of peripheral blood monocytes were analyzed and it was found that, after induction of surface-adherence, serum-withdrawal treatment was the most controlled and reproducible method for inducing monocyte apoptosis. Serum-withdrawal treatment for a duration of 12 hours resulted in 70 percent of treated cells displaying an early apoptotic phase, and a minimal proportion of necrotic cells (FIG. 1). Since maximal apoptosis and minimal necrosis was observed at 10-12 hours following the start of serum-withdrawal, these conditions were used in all experiments for apoptosis induction, unless indicated otherwise.

Figure 2B:
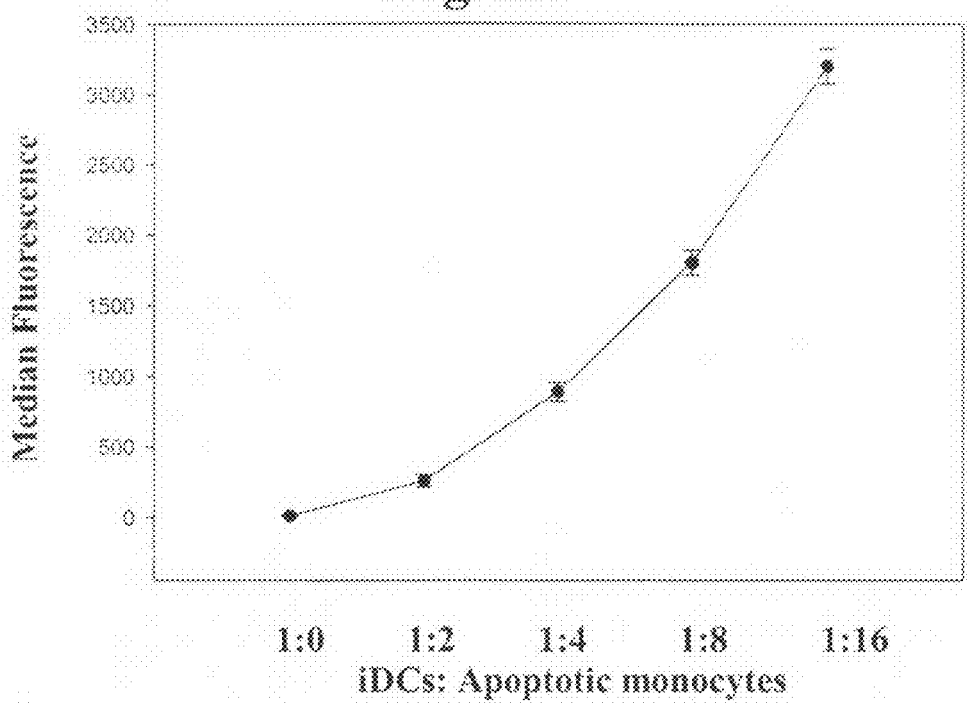
FIG. 2b is a line graph depicting endocytosis of DiI-stained apoptotic monocytes by immature dendritic cells. DiI-stained apoptotic monocytes were interacted with immature dendritic cells in triplicate at the indicated ratios. Note that DiI acquisition by immature dendritic cells was proportional to the number of interacting apoptotic cells, therefore immature dendritic cell acquisition of DiI was proportional to the number of interacting apoptotic cells.
Figure 2C:
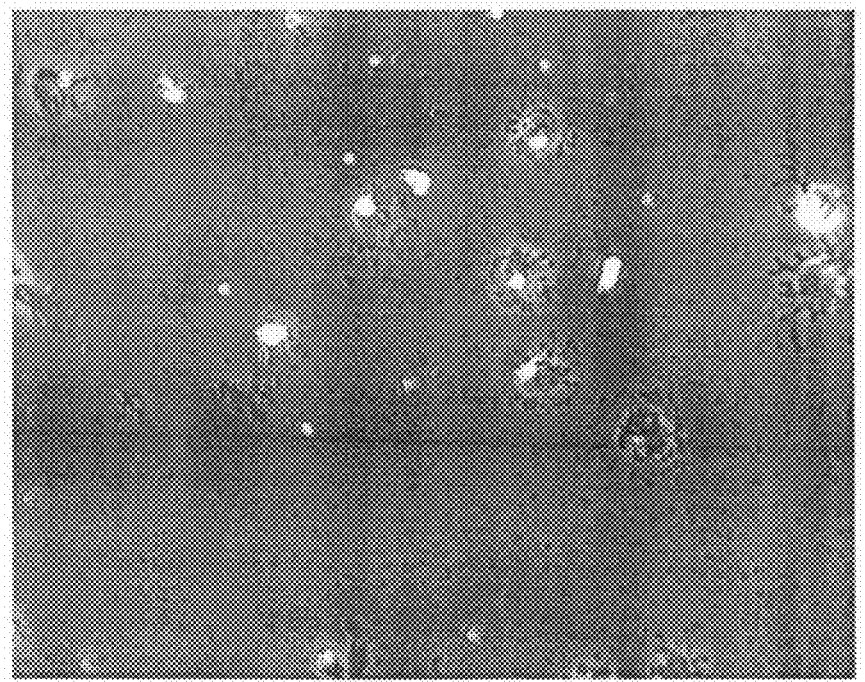
FIG. 2c is a fluorescence confocal micrograph depicting internalization of DiI-labeled apoptotic monocytes by immature dendritic cells (×40 original magnification).
Figure 2D:
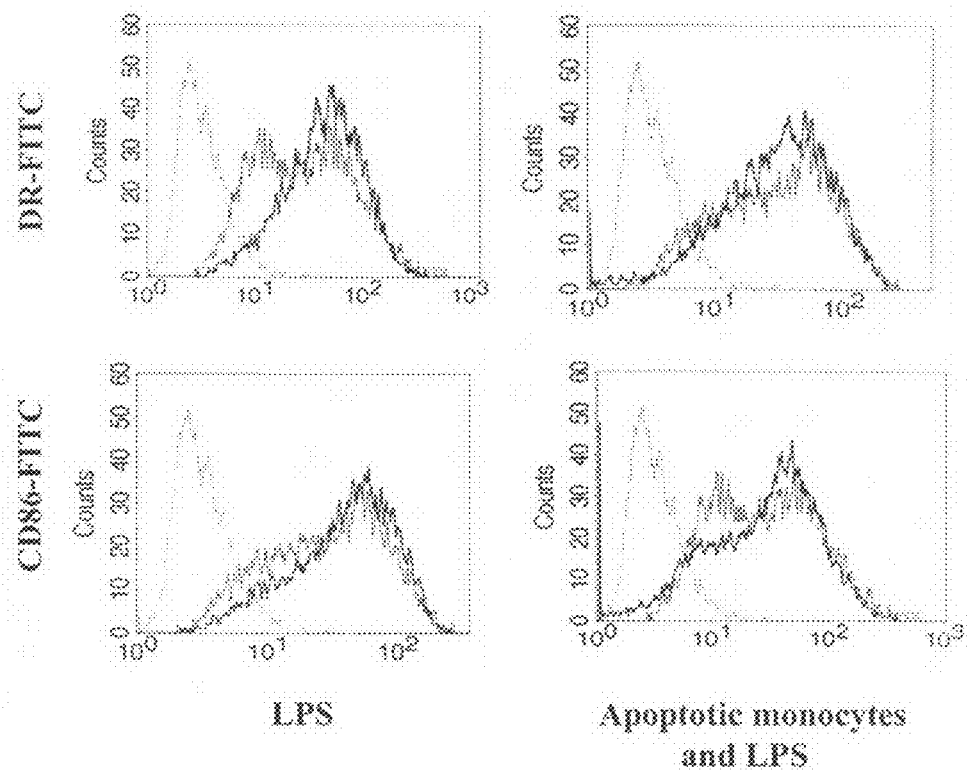
FIG. 2d is a set of FACS histograms depicting that apoptotic monocyte endocytosis downregulates the expression of maturation-related molecules on dendritic cells. Immature dendritic cells were treated with 5 nanograms per milliliter lipopolysaccharide (LPS) without (left panels) or with (right panels) interaction with apoptotic monocytes (at a ratio of 1:4). Stainings with FITC-conjugated DR (DR) antibody (upper panels) and FITC-conjugated anti-CD86 antibody (lower panels) are shown. HLA-DR and CD86 are expressed at baseline levels in immature dendritic cells (black trace) and are upregulated following treatment with LPS alone (left panels, bold trace). If exposed for 5 hours to apoptotic monocytes in the presence of LPS (right panels) upregulation of HLA-DR and CD86 surface display is inhibited (right panels, bold traces). Isotype control is represented by the grey trace in all histograms. The data shown represents five different experiments.
Figure 2E:
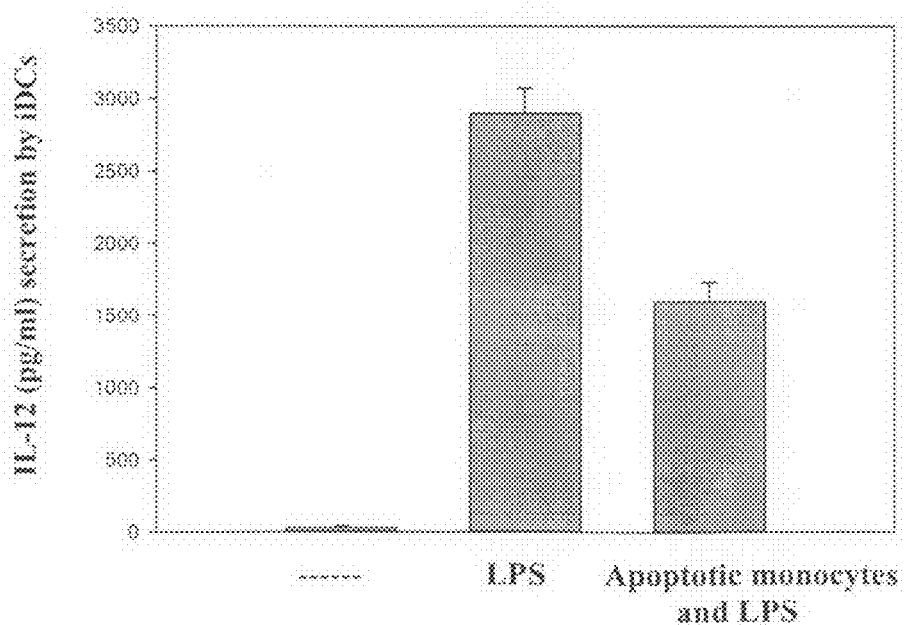
FIG. 2e is a histogram depicting that apoptotic monocyte endocytosis decreases IL-12 p40 production by dendritic cells treated with LPS. Immature dendritic cells secrete IL-12 in response to LPS. Following interaction with apoptotic cells in the presence of LPS, downregulation of IL-12 secretion is observed. Data is represented as mean plus/minus standard deviation of six experiments.
Figure 2F:
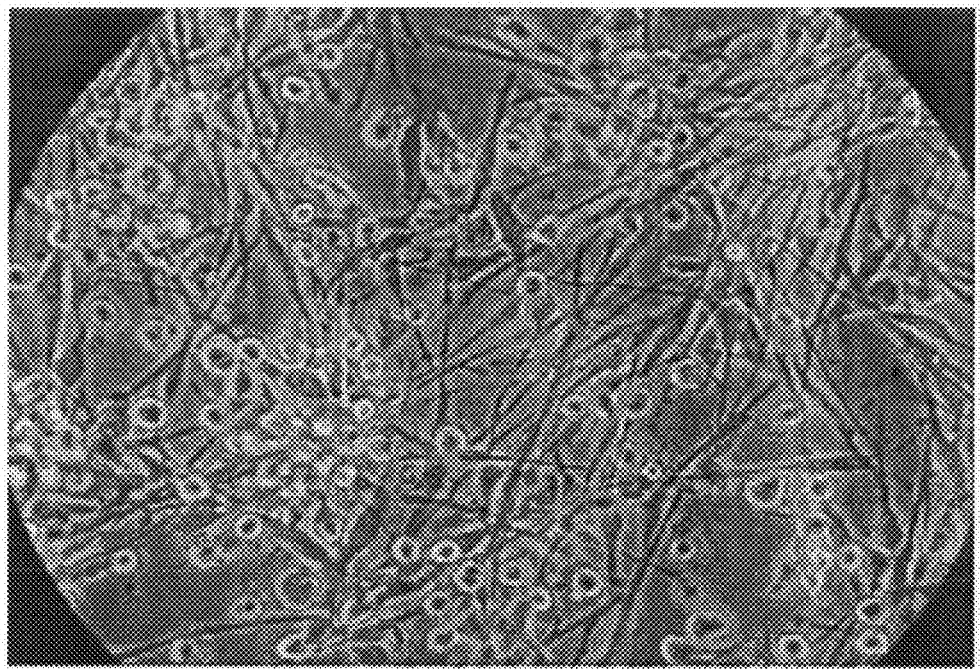
FIGS. 2f-g are fluorescence micrographs depicting that apoptotic monocytes prevent appearance of mature dendritic cell morphology in response to LPS. Immature dendritic cells change morphology, becoming elongated and more "dendritic", as they transform into mature dendritic cells in response to LPS treatment alone (FIG. 2f). Following interaction with apoptotic cells, immature dendritic cell morphology is retained despite concomitant treatment with LPS (FIG. 2g). Data is representative of five different experiments.
Figure 2G:
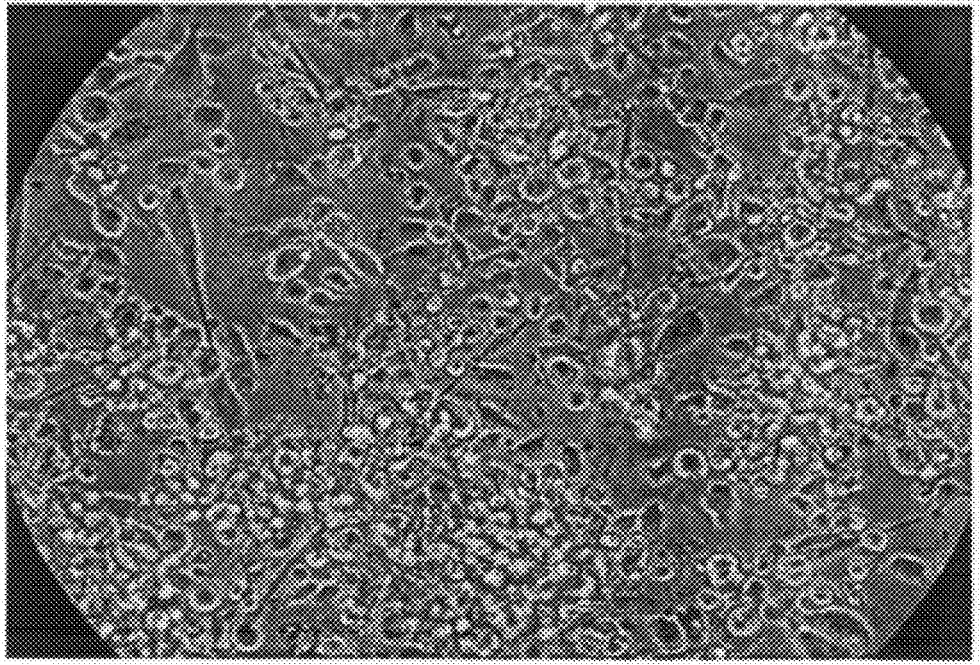

Endocytosis of Apoptotic Monocytes Inhibits Differentiation of Immunostimulatory/Mature Dendritic Cells:

Experiments were performed in order to verify whether immunostimulatory differentiation/maturation of immature dendritic cells is inhibited following endocytosis of autologous apoptotic monocytes, as has previously been shown by the present inventors via apoptotic Jurkat cells (Verbovetski et al., 2002). To estimate the capacity of immature dendritic cells to endocytose apoptotic monocytes, immature dendritic cells were mixed with DiI-stained apoptotic monocytes, and DiI uptake by the immature dendritic cells was quantified using a FACScan flow cytometer. Endocytosis was indeed shown to occur, as shown via a linear correlation between interaction ratios and signal intensity (FIGS. 2a and 2b) and confocal microscopic analysis (FIG. 2c). Failure of immature dendritic cells to exhibit immunostimulatory differentiation following interaction with apoptotic monocytes in the presence of LPS (1-10 nanograms per milliliter), a classical and potent inducer of dendritic cell maturation, was similar to that shown for iC3b-opsonized apoptotic Jurkat cells (Verbovetski et al., 2002). Following interaction with apoptotic cells, immature dendritic cells exhibited both decreased expression of cell surface costimulatory molecules and MEC class II (FIG. 2d), exhibited low levels of IL-12 production (FIG. 2e) as compared to immature dendritic cells treated with LPS only, and failed to display the characteristic morphology of mature dendritic cells (FIGS. 2f-g). Taken together, these findings demonstrate that, much like iC3b-opsonized apoptotic Jurkat cells, interaction of apoptotic monocytes with immature dendritic cells inhibited immunostimulatory differentiation/maturation of the latter.

Immunosuppression associated with apoptotic cells has generally been attributed to be mediated by dendritic cells following their endocytosis of the apoptotic cells (Fadok et al., 1998; Huang et al., 2000; Stuart et al., 2002; Verbovetski et al., 2002). However, experiments were performed in order to determine whether cells, such as monocytes actively generate and secrete molecules, upon apoptosis, that are capable of mediating immunosuppression independently of dendritic cells.

Figures 3A, 3B:
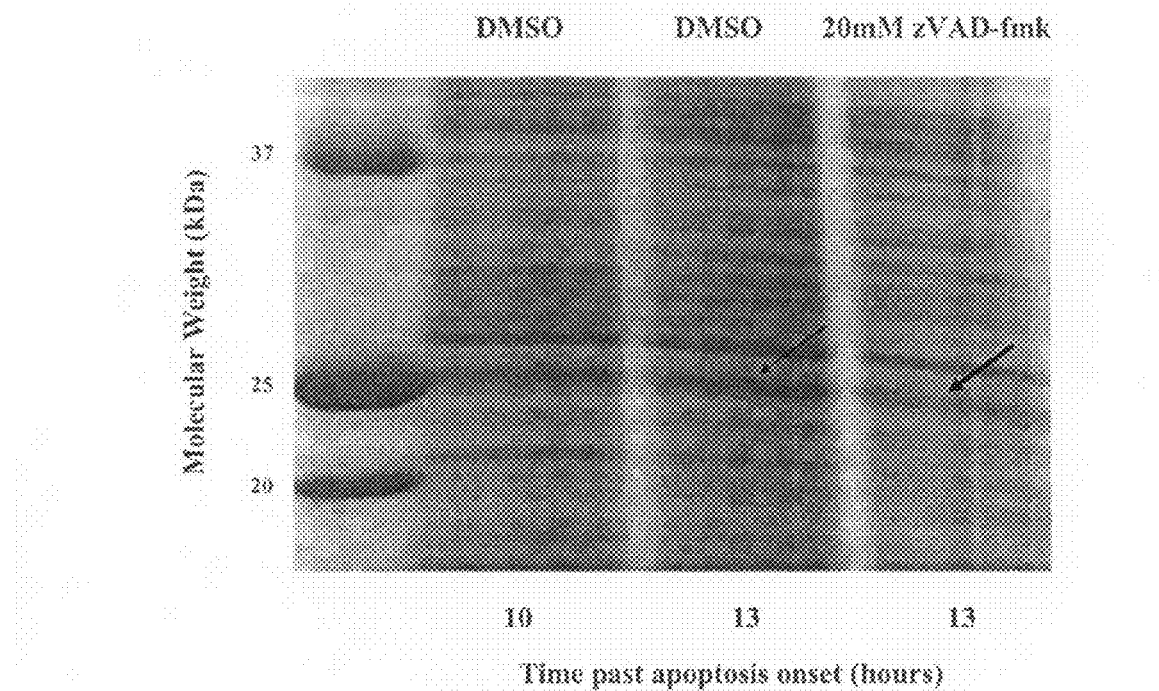
FIG. 3a is a photograph of an SDS-PAGE analysis depicting that a 26-kDa protein species is specifically secreted by apoptotic monocytes. Lanes show protein from supernatants collected from cultures of 30 million monocytes following serum-withdrawal induced apoptosis, with or without treatment with 20 millimolar pan caspase inhibitor zVAD-fmk, for the times indicated. Protein preparations were electrophoretically separated in 4-20 percent gradient polyacrylamide gels at 15 milligrams total protein per lane. After electrophoresis, the gels were stained with colloidal Coomassie Blue. An apoptosis-specific 26 kDa protein species (arrows) was secreted by the cells. Apoptosis-specificity of secretion is shown by the significant decrease of levels of the protein species in the presence of pancaspase inhibitor Zvad-FMK.
FIG. 3b is an amino acid sequence diagram depicting that the 26 kDa protein species specifically secreted by apoptotic monocytes corresponds to the 232 amino acid-long, N-terminal, heparin-binding domain (HBD) of TSP-1 (SEQ ID NO: 5). The full sequence shown corresponds to the heparin-binding domain, with the sequences of peptides of the 26 kDa domain identified via mass spectrometry are underlined.

Apoptotic Monocytes Secrete Thrombospondin (TSP)-1:

Proteins secreted by monocytes following serum withdrawal-induced apoptosis with or without concomitant treatment with zVAD-fmk were analyzed by SDS-PAGE and compared, and a 26 kDa protein species specifically secreted by the apoptotic cells was identified (FIG. 3a). The 26 kDa protein species was analyzed by mass spectrometry (MS), and was surprisingly found to correspond to the 232 amino acid, N-terminal, heparin-binding domain (HBD) of thrombospondin-1. The amino acid sequences (SEQ ID NO: 5) of the heparin-binding domain, and of the peptides identified by mass spectrometry leading to identification of the 26 kDa protein species as the heparin-binding domain (all included within N-terminal amino acid residues 1-228 of the heparin-binding domain) are shown in FIG. 3b. Secretion of the heparin-binding domain by apoptotic cells was unexpected since it had previously been shown to be cleaved and released only upon platelet aggregation (Elzie et al., 2004), and had only been thought to mediate cell-cell adhesion. The integral thrombospondin-1 molecule is a homotrimeric glycoprotein of approximately 145 kDa per subunit which was first described as a platelet alpha-granule protein that is released upon activation (Baenziger et al., 1971). The complete thrombospondin-1 molecule has been suggested to mediate cell-matrix and cell-cell activities through multiple receptors (reviewed by Adams, 2001), to act as a mediator of apoptotic cell endocytosis (Savill et al., 1992; Moodley et al., 2003), and to be secreted by macrophages and dendritic cells (Savill et al., 1992; Doyen et al., 2003), fibroblasts (Moodley et al., 2003), and other cell types (Adams, 2001).

Figure 4A:
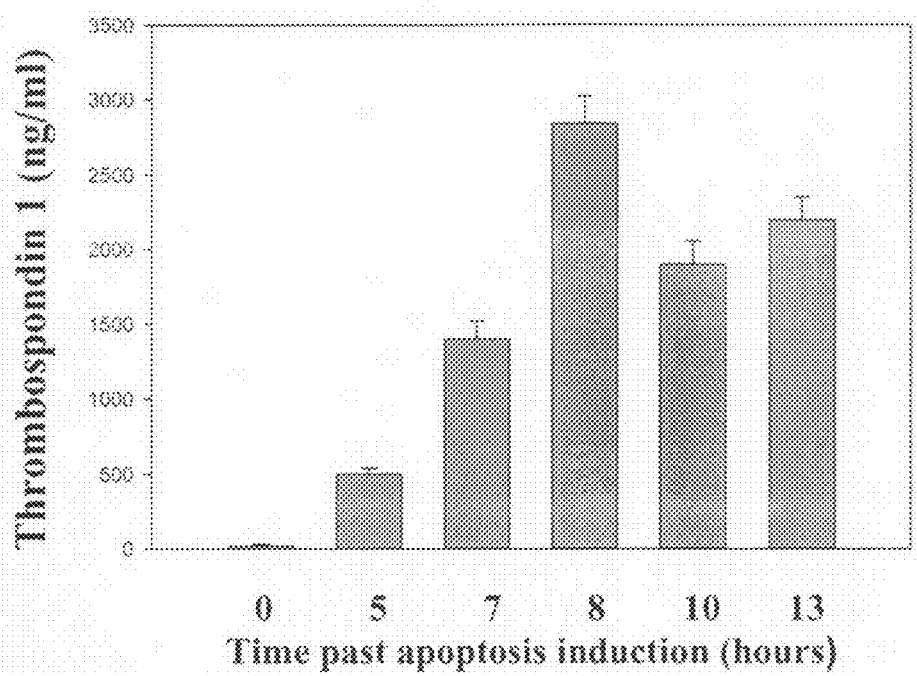
FIG. 4a is a histogram of an immunoenzyme assay depicting that timing of thrombospondin-1 secretion by apoptotic monocytes correlates with timing of early apoptosis induction. Shown are thrombospondin-1 protein concentrations in apoptotic monocyte culture supernatants, at the indicated times following apoptosis induction. The highest thrombospondin-1 levels were found between 8-13 hours following induction, and corresponded to early apoptosis as shown in FIG. 1.

To confirm the correlation between apoptosis and thrombospondin-1 secretion, secreted thrombospondin-1 levels were examined via enzyme immunoassay. As shown in FIG. 4a, thrombospondin-1 protein concentration in apoptotic monocyte culture medium was shown to rise along with apoptosis progression, reach a plateau, and then gradually decrease after eight hours.

Figure 4B:
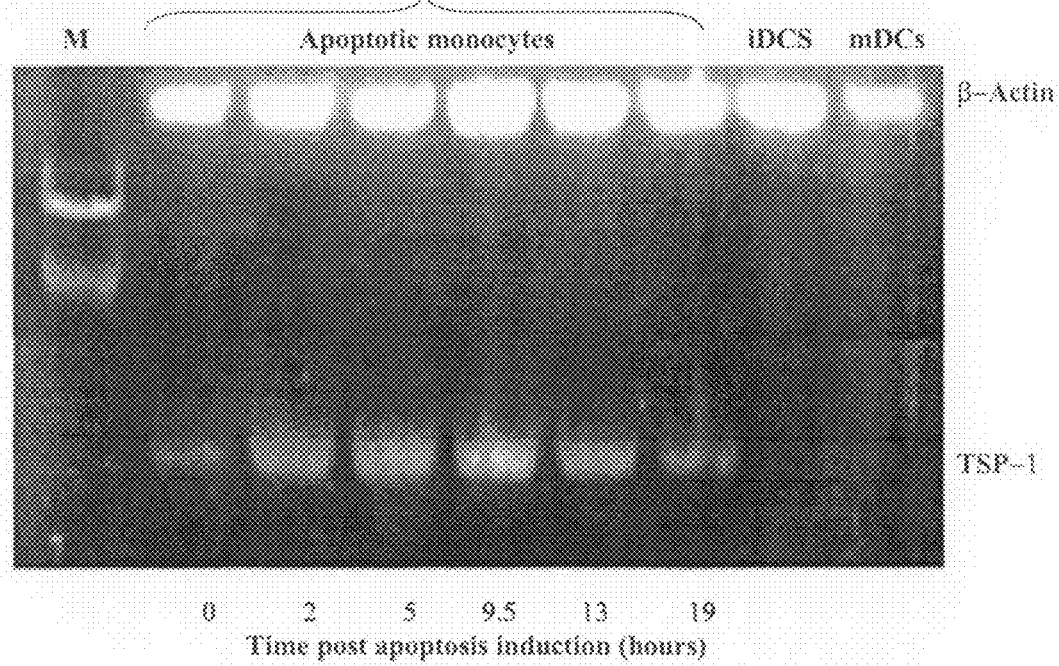

Serum-Withdrawal Treatment Induces De-Novo Thrombospondin-1 Synthesis:

As apoptosis induction conditions were chosen that yield a minimal portion of necrotic cells (see FIG. 1), it was assumed that thrombospondin-1 was not detected in culture supernatants as a result of leakage from the cytosol due to loss of membrane integrity in necrotic cells, but rather that thrombospondin-1 was actively secreted during early apoptotic phase. Experiments were performed to determine whether thrombospondin-1 is secreted from readily available pools due to the apoptotic process, or is rather synthesized de-novo upon induction of apoptosis. As shown in FIG. 4a, a gradual increase in supernatant content of thrombospondin-1 correlated with the apoptotic process. Furthermore, lysates of viable monocytes did not contain thrombospondin-1, indicating that pre-apoptotic cells did not contain cytosolic thrombospondin-1. Thrombospondin-1 mRNA transcription kinetics were also tested using RT-PCR. As shown in FIGS. 4b-c, thrombospondin-1 mRNA levels rose upon induction of apoptosis, and peaked after 10 hours. Thus, despite being in the process of cell death, apoptotic monocytes actively synthesized mRNA for de-novo generation of thrombospondin-1. In contrast, thrombospondin-1 mRNA levels were low in viable monocytes. In order to further verify the results of thrombospondin-1-related transcriptional activity, Western blot analysis of cell lysates and culture supernatants for intracellular and secreted thrombospondin-1, respectively, was performed.

In accordance with mRNA levels, intracellular protein levels were undetectable in viable monocytes, and were elevated upon generation of apoptosis (FIG. 4d). As shown in FIG. 4c, and in accordance to the mass spectrometry findings, the cleaved heparin-binding domain was found only in the culture medium, whereas intracellular thrombospondin-1 remained intact.

Figure 5A:
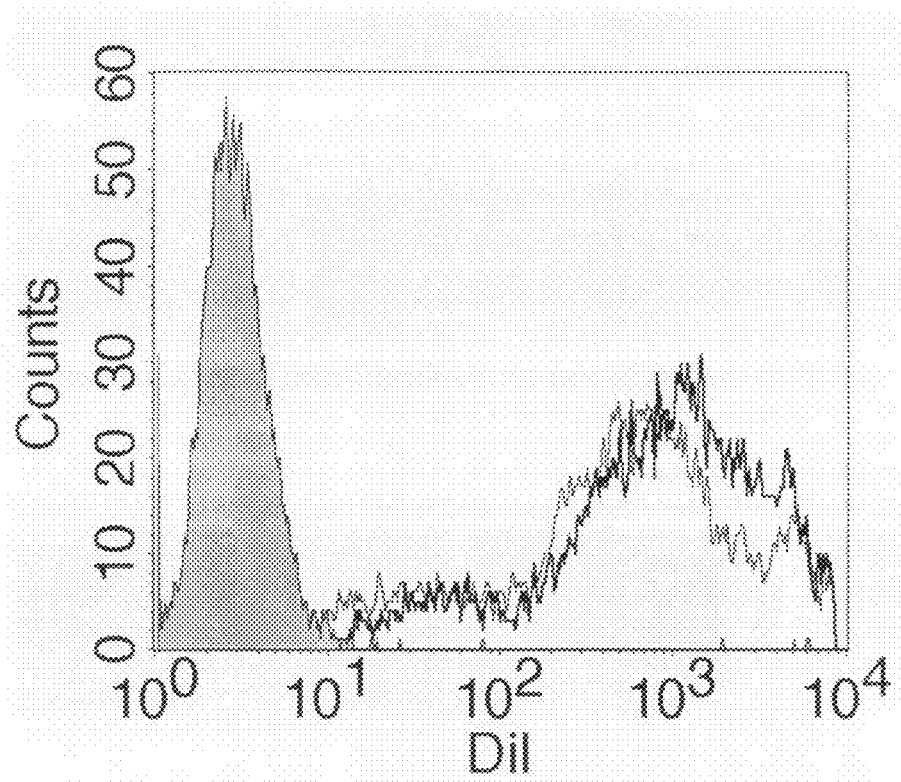
FIG. 5a is a FACS histogram depicting that thrombospondin-1 enhances apoptotic monocyte endocytosis by immature dendritic cells. Monocytes were stained with DiI and were interacted with immature dendritic cells at a 1:4 ratio. Immature dendritic cells that were not interacted with apoptotic monocytes (gray filled curve), did not acquire DiI and were not stained, but immature dendritic cells that were interacted with DiI-stained apoptotic monocytes acquired DiI staining (black trace). Addition of 2 micrograms per milliliter exogenous thrombospondin-1 (bold trace) significantly increased median fluorescence from 578 (in the absence of thrombospondin-1) to 922 (in the presence of thrombospondin-1), indicating that interaction was increased by 59.6 percent (p less than 0.0001). Results are representative of five experiments.
Figure 5B:
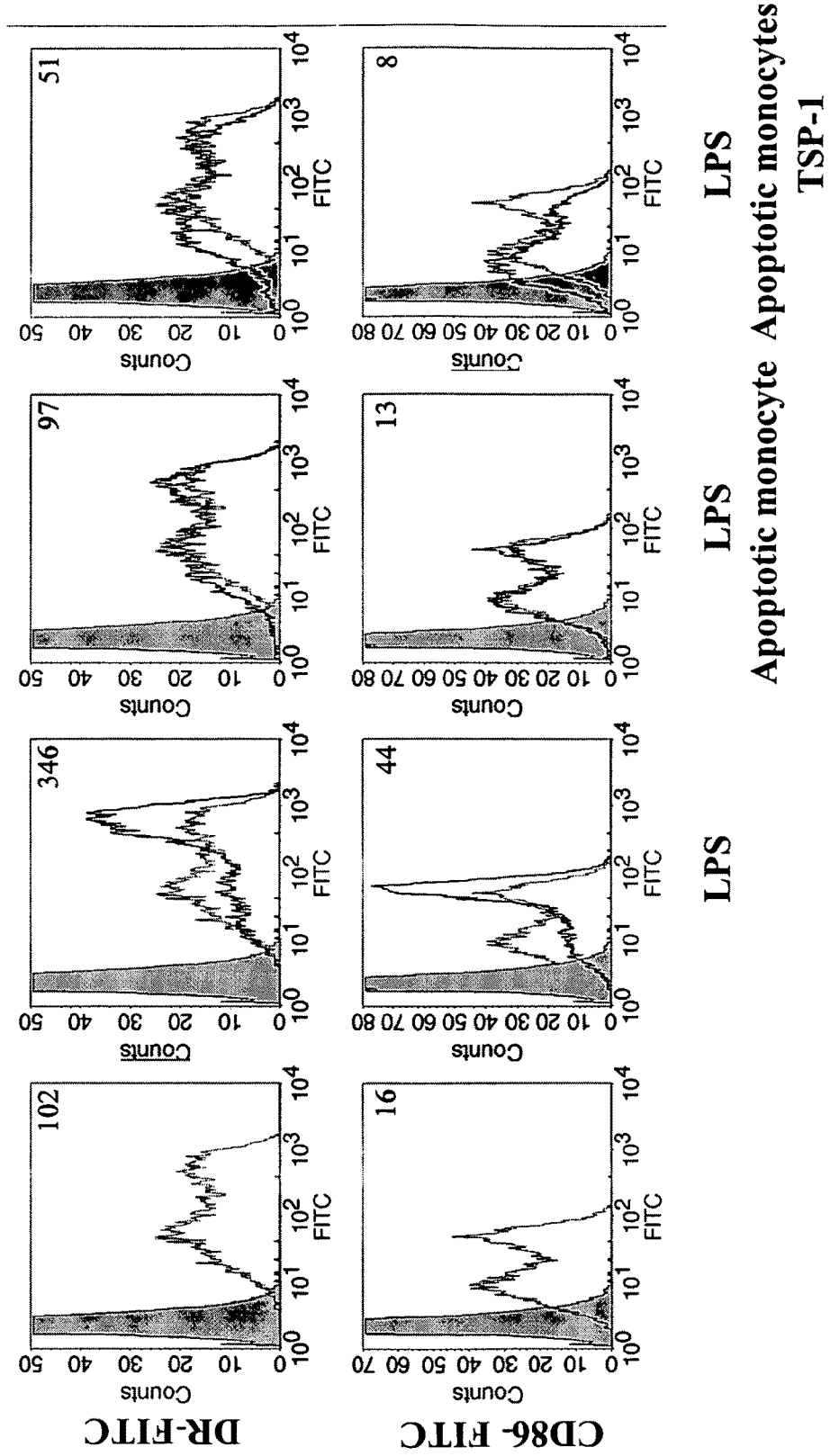
FIG. 5b is a set of FACS histograms depicting that immature dendritic cell maturation is inhibited by thrombospondin-1 in the presence of apoptotic monocytes. Immature dendritic cells (black trace) exhibited increased surface expression of the dendritic cell maturation markers HLA-DR (DR) and CD86 following treatment with 5 nanograms per milliliter of LPS, an inducer of dendritic cell maturation (bold trace). As was shown in FIG. 2c, marked downregulation of CD86 and HLA-DR (DR) surface expression was documented (p less than 0.0001) in the presence of apoptotic monocytes. Addition of 2 micrograms per milliliter thrombospondin-1 further inhibited HLA-DR and CD86 surface expression and was significantly superior to that observed in apoptotic monocytes alone (p less than 0.001). Numbers indicating the median fluorescence are presented in each histogram. Analysis was made using FITC-conjugated anti-HLA-DR antibody (upper panel) and FITC-conjugated anti-CD86 antibody (lower panel). Isotype control is shown as gray filled curves.

Thrombospondin-1 Improves Endocytosis and Induces Immunosuppression In Immature Dendritic Cells:

Experiments were then performed to determine whether thrombospondin-1 can account for the observed endocytosis, immunosuppression, or both. Immature dendritic cells were incubated with prewashed apoptotic monocytes, to either with or without the addition of exogenous thrombospondin-1. The thrombospondin-1 concentration chosen was 2 micrograms per milliliter, the same as the physiological concentration observed following 10 hours of monocyte apoptosis, as shown in FIG. 4a. Adding thrombospondin-1 to the interacting cell system improved immature dendritic cell endocytosis of apoptotic monocytes by 61 percent on average (three experiments, p less than 0.0001), with a mean fluorescence of 601 units in the absence of exogenous thrombospondin-1, and 960 units in the presence of thrombospondin-1 (FIG. 5a). Thrombospondin-1 also inhibited dendritic cell plasma membrane expression of maturation-related molecules CD86 and MHC class II (FIG. 5b), and decreased IL-12 production (not shown).

Figure 6A:
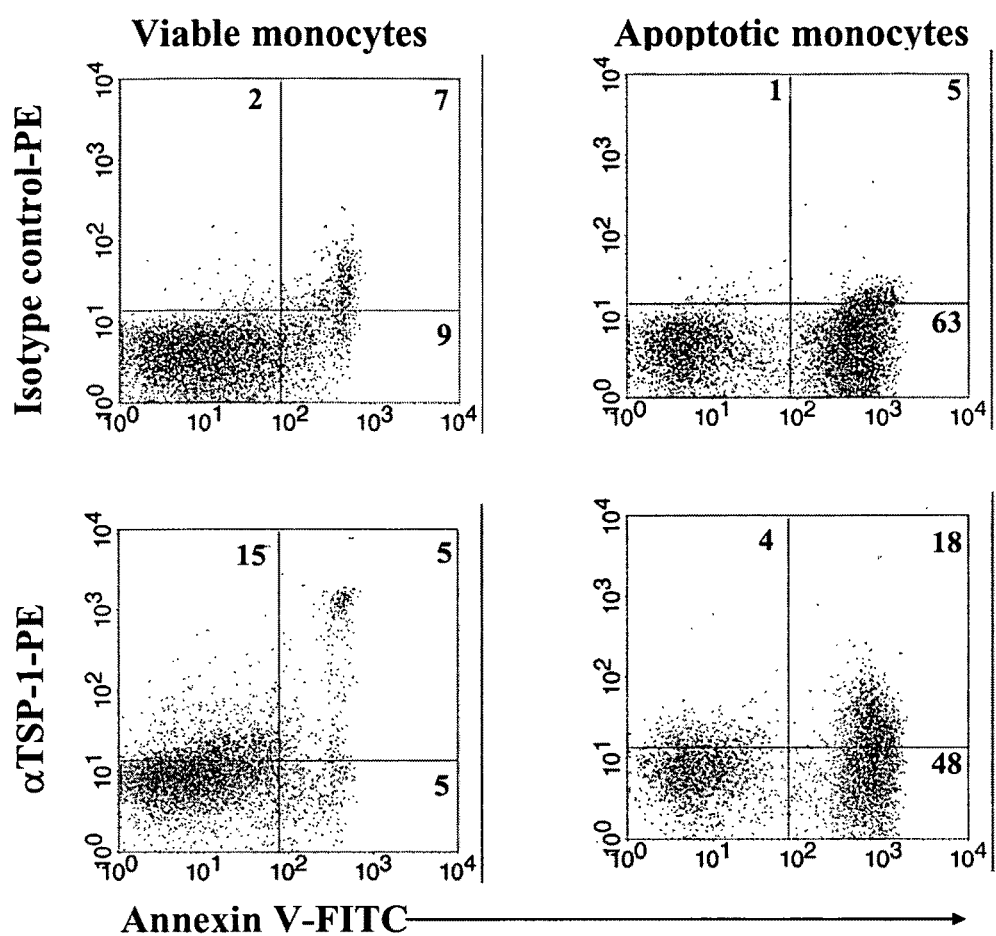
FIGS. 6a-c are FACS assay results showing that thrombospondin-1 scarcely binds to late apoptotic monocytes and binds strongly to immature dendritic cells. Monocytes (viable and apoptotic) and immature dendritic cells were washed twice with RPMI, and incubated for 30 minutes on ice with 10 micrograms per milliliter thrombospondin-1. Cells were then rewashed, and stained with anti-TSP1 antibody (Biomeda), by fluorescence-labeled secondary antibody and with either FITC-labeled annexin-V or propidium iodide.
Figure 6B:
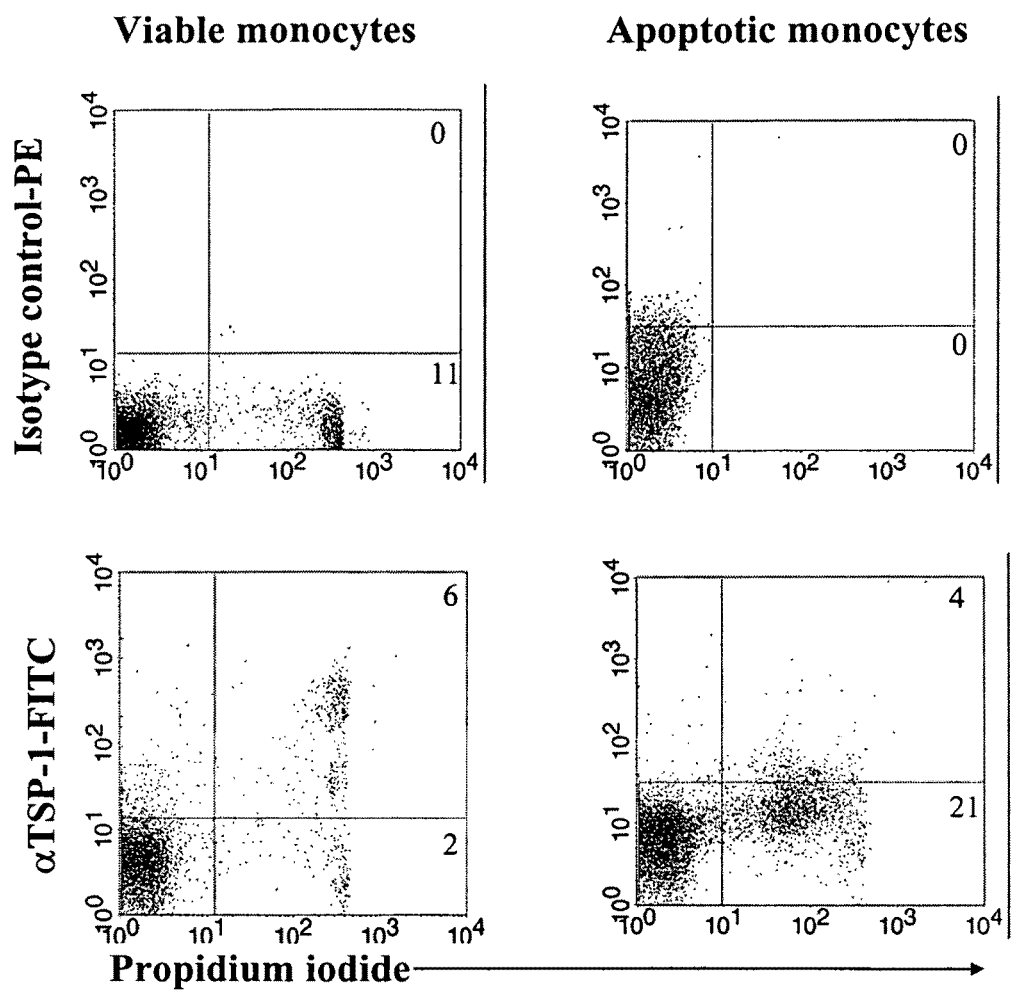
Figure 6C:
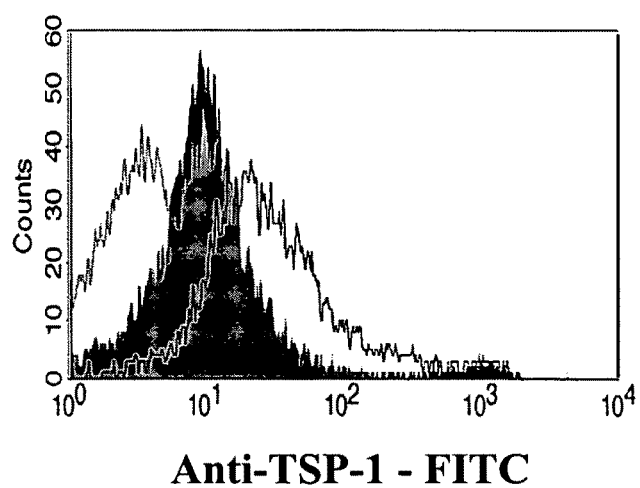

Thrombospondin-1 Binds to Immature Dendritic Cells, but Scarcely Binds to Apoptotic Monocytes:

Thrombospondin-1 has previously been suggested to function as a bridging molecule between apoptotic cells and macrophages, thereby increasing apoptotic cell endocytosis (Savill et al., 1992). In order to determine whether thrombospondin-1 plays a similar role in the presently described model, experiments were performed to determine whether thrombospondin-1 binds to both apoptotic monocytes and immature dendritic cells. Purified thrombospondin-1 was added to pre-washed apoptotic monocytes and immature dendritic cells, and cell surface-bound thrombospondin-1 was measured using a FACScan flow cytometer using anti-thrombospondin-1 monoclonal antibody directed against type I repeats of thrombospondin-1 (clone A4.1). Surprisingly, only scant binding to annexin-V positive monocytes was observed (FIG. 6a), and was confined to propidium iodide-positive cells (FIG. 6b). In contrast, intense binding of thrombospondin-1 to immature dendritic cells was observed (FIG. 6c).

Figures 6D, 6E, 6F:
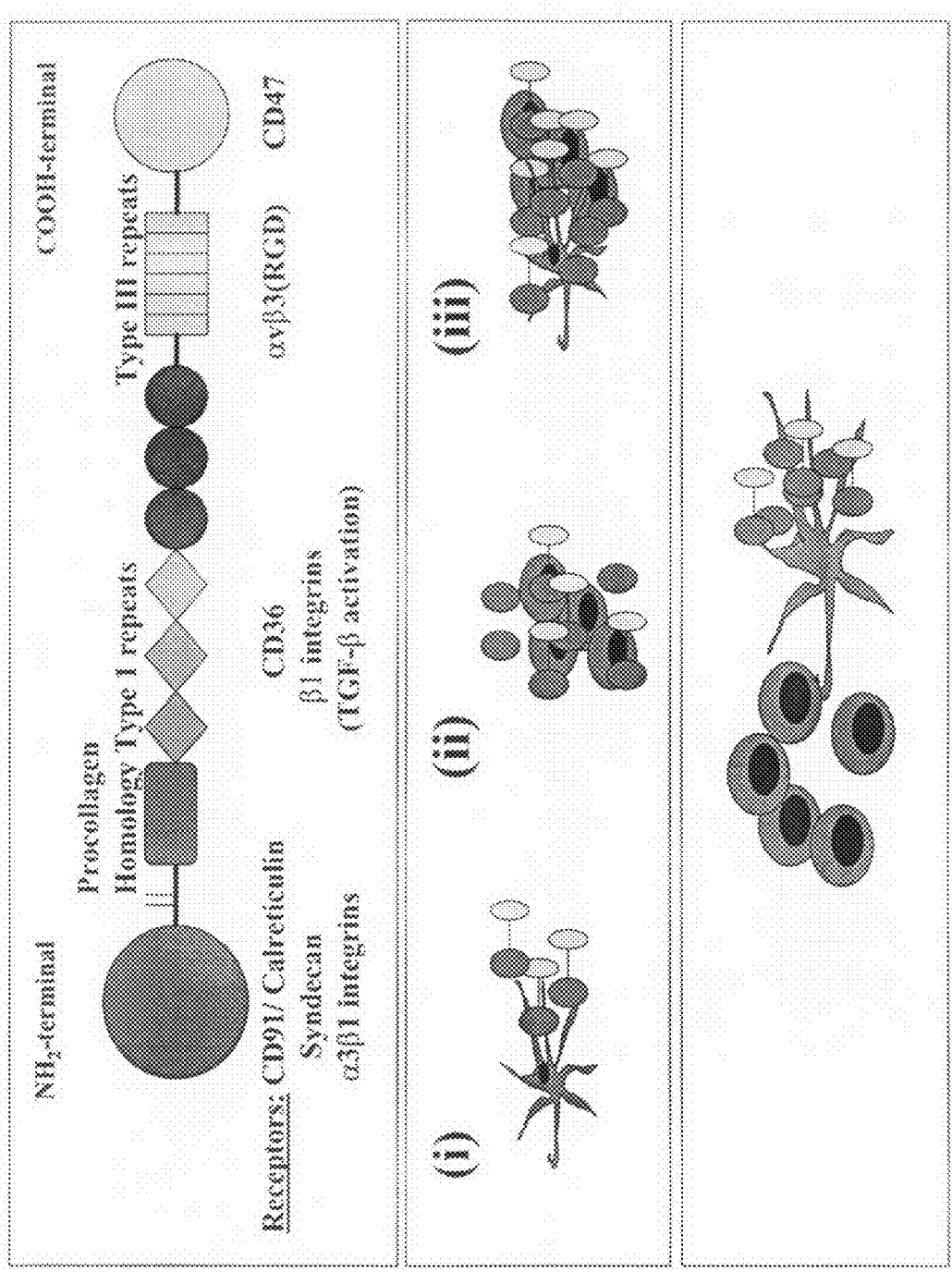
FIGS. 6d-f are schematic diagrams depicting proposed mechanisms of binding of thrombospondin-1.

Therefore, it can be concluded that the proposed classical bridging role of thrombospondin-1 as a factor increasing endocytosis of apoptotic cells may be realized more strongly following binding to immature dendritic cells, and less dominantly following binding to apoptotic cells. Alternatively, it is possible, as shown here, thrombospondin-1 may mediate its function by directly affecting immature dendritic cells, and not necessarily following endocytosis of apoptotic cells (FIGS. 6d-f).

Figure 7A:
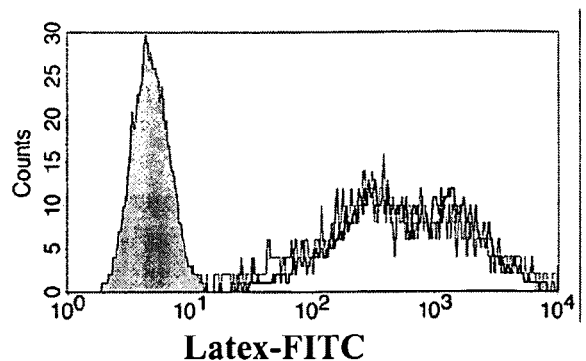
FIG. 7a is a FACS histogram depicting that thrombospondin-1, by itself, enhances endocytosis by immature dendritic cells. Green fluorescent protein (GFP)-coupled latex beads were mixed with immature dendritic cells at a 15:1 ratio, in the presence of 2 micrograms per milliliter (bold trace) or zero micrograms per milliliter (black trace) exogenous thrombospondin-1. The gray-filled curve represents immature dendritic cells that were not mixed with beads. Median fluorescence was 395 units in the absence, and 538 units in the presence, of thrombospondin-1, indicating 36 percent augmentation of phagocytic capacity (p less than 0.001).
Figure 7B:
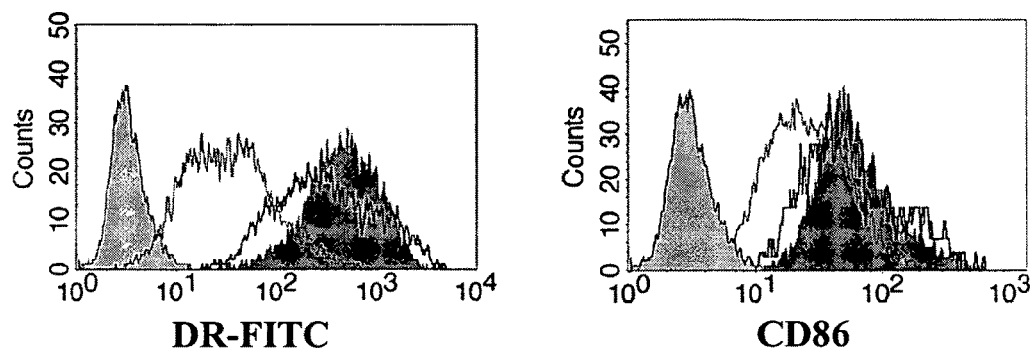
FIG. 7b is a pair of FACS histograms depicting that thrombospondin-1 by itself inhibits immature dendritic cell maturation. Immature dendritic cells (black trace) were treated with 5 nanograms per milliliter LPS in the absence (dark-filled curve) or presence (bold trace) of 1 microgram per milliliter thrombospondin-1, or remained untreated (dark thin line), and were analyzed for surface display of the maturation specific markers HLA-DR (DR; left panel) or CD86 (right panel). The bright filled curve represents isotype control.

Thrombospondin-1-Mediated Endocytosis is Mediated Via the Heparin-Binding Domain:

Experiments were performed to analyze whether thrombospondin-1 alone can account for immature dendritic cell enhancement of endocytosis and the observed tolerogenic profile, or whether apoptotic monocytes must also be present. To this end, thrombospondin-1-treated immature dendritic cells were incubated with green fluorescent latex beads and their endocytosis was assessed via FACS. As seen in FIG. 7a, endocytosis of the latex beads by the immature dendritic cells increased by 35.7 plus/minus 3.5 percent over control in the presence of thrombospondin-1, compared with a 71.5 plus/minus 5.2 percent increase in apoptotic monocyte endocytosis. Thus, an increased, non-specific endocytosis capacity has been observed, which was significantly more pronounced for endocytosis of apoptotic cells. Furthermore, the resulting dendritic cells displayed an immature phenotype (FIG. 7b), even in the absence of apoptotic monocyte endocytosis. Adding thrombospondin-1 alone to immature dendritic cells, decreased immature dendritic cell maturation level (not shown).

It can be concluded from the presently disclosed experimental data that thrombospondin-1 increases the endocytosis capacity of immature dendritic cells, and has the capacity to induce the generation of tolerogenic dendritic cells, even in the absence of apoptotic cells.

In order to explore the mechanisms underlying the above observations, experiments were performed to elucidate the exact sites for thrombospondin-1 binding that mediate these effects, focusing on known thrombospondin-1 receptors. For this, inhibition assays were carried out by treating immature dendritic cells with inhibitory antibodies directed to several thrombospondin-1 receptors or thrombospondin-1 domains, prior to treatment of immature dendritic cells with thrombospondin-1, with or without interaction with apoptotic monocytes. While treatment of immature dendritic cells with blocking anti-CD36 antibody prior to interaction significantly decreased apoptotic monocyte endocytosis, treatment with an antibody against the heparin-binding domain decreased endocytosis even further, almost to the basal level of thrombospondin-1-mediated endocytosis. In contrast, treatment with antibody specific for CD29/beta1 integrin, or antibody specific for CD47, a ligand of the C-terminal portion of thrombospondin-1, had no significant influence on endocytosis, and addition of anti-CD51/alphaV integrin antibody only slightly inhibited apoptotic monocyte endocytosis (FIG. 8a).

Blocking Antibodies Specific for the Thrombospondin-1 Heparin-Binding Domain, or Specific for its Receptor CD29, Optimally Inhibit Thrombospondin-1-Mediated Inhibition of Differentiation of Immunostimulatory/Mature Dendritic Cells:

The mechanisms of thrombospondin-1-mediated inhibition of immunostimulatory differentiation/maturation of dendritic cells were investigated using blocking antibodies specific for the thrombospondin-1 heparin-binding domain, or for the thrombospondin-1 receptors CD29/beta1 integrin, CD47, CD51/alphaV integrin, and CD36. Experiments were performed by treatment with blocking antibody alone or in conjunction with apoptotic cells. Surprisingly, optimal and almost complete inhibition of thrombospondin-1-mediated immature dendritic cell maturation was achieved by treatment with anti-heparin-binding domain antibody alone, and second-best inhibition was achieved by treatment with anti-CD29/beta1 integrin antibody alone, as determined via inhibition of cell surface display of the maturation markers HLA-DR (FIG. 8b) and CD86 (FIG. 8c).

Thus, the heparin-binding domain, interacting with immature dendritic cells, is the critical domain in regard to both endocytosis and immunosuppression mediated by such cells. As shown here for the first time, it is secreted by apoptotic monocytes and functions both as a pro-endocytotic signal, and as an optimal inhibitor of dendritic cell maturation.

These results further suggest that the interaction between thrombospondin-1, via its heparin-binding domain, and CD29/beta1 integrins may be essential for thrombospondin-1-mediated inhibition of differentiation of immunostimulatory/mature dendritic cells, in view of the capacity of the thrombospondin-1 heparin-binding domain to specifically bind various beta1 integrins (Krutzsch, H. C. et al., 1999. J. Biol. Chem. 274:24080-24086; Chandrasekaran, L. et al., 2000. Mol. Biol. Cell 11, 2885-2900; Calzada, M. J. et al., 2003. J. Biol. Chem. 278:40679-40687), and in view of the presently uncovered potent capacity of blocking antibodies against either heparin-binding domain or CD29 to inhibit thrombospondin-1-mediated inhibition of differentiation of immunostimulatory/mature dendritic cells. This finding was surprising since the heparin-binding domain of thrombospondin-1 had only been suggested to be involved in modulation of angiogenesis (Chandrasekaran, L. et al., 2000. Mol. Biol. Cell 11, 2885-2900), and cell adhesion (Krutzsch, H. C. et al., 1999. J. Biol. Chem. 274:24080-24086; Calzada, M. J. et al., 2003. J. Biol. Chem. 278:40679-40687), and had not been implicated in thrombospondin-1-mediated regulation of differentiation of immunostimulatory/mature dendritic cells.

Example 2

TSP-1 Regulates T-Cell Suppression

As described in Example 1, hereinabove, TSP-1-treated DCs displayed an immunoparalyzed phenotype (FIG. 7b), even in the absence of apoptotic monocyte engulfment. Adding only TSP-1 to immature dendritic cells (iDCs) decreased expression of iDC maturation molecules. To test whether this phenotype will indeed lead to T cell suppression, the mixed lymphocytic reaction (MLR) was used in the presence of LPS, as follows.

Materials and Experimental Methods

CFSE Labeling of Responder Cells for MLR Experiments—

T cell enriched fraction was prepared by adherence of mononuclear cells from healthy donors to tissue culture dishes and incubation for 1 hour to allow monocytes adhesion. Non-adherent cells were harvested, washed twice and resuspended in RPMI at a concentration of $1 \times 10^7$/ml. Immediately before labeling, 5 µM CFSE stock (Molecular probes) was thawed and diluted to 10 µM in a volume of RPMI equal to that in which the responder cells (i.e., the T cell enriched fraction) were suspended. The two equal volumes were mixed to initiate labeling and gently agitated for 10 minutes at room temperature. The labeling process was quenched by adding, for 1 minute, an equal volume of autologous (i.e., from the donor of cells) serum. The CFSE-labeled cells were then washed twice with RPMI containing 10% autologous serum, recounted and adjusted to a concentration of $1 \times 10^7$/ml in RPMI containing 20% autologous serum.

Mixed Lymphocytic Reaction (MLR) Culture— iDCs on day 6 of culture were exposed to either 10 ng/ml LPS for 18 hours or to 2 µg/ml TSP-1 for 5 hours followed by LPS (10 ng/ml) for 18 hours, or were left untreated. DCs from different treatments were harvested, washed and resuspended in RPMI containing 20% human serum at a concentration of $1 \times 10^7$/ml. $4 \times 10^5$ CFSE labeled T cells were plated in different ratios with DCs in RPMI containing 20% autologous serum in a final volume of 0.7 ml. The control experiments for assessing background fluorescence were set up by culture of labeled responder cells alone. On day 6 the cells were harvested and stained with CD3-PE and flow cytometry was performed on a FACScan. Data were analyzed using CEllQuest analysis software on CD3 positive cells only (the gates show only CD3 positive CFSE labeled cells, M1 in FIGS. 9a-f).

Experimental Results

Treatment of iDCs with TSP-1 Inhibits T Cell Activation in the Absence of Apoptotic Cells—

CFSE labeled T cells were co-cultured with different ratios of DCs which were treated with either LPS alone or which were exposed to TSP1 for 5 hour prior to LPS treatment. As can be seen in FIGS. 9a-f, exposure to TSP-1 prior LPS treatment inhibited DCs induced T cells activation by 27% at the 2:1 ratio between T cell and DC (T:DCs) and by 50% at the 4:1 ratio between T cell and DC ratio. Thus, these results demonstrate that incubation of DCs with TSP-1, in the absence of apoptotic monocytes, results in a successful suppression in the range of 30-50% of T-cell activation. These results therefore suggest the use of TSP-1 or heparin-binding domain (HBD) of TSP-1 for T cell suppression.

Discussion:

In the presently disclosed experiments, an unbiased proteomic approach was used to identify apoptosis-related secreted proteins that participate in endocytosis and immune suppression. Thrombospondin-1, a protein whose secretion has previously been ascribed mainly to the endocytosing cell, is presently identified for the first time as a protein that is synthesized de-novo by monocytes upon serum withdrawal-induced apoptosis.

Thrombospondin-1 is a calcium-binding protein that participates in cellular responses to growth factors, cytokines, and injury (for a review see Chen et al., 2000 and Adams, 2001). It regulates cell proliferation, migration, and apoptosis in a variety of physiological and pathological settings, including wound healing, inflammation, angiogenesis, and neoplasia. Thrombospondin-1 binds to a wide variety of integrin and non-integrin cell surface receptors (FIG. 6d). The binding sites for these receptors on thrombospondin-1 are dispersed throughout the molecule, with most domains binding multiple receptors. In some cases, thrombospondin-1 binds to multiple receptors concurrently, and recent data indicate that there is crosstalk between receptor systems. Thus, thrombospondin-1 may direct the clustering of receptors to specialized membrane domains for adhesion and signal transduction.

Although it has long been appreciated that thrombospondin-1 plays a role in mediating endocytosis of apoptotic cells, its source was mainly attributed to the endocytosing cell and its role was mainly attributed to facilitating endocytosis as a bridging molecule. The presently disclosed experimental results show for the first time that monocytes transcribe thrombospondin-1 mRNA and translate thrombospondin-1 protein de-novo upon apoptosis, and that thrombospondin-1 has a direct facilitating effect on endocytosis and immunosuppression. Until now, thrombospondin-1-mediated immunosuppression was attributed to interaction thereof only with CD47 (Doyen et al., 2003), the interaction being with the C-terminal domain of thrombospondin-1. It is presently demonstrated for the first time that the heparin-binding domain, which is an N-terminal portion of thrombospondin-1, serves as a potent ligand for mediating endocytosis and immunosuppression. The N-terminus of thrombospondin-1 and TSP-2, by virtue of its globular structure, has sequence similarity to the pentraxin superfamily, which has been associated with apoptotic cell clearance. Furthermore, the heparin-binding domain was shown to interact with calreticulin and CD91, which are related to apoptotic cell clearance in both mammals (Ogden et al., 2001) and C. elegans (Ellis et al., 1991; Zhou et al., 2001). The heparin-binding domain supports cellular adhesion (Murphy-Ullrich et al., 1993; Ferrari do Outeiro-Bernstein et al., 2002) and chemotaxis (Vogel et al., 1993; Calzada et al., 2003).

Given the findings of this and previous studies, the present inventors hypothesize that the proposed mechanism of action involves de-novo thrombospondin-1 synthesis by apoptotic monocytes and secretion of either intact thrombospondin-1 or of heparin-binding domain. It was not presently possible to document thrombospondin-1 generation by immature dendritic cells at the mRNA or protein level, as previously suggested (Doyen et al., 2003), but it is an additional possible mechanism (FIG. 6d). Thrombospondin-1 or heparin-binding domain then binds mainly to immature dendritic cells or endocytosing cells, forming both a bridging molecule and a signalosome that increase endocytotic capacity and mediate inhibitory signals, resulting in a tolerogenic immature dendritic cell phenotype. Apoptotic cells then bind, either via thrombospondin-1 and its relevant receptors; CD91/calreticulin/LRP, CD36, alphaVbeta3 integrin/vitronectin receptor, or via other the endocytosing cell-specific apoptotic cell receptors, such as phosphatydilserine receptor, CD11b/CD18 (if complement opsonization occurs), alphaVbeta5 integrin, or alphaVbeta3 integrin. Most important, this tolerogenic phenotype is acquired by immature dendritic cells, even in the absence of interaction with apoptotic cells, indicating the crucial role of the 26 kilodalton heparin-binding domain fragment of thrombospondin-1 (FIG. 6d).

The presently described mechanism also suggests the formation of multiprotein complexes at the cell surface, and the clustering of receptors that initiate signal transduction, such as the T-cell receptor signalosome (Werlen and Palmer, 2002). Interactions between apoptotic cells and immature dendritic cells show a dynamic structure with expanding complexity. However, as presently demonstrated here, the vast majority of the consequences of these interactions can be mediated by a single protein. This mechanism is not only important in homeostasis, but may also be a major mechanism for turning down inflammation and avoiding autoimmunity.

CONCLUSION

The presently disclosed experimental results teach that endocytosis of apoptotic monocytes inhibits differentiation of immunostimulatory/mature dendritic cells, that apoptotic cells secrete cleaved thrombospondin-1 heparin-binding domain, and that blocking antibodies specific for heparin-binding domain optimally inhibit dendritic cell endocytosis of apoptotic cells. These results further teach that a blocking antibody specific for either heparin-binding domain, or beta1 integrin, a heparin-binding domain-binding subunit of thrombospondin-1 receptors, can be used to optimally inhibit thrombospondin-1-mediated differentiation of immunostimulatory/mature dendritic cells. As such, these results teach for the first time that isolated heparin-binding domain can be used to optimally inhibit differentiation of immunostimulatory/mature dendritic cells, and hence can be used to treat immunity-related diseases characterized by pathological immune responses, such as autoimmune diseases, transplantation-related diseases and alloimmune pregnancy loss. As such, these results further teach for the first time that compounds capable of blocking functional engagement of thrombospondin-1 heparin-binding domain and/or of beta1 integrin, such as the aforementioned blocking antibodies, can be used to effectively treat immunity-related diseases characterized by insufficient immune responses, such as infectious and/or tumoral diseases.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, or patents mentioned in this specification are herein incorporated in their entirety by reference into the specification, to the same extent as if each individual publication, or patent was specifically and individually indicated to be incorporated herein by reference. In addition, citation or identification of any reference in this application shall not be construed as an admission that such reference is available as prior art to the present invention.

REFERENCES CITED

Additional References are Cited in the Text

Adams J C. Thrombospondins: multifunctional regulators of cell interactions. Annu Rev Cell Dev Biol. 2001; 17:25-51

Albert M L, Sauter B, Bhardwaj N. Dendritic cells acquire antigen from apoptotic cells and induce class I-restricted CTLs. Nature. 1998 Mar. 5; 392 (6671):86-9.

Baenziger, N L., Brodie, G N., Majerus., P W. A thrombin sensitive protein of human platelet membranes. Prot. Natl. Acad. Sci. USA 1971 January; 68 (1):240-3

Brown S, Heinisch I, Ross E, Shaw K, Buckley C D, Savill J. Apoptosis disables CD31-mediated cell detachment from phagocytes promoting binding and engulfment. Nature. 2002 Jul. 11; 418 (6894):200-3

Calzada M J, Sipes J M, Krutzsch H C, Yurchenco P D, Annis D S, Mosher D F, Roberts D D. Recognition of the N-terminal modules of thrombospondin-1 and thrombospondin-2 by alpha6beta1 integrin. J Biol Chem. 2003 Oct. 17; 278 (42):40679-87. Epub 2003 Aug. 8.

Carol Anne Ogden, Aimee deCathelineau, Peter R. Hoffmann, Donna Bratton, Berhane Ghebrehiwet, Valerie A. Fadok, and Peter M. Henson. C1q and Mannose Binding Lectin Engagement of Cell Surface Calreticulin and CD91 Initiates Macropinocytosis and Uptake of Apoptotic Cells. J. Exp. Med., September 2001; 194: 781-796.

Chen H, Herndon M E, Lawler J. The cell biology of thrombospondin-1. Matrix Biol. 2000 December; 19 (7):597-614.

Doyen V, Rubio M, Braun D, Nakajima T, Abe J, Saito H, Delespesse G, Sarfati M. Thrombospondin 1 is an autocrine negative regulator of human dendritic cell activation. J Exp Med. 2003 Oct. 20; 198 (8):1277-83.

Ellis, R. E., Jacobson, D. M., and Horvitz, H. R. 1991. Genes required for the engulfment of cell corpses during programmed cell death in Caenorhabditis elegans. Genetics. 129:79-94

Elzie C A, Murphy-Ullrich J E. The N-terminus of thrombospondin: the domain stands apart. Int J Biochem Cell Biol. 2004 June; 36 (6):1090-101.

Fadok V A, Bratton D L, Konowal A, Freed P W, Westcott J Y, Henson P M. Macrophages that have ingested apoptotic cells in-vitro inhibit proinflammatory cytokine production through autocrine/paracrine mechanisms involving TGF-beta, PGE2, and PAF. J Clin Invest. 1998 Feb. 15; 101 (4):890-8.

Fadok V A, Savill J S, Haslett C, Bratton D L, Doherty D E, Campbell P A, Henson P M. Different populations of macrophages use either the vitronectin receptor or the phosphatidylserine receptor to recognize and remove apoptotic cells. J Immunol. 1992 Dec. 15; 149 (12):4029-35.

Ferrari do Outeiro-Bernstein M A, Nunes S S, Andrade A C, Alves T R, Legrand C, Morandi V. A recombinant NH (2)-terminal heparin-binding domain of the adhesive glycoprotein, thrombospondin-1, promotes endothelial tube formation and cell survival: a possible role for syndecan-4 proteoglycan. Matrix Biol. 2002 June; 21 (4):311-24.

Henson P M, Bratton D L, Fadok V A. Apoptotic cell removal. Curr Biol. 2001 Oct. 2; 11 (19):R795-805.

Huang C A, Fuchimoto Y, Scheier-Dolberg R, Murphy M C, Neville D M Jr, Sachs D H. Stable mixed chimerism and tolerance using a nonmyeloablative preparative regimen in a large-animal model. J Clin Invest. 2000 January; 105 (2):173-81.

Huynh M L, Fadok V A, Henson P M. Phosphatidylserine-dependent ingestion of apoptotic cells promotes TGF-beta1 secretion and the resolution of inflammation. J Clin Invest. 2002 January; 109 (1):41-50.

Lauber K, Bohn E, Krober S M, Xiao Y J, Blumenthal S G, Lindemann R K, Marini P, Wiedig C, Zobywalski A, Baksh S, Xu Y, Autenrieth I B, Schulze-Osthoff K, Belka C, Stuhler G, Wesselborg S. Apoptotic cells induce migration of phagocytes via caspase-3-mediated release of a lipid attraction signal. Cell. 2003 Jun. 13; 113 (6):717-30.

Laemmli U K. Cleavage of structural proteins during the assembly of the head of bacteriophage T4. Nature. 1970 15; 227 (5259):680-5.

Matsui N M, Smith D M, Clauser K R, Fichmann J, Andrews L E, Sullivan C M, Burlingame A L, Epstein L B. Immobilized pH gradient two-dimensional gel electrophoresis and mass spectrometric identification of cytokine-regulated proteins in ME-180 cervical carcinoma cells. Electrophoresis. 1997 March-April; 18 (3-4):409-17

Mevorach D. The immune response to apoptotic cells. Ann N Y Acad Sci. 1999; 887:191-8.

Mevorach D, Mascarenhas J O, Gershov D, Elkon K B. Complement-dependent clearance of apoptotic cells by human macrophages. J Exp Med. 1998 Dec. 21; 188 (12): 2313-20.

Moodley Y, Rigby P, Bundell C, Bunt S, Hayashi H, Misso N, McAnulty R, Laurent G, Scaffidi A, Thompson P, Knight D. Macrophage recognition and phagocytosis of apoptotic fibroblasts is critically dependent on fibroblast-derived thrombospondin 1 and CD36. Am J Pathol. 2003 March; 162 (3):771-9.

Murphy-Ullrich J E, Gurusiddappa S, Frazier W A, Hook M. Heparin-binding peptides from thrombospondins 1 and 2 contain focal adhesion-labilizing activity. J Biol Chem. 1993 Dec. 15; 268 (35):26784-9.

Ogden C A, deCathelineau A, Hoffmann P R, Bratton D, Ghebrehiwet B, Fadok V A, Henson P M. C1q and mannose binding lectin engagement of cell surface calreticulin and CD91 initiates macropinocytosis and uptake of apoptotic cells. J Exp Med. 2001 Sep. 17; 194(6):781-95.

Savill J. Phagocyte clearance of cells dying by apoptosis and the regulation of glomerular inflammation. Adv Nephrol Necker Hosp. 2001; 31:21-8.

Savill J, Dransfield I, Gregory C, Haslett C. A blast from the past: clearance of apoptotic cells regulates immune responses. Nat Rev Immunol. 2002 December; 2 (12):965-75. Review.

Savill J, Hogg N, Ren Y, Haslett C. Thrombospondin cooperates with CD36 and the vitronectin receptor in macrophage recognition of neutrophils undergoing apoptosis. J Clin Invest. 1992 October; 90 (4):1513-22.

Shoshan Y, Shapira I, Toubi E, Frolkis I, Yaron M, Mevorach D. Accelerated Fas-mediated apoptosis of monocytes and maturing macrophages from patients with systemic lupus erythematosus: relevance to in-vitro impairment of interaction with iC3b-opsonized apoptotic cells. J Immunol. 2001 Nov. 15; 167 (10):5963-9.

Stern M, Savill J, Haqsett C. Human monocyte-derived macrophage phagocytosis of senescent eosinophils undergoing apoptosis. Mediation by alpha v beta 3/CD36/thrombospondin recognition mechanism and lack of phlogistic response. Am J Pathol. 1996 149:911-921.

Stuart L M, Lucas M, Simpson C, Lamb J, Savill J, Lacy-Hulbert A. Inhibitory effects of apoptotic cell ingestion upon endotoxin-driven myeloid dendritic cell maturation. J Immunol. 2002 Feb. 15; 168 (4):1627-35.

Vandivier R W, Fadok V A, Hoffmann P R, Bratton D L, Penvari C, Brown K K, Brain J D, Accurso F J, Henson P M. Elastase-mediated phosphatidylserine receptor cleavage impairs apoptotic cell clearance in cystic fibrosis and bronchiectasis. J Clin Invest. 2002 March; 109 (5):661-70.

Verbovetski I, Bychkov H, Trahtemberg U, Shapira I, Hareuveni M, Ben-Tal O, Kutikov I, Gill O, Mevorach D. Opsonization of apoptotic cells by autologous iC3b facilitates clearance by immature dendritic cells, down-regulates HLA-DR and CD86, and up-regulates CC chemokine receptor 7. J Exp Med. 2002 Dec. 16; 196 (12):1553-61.

Vogel T, Guo N H, Krutzsch H C, Blake D A, Hartman J, Mendelovitz S, Panet A, Roberts D D. Modulation of endothelial cell proliferation, adhesion, and motility by recombinant heparin-binding domain and synthetic peptides from the type I repeats of thrombospondin. J Cell Biochem. 1993 September; 53 (1):74-84.

Voll R E, Herrmann M, Roth E A, Stach C, Kalden J R, Girkontaite I. Immunosuppressive effects of apoptotic cells. Nature. 1997 Nov. 27; 390 (6658):350-1.

Werlen G, Palmer E. The T-cell receptor signalosome: a dynamic structure with expanding complexity. Curr Opin Immunol. 2002 June; 14 (3):299-305.

Zhou, Z., Hartwieg, E., and Horvitz, H. R. 2001. CED-1 is a transmembrane receptor that mediates cell corpse engulfment in *C. elegans*. Cell. 104:43-56

What is claimed is:

1. A method of treating an inflammatory bowel disease in a subject in need thereof, the method comprising administering to the subject a therapeutically effective amount of a substantially isolated heparin-binding domain (HBD) of thrombospondin 1, wherein said HBD of thrombospondin-1 inhibits differentiation of immunostimulatory/mature antigen-presenting cells, thereby treating the inflammatory bowel disease.

2. The method of claim 1, wherein said heparin binding domain consists of SEQ ID NO: 5.

3. The method of claim 1, wherein said heparin binding domain consists of amino acids 19-224 of SEQ ID NO: 5.

4. The method of claim 1, wherein said heparin binding domain consists of amino acids 24-224 of SEQ ID NO: 5.

* * * * *

```
                       SEQUENCE LISTING

<160> NUMBER OF SEQ ID NOS: 7

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
gagtctggcg gagacaacag c                                              21

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
ttcctgcaca aacagggtga t                                              21

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
atggtgggaa tgggtcagaa g                                              21

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
cacgcagctc attgtagaag g                                              21

<210> SEQ ID NO 5
<211> LENGTH: 232
<212> TYPE: PRT
<213> ORGANISM: Homo sapiens
<220> FEATURE:
<221> NAME/KEY: misc_feature
<223> OTHER INFORMATION: N-terminal, heparin-binding domain (HBD) of
      TSP- 1

<400> SEQUENCE: 5

Met Gly Leu Ala Trp Gly Leu Gly Val Leu Phe Leu Met His Val Cys
1               5                   10                  15
```

```
Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys
225                 230

<210> SEQ ID NO 6
<211> LENGTH: 1170
<212> TYPE: PRT
<213> ORGANISM: Homo sapiens

<400> SEQUENCE: 6

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
50                  55                  60

Asn Leu Ile Pro Pro Val Pro Asp Asp Lys Phe Gln Asp Leu Val Asp
65                  70                  75                  80

Ala Val Arg Thr Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160
```

```
Gln Glu Asp Arg Ala Gln Leu Tyr Ile Asp Cys Glu Lys Met Glu Asn
                165                 170                 175
Ala Glu Leu Asp Val Pro Ile Gln Ser Val Phe Thr Arg Asp Leu Ala
            180                 185                 190
Ser Ile Ala Arg Leu Arg Ile Ala Lys Gly Gly Val Asn Asp Asn Phe
        195                 200                 205
Gln Gly Val Leu Gln Asn Val Arg Phe Val Phe Gly Thr Thr Pro Glu
    210                 215                 220
Asp Ile Leu Arg Asn Lys Gly Cys Ser Ser Thr Ser Val Leu Leu
225                 230                 235                 240
Thr Leu Asp Asn Asn Val Val Asn Gly Ser Ser Pro Ala Ile Arg Thr
                245                 250                 255
Asn Tyr Ile Gly His Lys Thr Lys Asp Leu Gln Ala Ile Cys Gly Ile
            260                 265                 270
Ser Cys Asp Glu Leu Ser Ser Met Val Leu Glu Leu Arg Gly Leu Arg
        275                 280                 285
Thr Ile Val Thr Thr Leu Gln Asp Ser Ile Arg Lys Val Thr Glu Glu
    290                 295                 300
Asn Lys Glu Leu Ala Asn Glu Leu Arg Arg Pro Leu Cys Tyr His
305                 310                 315                 320
Asn Gly Val Gln Tyr Arg Asn Asn Glu Glu Trp Thr Val Asp Ser Cys
                325                 330                 335
Thr Glu Cys His Cys Gln Asn Ser Val Thr Ile Cys Lys Lys Val Ser
            340                 345                 350
Cys Pro Ile Met Pro Cys Ser Asn Ala Thr Val Pro Asp Gly Glu Cys
        355                 360                 365
Cys Pro Arg Cys Trp Pro Ser Asp Ser Ala Asp Asp Gly Trp Ser Pro
    370                 375                 380
Trp Ser Glu Trp Thr Ser Cys Ser Thr Ser Cys Gly Asn Gly Ile Gln
385                 390                 395                 400
Gln Arg Gly Arg Ser Cys Asp Ser Leu Asn Asn Arg Cys Glu Gly Ser
                405                 410                 415
Ser Val Gln Thr Arg Thr Cys His Ile Gln Glu Cys Asp Lys Arg Phe
            420                 425                 430
Lys Gln Asp Gly Gly Trp Ser His Trp Ser Pro Trp Ser Ser Cys Ser
        435                 440                 445
Val Thr Cys Gly Asp Gly Val Ile Thr Arg Ile Arg Leu Cys Asn Ser
    450                 455                 460
Pro Ser Pro Gln Met Asn Gly Lys Pro Cys Glu Gly Glu Ala Arg Glu
465                 470                 475                 480
Thr Lys Ala Cys Lys Lys Asp Ala Cys Pro Ile Asn Gly Gly Trp Gly
                485                 490                 495
Pro Trp Ser Pro Trp Asp Ile Cys Ser Val Thr Cys Gly Gly Gly Val
            500                 505                 510
Gln Lys Arg Ser Arg Leu Cys Asn Asn Pro Thr Pro Gln Phe Gly Gly
        515                 520                 525
Lys Asp Cys Val Gly Asp Val Thr Glu Asn Gln Ile Cys Asn Lys Gln
    530                 535                 540
Asp Cys Pro Ile Asp Gly Cys Leu Ser Asn Pro Cys Phe Ala Gly Val
545                 550                 555                 560
Lys Cys Thr Ser Tyr Pro Asp Gly Ser Trp Lys Cys Gly Ala Cys Pro
                565                 570                 575
Pro Gly Tyr Ser Gly Asn Gly Ile Gln Cys Thr Asp Val Asp Glu Cys
```

-continued

```
                580                 585                 590
Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
        610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
        660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
        690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
                740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
        770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
                835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
                900                 905                 910

Val Pro Asn Pro Asp Gln Lys Asp Ser Asp Gly Asp Gly Arg Gly Asp
                915                 920                 925

Ala Cys Lys Asp Asp Phe Asp His Asp Ser Val Pro Asp Ile Asp Asp
                930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
                980                 985                 990

Asp Pro Gly Leu Ala Val Gly Tyr Asp Glu Phe Asn Ala Val Asp Phe
                995                 1000                1005
```

```
Ser Gly Thr Phe Phe Ile Asn Thr Glu Arg Asp Asp Tyr Ala
    1010                1015                1020

Gly Phe Val Phe Gly Tyr Gln Ser Ser Ser Arg Phe Tyr Val Val
    1025                1030                1035

Met Trp Lys Gln Val Thr Gln Ser Tyr Trp Asp Thr Asn Pro Thr
    1040                1045                1050

Arg Ala Gln Gly Tyr Ser Gly Leu Ser Val Lys Val Val Asn Ser
    1055                1060                1065

Thr Thr Gly Pro Gly Glu His Leu Arg Asn Ala Leu Trp His Thr
    1070                1075                1080

Gly Asn Thr Pro Gly Gln Val Arg Thr Leu Trp His Asp Pro Arg
    1085                1090                1095

His Ile Gly Trp Lys Asp Phe Thr Ala Tyr Arg Trp Arg Leu Ser
    1100                1105                1110

His Arg Pro Lys Thr Gly Phe Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Leu Lys Tyr Glu Cys Arg Asp Pro
    1160                1165                1170

<210> SEQ ID NO 7
<211> LENGTH: 5820
<212> TYPE: DNA
<213> ORGANISM: Homo sapiens

<400> SEQUENCE: 7
agccgctgcg cccgagctgg cctgcgagtt cagggctcct gtcgctctcc aggagcaacc       60
tctactccgg acgcacaggc attcccgcg cccctccagc cctcgccgcc ctcgccaccg      120
ctcccggccg ccgcgctccg gtacacacag atccctgct gggcaccaac agctccacca      180
tggggctggc ctggggacta gcgtcctgt tcctgatgca tgtgtgtggc accaaccgca      240
ttccagagtc tggcggagac aacagcgtgt ttgacatctt tgaactcacc ggggccgccc      300
gcaaggggtc tggcgccga ctggtgaagg ccccgaccc ttccagccca gctttccgca      360
tcgaggatgc caacctgatc cccctgtgc ctgatgacaa gttccaagac ctggtggatg      420
ctgtgcgggc agaaaagggt ttcctccttc tggcatccct gaggcagatg aagaagaccc      480
ggggcacgct gctggccctg agcggaaag accactctgg ccaggtcttc agcgtggtgt      540
ccaatggcaa ggcgggcacc ctggacctca gcctgaccgt ccaaggaaag cagcacgtgg      600
tgtctgtgga agaagctctc ctggcaaccg gccagtggaa gagcatcacc ctgtttgtgc      660
aggaagacag ggcccagctg tacatcgact gtgaaaagat ggagaatgct gagttggacg      720
tccccatcca aagcgtcttc accagagacc tggccagcat cgccagactc cgcatcgcaa      780 agggggggcgt caatgacaat ttccaggggg tgctgcagaa tgtgaggttt gtctttggaa      840
ccacaccaga agacatcctc aggaacaaag ctgctccag ctctaccagt gtcctcctca      900
cccttgacaa caacgtggtg aatggttcca gccctgccat ccgcactaac tacattggcc      960
acaagacaaa ggacttgcaa gccatctgcg gcatctcctg tgatgagctg tccagcatgg     1020
tcctggaact caggggcctg cgcaccattg tgaccacgct gcaggacagc atccgcaaag     1080
tgactgaaga gaacaaagag ttggccaatg agctgaggcg gctcccccta tgctataaca     1140
acggagttca gtacagaaat aacgaggaat ggactgttga tagctgcact gagtgtcact     1200
```

```
gtcagaactc agttaccatc tgcaaaaagg tgtcctgccc catcatgccc tgctccaatg    1260
ccacagttcc tgatggagaa tgctgtcctc gctgttggcc cagcgactct gcggacgatg    1320
gctggtctcc atggtccgag tggacctcct gttctacgag ctgtggcaat ggaattcagc    1380
agcgcggccg ctcctgcgat agcctcaaca accgatgtga gggctcctcg gtccagacac    1440
ggacctgcca cattcaggag tgtgacaaga gatttaaaca ggatggtggc tggagccact    1500
ggtccccgtg gtcatcttgt tctgtgacat gtggtgatgg tgtgatcaca aggatccggc    1560
tctgcaactc tcccagcccc cagatgaacg ggaaaccctg tgaaggcgaa gcgcgggaga    1620
ccaaagcctg caagaaagac gcctgcccca tcaatggagg ctggggtcct tggtcaccat    1680
gggacatctg ttctgtcacc tgtggaggag gggtacagaa cgtagtcgt ctctgcaaca     1740 accccacacc ccagtttgga ggcaaggact gcgttggtga tgtaacagaa aaccagatct    1800
gcaacaagca ggactgtcca attgatggat gcctgtccaa tcctgctttt gccggcgtga    1860
agtgtactag ctaccctgat ggcagctgga atgtggtgc ttgtcccct ggttacagtg       1920 gaaatggcat ccagtgcaca gatgttgatg agtgcaaaga agtgcctgat gcctgcttca    1980
accacaatgg agagcaccgg tgtgagaaca cggaccccgg ctacaactgc ctgccctgcc    2040
ccccacgctt caccggctca cagccctcg gccagggtgt cgaacatgcc acggccaaca     2100
aacaggtgtg caagcccgt aaccctgca cggatgggac ccacgactgc aacaagaacg      2160
ccaagtgcaa ctacctgggc cactatagcg accccatgta ccgctgcgag tgcaagcctg    2220
gctacgctgg caatggcatc atctgcgggg aggacacaga cctggatggc tggcccaatg    2280
agaacctggt gtgcgtggcc aatgcgactt accactgcaa aaaggataat tgccccaacc    2340
ttcccaactc agggcaggaa gactatgaca aggatggaat tggtgatgcc tgtgatgatg    2400
acgatgacaa tgataaaatt ccagatgaca gggacaactg tccattccat tacaacccag    2460
ctcagtatga ctatgacaga gatgatgtgg agaccgctg tgacaactgt ccctacaacc     2520
acaacccaga tcaggcagac acagacaaca tggggaagg agacgcctgt gctgcagaca    2580
ttgatggaga cggtatcctc aatgaacggg acaactgcca gtacgtctac aatgtggacc    2640
agagagacac tgatatggat ggggttggag atcagtgtga caattgcccc ttggaacaca    2700
atccggatca gctggactct gactcagacc gcattggaga tacctgtgac aacaatcagg    2760
atattgatga agatggccac cagaacaatc tggacaactg tccctatgtg cccaatgcca    2820
accaggctga ccatgacaaa gatggcaagg agatgcctg tgaccacgat gatgacaacg    2880
atggcattcc tgatgacaag gacaactgca gactcgtgcc caatcccgac cagaaggact    2940
ctgacggcga tggtcgaggt gatgcctgca aagatgattt tgaccatgac agtgtgccag    3000
acatcgatga catctgtcct gagaatgttg acatcagtga gaccgatttc cgccgattcc    3060
agatgattcc tctggacccc aaagggacat cccaaaatga ccctaactgg gttgtacgcc    3120
atcagggtaa agaactcgtc cagactgtca actgtgatcc tggactcgct gtaggttatg    3180
atgagtttaa tgctgtggac ttcagtggca ccttcttcat caacaccgaa agggacgatg    3240
actatgctgg atttgtcttt ggctaccagt ccagcagccg cttttatgtt gtgatgtgga    3300
agcaagtcac ccagtcctac tgggacacca accccacgag ggctcaggga tactcgggcc    3360
tttctgtgaa agttgtaaac tccaccacag ggcctggcga gcacctgcgg aacgccctgt    3420
ggcacacagg aaacacccct ggccaggtgc gcaccctgtg gcatgaccct cgtcacatag    3480
gctgaaagaa tttcaccgcc tacagatggc gtctcagcca caggccaaag acgggtttca    3540
ttagagtggt gatgtatgaa gggaagaaaa tcatggctga ctcaggaccc atctatgata    3600
```

```
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa ccccaggat    3780
cacttctcct tggcttcctt cttttctgtg cttgcatcag tgtggactcc tagaacgtgc   3840
gacctgcctc aagaaaatgc agttttcaaa aacagactca gcattcagcc tccaatgaat   3900
aagacatctt ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaggggag gcgcatacc cgagacgatt gtatgaagaa aatatggagg      4200
aactgttaca tgttcggtac taagtcattt tcagggatt gaaagactat tgctggattt     4260
catgatgctg actggcgtta gctgattaac ccatgtaaat aggcacttaa atagaagcag   4320
gaaagggaga caaagactgg cttctggact tcctccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata tttttatggt tacaatggca caaaattatt atcaacctaa ctaaaacatt   4620
cctttctct tttttcctga attatcatgg agttttctaa ttctctcttt tggaatgtag     4680
attttttta aatgctttac gatgtaaaat atttatttt tacttattct ggaagatctg      4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
aaatttaggc ttcatacgga aagtgtttga gagcaagtag ttgacattta tcagcaaatc   4920
tcttgcaaga acagcacaag gaaaatcagt ctaataagct gctctgcccc ttgtgctcag   4980
agtggatgtt atgggattct ttttttctct gttttatctt tcaagtggaa attagttggt   5040
tatccatttg caaatgtttt aaattgcaaa gaaagccatg aggtcttcaa tactgtttta   5100
ccccatccct tgtgcatatt tccagggaga aggaaagcat atacacttt ttctttcatt     5160
tttccaaaag agaaaaaaat gacaaaaggt gaaacttaca tacaaatatt acctcatttg   5220
ttgtgtgact gagtaaagaa ttttggatc aagcggaaag agtttaagtg tctaacaaac     5280
ttaaagctac tgtagtacct aaaaagtcag tgttgtacat agcataaaaa ctctgcagag   5340
aagtattccc aataaggaaa tagcattgaa atgttaaata caatttctga agttatgtt     5400
tttttctat catctggtat accattgctt tatttttata aattattttc tcattgccat      5460
tggaatagat atctcagatt gtgtagatat gctatttaaa taatttatca ggaaatactg   5520
cctgtagagt tagtatttct attttatat aatgttgca cactgaattg aagaattgtt       5580
ggttttttct tttttttgtt ttgtttttt ttttttttttt ttttgctttt gacctcccat        5640
ttttactatt tgccaatacc tttttctagg aatgtgcttt ttttttgtaca catttttatc     5700
cattttacat tctaaagcag tgtaagttgt atattactgt ttcttatgta caaggaacaa   5760
caataaatca tatggaaatt tatatttata aaaaaaaaaa aaaaaaaaaa aaaaaaaaa    5820
```